(12) United States Patent
Sankaranarayanan

(10) Patent No.: US 7,138,416 B2
(45) Date of Patent: Nov. 21, 2006

(54) COMPOUNDS AND THERAPEUTIC USES THEREOF

(75) Inventor: Alangudi Sankaranarayanan, Ahmedabad (IN)

(73) Assignee: Torrent Pharmaceuticals Ltd., Gujarat (IN)

( * ) Notice: Subject to any disclaimer, the term of this patent is extended or adjusted under 35 U.S.C. 154(b) by 106 days.

(21) Appl. No.: 10/408,276

(22) Filed: Apr. 8, 2003

(65) Prior Publication Data

US 2003/0225102 A1 Dec. 4, 2003

Related U.S. Application Data

(60) Provisional application No. 60/370,224, filed on Apr. 8, 2002.

(51) Int. Cl.
- A61K 31/41 (2006.01)
- A61K 31/44 (2006.01)
- A61K 31/4015 (2006.01)
- C07D 277/06 (2006.01)

(52) U.S. Cl. ............ 514/326; 514/342; 514/343; 514/374; 514/408; 546/208; 546/209; 546/269.7; 546/276.4; 548/146; 548/566

(58) Field of Classification Search ............ 514/326, 514/342, 343, 374, 408; 546/208, 209, 269.7, 546/276.4; 548/146, 566
See application file for complete search history.

(56) References Cited

U.S. PATENT DOCUMENTS 6,172,081 B1 1/2001 Damon

FOREIGN PATENT DOCUMENTS

| WO | WO 95/15309 | 6/1995 |
| WO | 99/62888 | * 12/1999 |
| WO | WO 02/34243 A2 | 5/2002 |
| WO | WO 03/002595 A2 | 1/2003 |

OTHER PUBLICATIONS

J.A. Pospisilik et al., Long-Term Treatment with the Dipeptidyl Peptidase IV Inhibitor P32/98 Causes Sustained Improvements in Glucose Tolerance, Insulin Sensitivity, Hyperinsulinemia, and β-Cell Glucose Responsiveness in VDF (fa/fa) Zucker Rats, Diabetes, vol. 51, Apr. 2002, pp. 943-950.
Vincent Marks, et al., Rapid Stick Method for Determining Blood-glucose Concentration, British Medical Journal, Jan. 30, 1965, Sputum vol., pp. 293-294.
Bernard Portha, et al., The Neonatally Streptozotocin-Induced (n-STZ) Diabetic Rats, A Family of Niddm Models, Harwood Academic Publishers, 2001, pp. 247-271.
Augustyns K. et al. Current Medical Chemistry 1999;6:311-327.
Bork Balkan and Xue Li : Am J Physiol Regulatory Integrative Comp Physiol 279:R 1449-R1454, 2000.
Balkan B. et al. Diabetologia (1999) 42:1324-1331.
Brubaker P.L. et al. Am. J. Physiol. 1997;272:E1050-1058.
Browne SE et al. Brain Pathology (1999) 9;147-163.
Carolyn FD, et al. Diabetes 47:764-769, 1998.
Doyle ME and Egan JM: Recent Prog Horm Res 56:377-399, 2001.
Drucker, D.J. Diabetes 1998: 47:159-169.
Gang et.al., Diabetes, vol. 48, Dec. 1999; 2270-2276.
Harold E Lebovitz, Drug Benefit Trends 12 (supp A):8-16, 2000, 1-12.
Harper E.J. The 24th Annual Waltham® /OSU Symposium—Oct. 28-29, 2000.
Holst JJ and Deacon CF : Diabetes, 47:1663-1670, 1998.
Ishii et. al. Journal of Gastroenterology and Hepatology (1997) 12 (Suppl.), S272-S282.
Korom S. et al. Transplantation 1997;63:1495-1500.
MacNee W, Rahman I, Trends Mol Med 2001 Feb;7(2):55-62.
Maxwell et. al, Br J Clin Pharmacol 1997; 44:307-317.
Mentlein Rolf : Regulatory Peptides 85 (1999) 9-24.
Michael A Nauck : Diabetologia. 42:373-379, 1999.
Michael Berelowitz and Ione A Kourides : Diabetes mellitus secondary to other endocrine disorders in Diabetes Mellitus : A fundamental and clinical text, second edition : Lippincott Williams & Wilkins, p. 588-593, 2000.
Munch G et.al, J Neural Transm (1998) 105:439-461.
Nguyen C et al. J Med Chem 1998; 41:2100-2110.
Qualmann C et al. Acta Diabetol 1995; 32: 13-16.
Raymond AP, et al : Diabetes 47:1253-1258, 1998.
Robert PP, et al : Metabolism 48:385-389, 1999.
Ronald A DeLellis: The Endocrine system in Robbins pathologic basis of disease, fourth edition, W.B. Saunders international edition, p. 1205, 1254-1255, 1989.

(Continued)

Primary Examiner—Taofiq Solola
(74) Attorney, Agent, or Firm—Sughrue Mion, PLLC

(57) ABSTRACT

The invention discloses a novel series of compound represented by general formula (I),

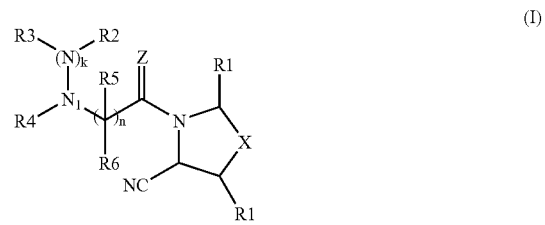

its derivatives, analogs, tautomeric forms, stereoisomers, polymorphs, pharmaceutically acceptable salts, and solvates wherein X, n, k, z, R1, R2, R3, R4, R5 and R6 are as defined in the specification that are useful in (i) normalizing elevated blood glucose levels in diabetics, (ii) treating disorders related to glucose intolerance and (iii) for scavenging free radicals in mammals.

19 Claims, 2 Drawing Sheets

OTHER PUBLICATIONS

Figure 1:
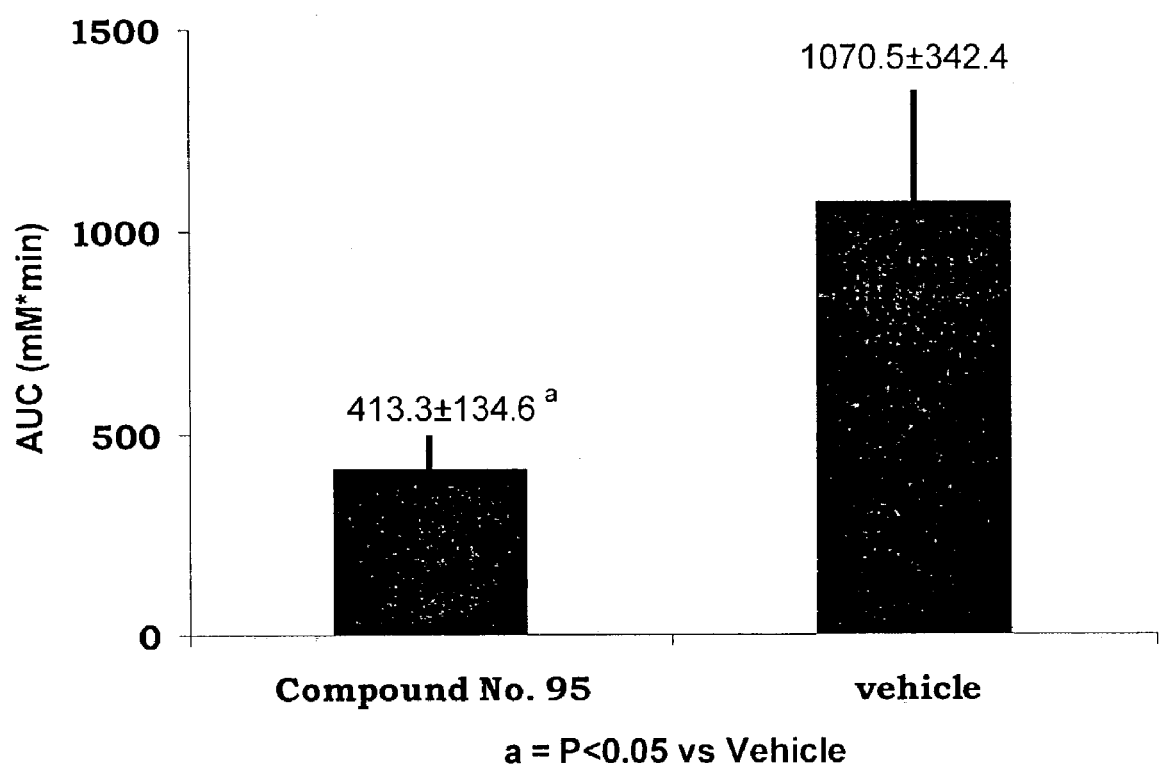

Ronald T Jung : Obesity and nutritional factors in the pathogenesis of non-insulin-dependent diabetes mellitus. Textbook of diabetes, second edition vol. 1, :Blackwell science, p. 19.12, 19.13-19.14, 1997.
Rosenfeld ME et.al. Arterioscler Thromb Vasc Biol Sep. 1998;18(9):1506-13.
Sedo A and Kraml J : Sborn Iek, 95(4):285-288, 1994.
Siegel EG, et al. : Eur J Clin Invest 29(7):610-614, 1999.
Smith M A, Biochim Biophys Acta Jul. 26, 2000; 1502(1):139-144.
Tina Vilsbol! et al. : Diabetes 50:609-613, 2001.
Tiruppathi, C., et al., Am. J. Physiol. 1993;265:G81-89.
Zalba G. et. al., J physiol Biochem, 56(1) 2000;57-64.

* cited by examiner

COMPOUNDS AND THERAPEUTIC USES THEREOF

CROSS REFERENCE TO RELATED APPLICATIONS

This application claims benefit from U.S. provisional application No. 60/370,224 filed Apr. 08, 2002 which is incorporated herein by reference in its entirety.

BACKGROUND OF THE INVENTION

1. Field of the Invention

The present invention relates to novel heterocyclic compounds useful for normalizing elevated blood glucose levels in diabetics and in treating disorders related to glucose intolerance.

These compounds are useful for controlling blood glucose level to thereby delay the onset of vascular complications in diabetic patients. These compounds are also useful to delay transition to type II diabetes in impaired glucose tolerant patients.

These compounds are useful to control blood glucose level in diabetic patients and thereby delay the onset of vascular complications in diabetic patients and also transition to type II diabetes in impaired glucose tolerant patients.

These compounds are also useful in treating disorders related to glucose intolerance like Cushing's syndrome, hyperthyroidism, obesity, hyperglucagonemia, diseases like ulcers, HIV infection, disorders related to increased gastric emptying, acid secretion and hunger, autoimmune disorders like multiple sclerosis, rheumatoid arthritis and Grave's disease (Sedo and Kraml, 1994).

These compounds also exhibit free radical scavenging activity which is useful in treatment of various disease condition caused by accumulation of free radicals in the body cells.

2. Description of the Related Art

LITERATURE REFERENCES

Augustyns K. et al. The unique properties of Dipeptidyl-peptidase IV (DPP-IV/CD 26) and the therapeutic potential of DPP-IV inhibitors. Current Medical Chemistry 1999; 6:311–327.
Bork Balkan and Xue Li: Portal GLP-1 administration in rats augments the insulin response to glucose via neuronal mechanisms. Am J Physiol regulatory Comp Physiol 279:R1449–R1454, 2000.
Balkan B, Kwasnik L, Miserendino Rep, Holst J J, Li X: Inhibition of dipeptidyl peptidase IV with NVP-DPP728 increases plasma GLP-1 (7-36 amide) concentrations and improves oral glucose tolerance in obese zucker rats. Diabetologia 42:1324–1331, 1999.
Brubaker P. L. et al. Am. J. Physiol. 1997; 272:E1050.
Browne S E et al. Brain Pathology (1999) 9;147–163.
Carolyn F D, Thomas E H, Jens J H: Dipeptidyl peptidase IV inhibition potentiates the insulinotropic effect of glucagon-like peptide 1 in the anaesthetized pig. Diabetes 47:764769, 1998.
Doyle M E and Egan J M: Glucagon-like peptide-1. Glucagon-like peptide 1. Recent Prog Horm Res 56:377-399, 2001.
Drucker, D. J. et al. Diabetes 1998; 47:159.
Gang et.al., Diabetes, Vol.48, December, 1999; 2270–2276.
Harold E Lebovitz, Pathogenesis of type-2 Diabetes; Drug Benefit Trends 12 (supp A):8–16, 2000.
Harper E. J. The 24th Annual WALTHAM [(r)]/OSU SYMPOSIUM.
Holst J J and Deacon C F: Inhibition of the activity of Dipeptidyl-peptidase IV as a treatment of type 2 diabetes. Diabetes, 47:1663–1670, 1998.
Ishii et.al. Journal of Gastroenterology and Hepatology (1997) 12 (Suppl.), S272–S282.
Korom S. et al. Transplantation 1997; 63:1495.
MacNee W, Rahman I, Trends Mol Med February 2001;7 (2):55–62.
Maxwell et. Al, Br J Clin Pharmacol 1997; 44:307–317.
Michael A Nauck: Is glucagons-like peptide 1 an incretin hormone. Diabetologia, 42:373–379, 1999.
Michael Berelowitz and lone A Kourides: Diabetes mellitus secondary to other endocrine disorders. In: Diabetes Mellitus: A fundamental and clinical text, second edition: Lippincott Williams & Wilkins, pg. 592–593, 2000.
Munch G et.al, J Neural Transm (1998) 105:439–461.
Nguyen C et al. J Med Chem 1998; 41: 2100.
Pederson R. A, et al. Diabetes 1998; 47:1253.
Qualmann C et al. Insulinotropic actions of intravenous glucagon-like peptide-1 in the fasting state in healthy volunteers. Acta Diabetologica 1995; 32: 13–16.
Raymond A P, Heather A W, Dagmar S, Robert P P, Christopher H S M, Hans-Ulrich D: Improved glucose tolerance in zucker fatty rats by oral administration of the dipeptidyl peptidase-IV inhibitor Isoleucine thiazolidide. Diabetes 47:1253–1258, 1998.
Robert P P, Hans-Ulrich D, Fred Rep, Jorn S, Heather A W, Francis L, Christopher H S M, Raymond A P: Improved glucose tolerance in rats treated with dipeptidyl peptidase-IV (CD26) inhibitor Ile-Thiazolidide. Metabolism 48:385–389, 1999.
Ronald A DeLellis: The Endocrine system. In: Robbins pathologic basis of disease, fourth edition, W. B. Saunders international edition, pg. 1254–1255, 1989.
Ronald T Jung: Obesity and nutritional factors in the pathogenesis of non-insulin-dependent diabetes mellitus. In: Textbook of diabetes, second edition: Blackwell science, pg. 19.13–19.14, 1997.
Rosenfeld M E et.al. Arterioscler Thromb Vasc Biol September 1998;18(9): 1506–13.
Sedo A and Kraml J: Dipeptidylpeptidase IV in cell proliferation and differentiation. Sborn lek, 95(4): 285–288, 1994.
Siegel E G, Scharf G, Gallwitz B, Mentlein Rep, Morys-Wortmann C, Folsch U R, Schmidt W E: Comparison of the effect of native glucagon-like peptide 1 and dipeptidyl peptidase IV-resistant analogues on insulin release from rat pancreatic islets. Eur J Clin Invest 29(7):610–614, 1999.
Smith M A, Biochim Biophys Acta 2000 Jul 26; 1502(1): 139–144.
Tina Vilsboll, Thure Krarup, Carolyn F Deacon, Sten Madsbad, Jens J Holst: Reduced postprandial concentrations of intact biologically active glucagon-like peptide 1 in type 2 diabetic patients. Diabetes 50:609–613, 2001.
Tiruppathi, C., et al., Am. J. Physiol. 1993; 265:G81–89.
Zalba G. Et.al, J physiol Biochem, 56(1) 2000; 57–64.

Diabetes mellitus is a clinically and genetically heterogenous group of disorders characterized by abnormally high levels of glucose in the blood. The hyperglycemia is due to deficiency of insulin secretion or to resistance of body cells to the action of insulin, or to a combination of these. Chronic hyperglycemia is a cause of heavy burden of morbidity and premature mortality from diabetic complications. These long-term complications can be delayed by improving glycemic control. None of the currently used medications is capable of reversing an ongoing failure of β-cell function and reduction in post prandial glucose peak represents an important target for therapeutic strategies.

Although pancreatic insulin secretion is predominantly controlled by blood glucose levels, incretins like the peptide GLP-1 derived from enteroinsular axis have an effect on insulin secretion and therefore on the blood glucose level. It is released from the gut in response to ingested nutrients, which acts on the pancreas to potentiate glucose-induced insulin secretion. GLP-1 has beneficial effects in diabetic patients in normalizing elevated blood glucose levels (Holst J and Deacon C, 1998). GLP-1 has multifaceted actions, which include stimulation of insulin gene expression, trophic effects on β-cells, inhibition of glucagon secretion, promotion of satiety, and slowing of gastric emptying. Because of glucose dependency of the peptide and glucagonostatic actions, the glucose lowering effect is self-limiting, and the hormone, therefore does not cause hypoglycemia regardless of the dose.

The pathogenesis of type-2 diabetes ordinarily involves the development of insulin resistance associated with compensatory hyperinsulinaemia followed by progressive beta-cell impairment that results in decreasing insulin secretion and hyperglycemia. Hyperglycemia itself causes additional inhibition of insulin secretion and more insulin resistance (glucose toxicity), which further accentuates the hyperglycemia. (Augustyns K. et al. The unique properties of Dipeptidyl-peptidase IV (DPP-IV/CD 26) and the therapeutic potiential of DPP-IV inhibitors. Current Medical Chemistry 1999; 6:311–327).

Current therapies ultimately fail to control blood sugar level after 3–5 years. This is due to the progressive β-cell failure in the course of the disease and insulin is finally required in most type-2 diabetic patients.

Impaired glucose tolerance and impaired fasting glucose is present in a large population. These abnormalities progress to a large extent to overt diabetes. No therapy has been approved for the prevention or delay of type-2 diabetes in these patients.

Dipeptidyl Peptidase IV (DPP-IV) inhibitors addresses to a large extent the inadequacies of the presently available therapies. It targets not only the β-cell dysfunction but also insulin resistance and increased hepatic glucose output by liver. Thus, it has a more holistic approach towards the treatment of type-2 diabetes. Furthermore, by stabilizing/reversing the progressive β-cell dysfunction, it would prevent the progression of the disease and for the same reason, it has the potential to prevent or delay the occurrence of overt diabetes in subjects with impaired fasting glucose and impaired glucose tolerance. (Pathogenesis of type-2 Diabetes; Harold E Lebovitz, Drug Benefit Trends 12 (supp A):8–16, 2000).

The presently used antihyperglycemic drugs target either insulin resistance or β-cell dysfunction. Hence, there is a need to address both of these pathologies together.

The homeodomain transcription factor, PDX-1 is essential for the early development of the pancreas and the maintenance of the β-cell phenotype. PDX-1 is known to regulate insulin, GLUT2 and islet amyloid precursor. Under conditions of sustained hyperglycemia, such as in the diabetic state, there is a downregulation of PDX-1 expression and a decrease in insulin secretion (Doyle and Egan, 2001). GLP-1 induces the differentiation of PDX-1 positive pancreatic epithelial cells into insulin-secreting cells. GLP-1 stimulates the expression of transcription factor PDX-1 while stimulating β-cell neogenesis and may thereby be an effective treatment for diabetes. GLP-1 and a long acting GLP-1 analogue exendin-4, stimulates both β-cell replication and neogenesis, resulting in increased β-cell mass and improved glucose tolerance in partial pancreatectomy rat model of type 2 diabetes (Gang et al, 1999).

GLP-$1_{7-36}$ is one of the substrate for the circulating exopeptidase dipeptidyl peptidase IV (EC 3.4.14.5), a post proline cleaving enzyme with a specificity for removing Xaa-Pro or Xaa-Ala dipeptides from the N-terminus of polypeptides and proteins. DPP-IV is widely distributed in tissues like kidney, intestine and placenta, hepatocytes, epithelial cells of pancreatic duct, central nervous system, peripheral nervous system, endothelial cells of blood vessels (Rolf, 1999), and found as soluble enzyme in blood plasma. About 50% of the GLP-$1_{7-36}$ amide released from the L cells is inactivated in the capillary bed surrounding these cells by DPP-IV. Furthermore, single pass through the liver inactivates a large fraction of the remaining active GLP-1 (>40%) (Bork and Xue, 2000). Thus these two processes together with inactivation in the circulatory system and in other organs can be expected to inactivate or remove most of the GLP-1 released from the duodenum and intestine before the peptide can reach the pancreas in the active form. Hydrolysis of GLP-$1_{7-36}$ by DPP-IV yields the truncated oligopeptide GLP-$1_{9-36}$ and the dipeptide His-Ala. This N-terminally truncated form is not insulinotropic and acts as an antagonist at GLP-1 receptor. GLP-1 is rapidly degraded in the circulation, which results in clearance that exceeds cardiac output and an apparent half-life of 1–1.5 min. The truncated metabolite is eliminated more slowly, with half-lives of 4–5 min for GLP-$1_{9-36}$. It has been speculated that DPP-IV-mediated hydrolysis is the primary mechanism of inactivation of this hormone in vivo (Tina et al, 2001).

Because of rapid degradation, the effects of single injections of GLP-1 are short lasting and for a full demonstration of its anti-diabetogenic effects, continuous intravenous infusion is required. Therefore, it is proposed that the inhibition of DPP-IV, that elevate the levels of active GLP-1 and reduce the level of antagonistic metabolite, may be useful to treat impaired glucose tolerance and perhaps transition to type 2 diabetes.

(Siegel et al (1999) reported that analogues of GLP-1 resistant to degradation by DPP-IV might help to realize the potential of GLP-1 in diabetes therapy.

DPP-IV inhibitor, Isoleucine thiazolidide (P-32/98), completely inhibited the formation of GLP-$1_{9-36}$, an antagonist at GLP-1 receptor, when it was incubated with 30 mM/L GLP-$1_{7-36}$ and serum for 21 hours. Inhibition of circulating DPP-IV enhanced insulin secretion and improved glucose tolerance in response to oral glucose challenge in lean and obese fatty (fa/fa) rats. (Raymond et al, 1998). Also it has improved glucose tolerance in zucker fatty rats (Robert et al, 1999).

It is reported that a DPP-IV inhibitor NVP-DPP-728 i.e. 1-[-2-{(5-cyanopyridin-2-yl)amino}ethylamino]acetyl-2-cyano-(S)-pyrrolidine inhibits DPP-IV activity and improves insulin secretion and glucose tolerance, through augmentation of the effects of endogenous GLP-1. The improvement in prandial glucose homeostasis during DPP-IV inhibition by this molecule suggests that inhibition of this enzyme is a promising target for treating type 2 diabetes (Balkan et al, 2000) Also this molecule showed potentiation of insulinotropic effects of GLP-1 in anaesthetized pig (Carolyn et al, 1998).

These data support a therapeutic approach of drug manipulation of plasma incretin activity by lowering glucose levels in NIDDM and other disorders involving glucose intolerance.

Dipeptidyl Peptidase IV (DPP-IV) is a proline specific protease and is involved in breaking peptide bonds before or after a proline residue. It plays an important role in the regulation of the life-time of biological active peptides like growth hormone releasing factor (GRF), Glucagon-like peptide-I (GLP-I), Gastric Inhibitory Polypeptide (GIP), Glucagon-like peptide-II (GLP-II), β-Casomorphin, morphiceptin, Human Neuropeptide Y, Human Peptide YY (Augustyns K. et al. 1999) DPP-IV is present on the surface of a subset of T-cells (lymphocytes) and has been recognized as CD 26 antigen.

Dipeptidyl peptidase-IV (DPP-IV) is a serine protease, which cleaves N-terminal dipeptides from a peptide chain containing, preferably, a proline residue in the penultimate position. DPP-IV is responsible for inactivating glucagon-like peptide-1 (GLP-1). More particularly, DPP-IV cleaves the amino-terminal His-Ala dipeptide of GLP-1, generating a GLP-1 receptor antagonist, and thereby shortens the physiological response to GLP-1. Since the half-life for DPP-IV cleavage is much shorter than the half-life for removal of GLP-1 from circulation, a significant increase in GLP-1 bioactivity (5- to 10-fold) is anticipated from DPP-IV inhibition. Since GLP-1 is a major stimulator of pancreatic insulin secretion and has direct beneficial effects on glucose disposal, DPP-IV inhibition appears to represent an attractive approach for treating non-insulin-dependent diabetes mellitus (NIDDM). GLP-1 has multifaceted actions, which include stimulation of insulin gene expression, trophic effects on β-cells, inhibition of glucagon secretion, promotion of satiety, and slowing of gastric emptying, all of which contribute to normalizing elevated blood glucose levels (Holst and Deacon, 1998). Because of glucose dependency of the peptide and glucagonostatic actions, the glucose lowering effect is self-limiting, and the hormone, therefore does not cause hypoglycemia regardless of the dose.

The exact biological functions of DPP-IV/CD 26 are still under investigation, but considerable evidence exists for the therapeutic potential of DPP-IV inhibitors.

Although a number of DPP-IV inhibitors have been described, all have limitations relating to potency, stability or toxicity. Accordingly, a great need exists for novel DPP-IV inhibitors which do not suffer from the above-mentioned limitations.

Type-II Diabetes Mellitus:

DPP-IV is involved in the degradation of GIP and GLP-I. GIP and GLP-I are considered to be most important insulin-releasing hormones (incretins) comprising the enteroinsular axis. The term enteroinsular axis refers to the signaling pathways between the gut and pancreatic islets that amplify the insulin response to absorbed nutrients. Inhibition of circulating DPP-IV with orally administered lie-thiazolidine [DPP-IV inhibitor] enhanced insulin secretion and improved glucose tolerance in response to an oral glucose challenge in lean and obese Zucker rats. The enhanced incretin response was greater in obese than in lean animals, with a more profound improvement in glucose tolerance (Pederson R. A, 1998). This was attributed to disruption of DPP-IV inactivation of GIP and GLP-I, resulting in amplification of enteroinsular axis.

DPP-IV inhibitors would have very little effect on subjects with normal blood glucose levels regardless of dose because its actions are glucose dependent (Qualmann C et al. 1995).

Hyperthyroidism and Glucose Intolerance

In patients with preexisting type I or type II diabetes mellitus, the presence of hyperthyroidism renders blood glucose management more difficult. Influences of thyroid hormone on insulin secretion and cellular metabolism have been implicated on the basis of in vitro and animal studies. In rats, thyroxine and triiodothyronine treatment inhibits the delayed phase of glucose-mediated insulin secretion-triiodothyronine being fivefold more potent than thyroxine.

In hyperthyroid states, gluconeogenic precursor (lactate and glycerol) are present in increased concentration in plasma. In rats, increased activity of mitochondrial glycerol, phosphate oxidase increases the capacity for gluconeogenesis from glycerol. It has also been shown in rats and pigs that hyperthyroidism leads to an increase in futile cycling of glucose, which could contribute to hyperglycemia. Increased activity of several enzymes that could be implicated in the increase in gluconeogenesis have been seen in response to thyroid hormone, including glucokinase, pyruvate carboxylase, phospho-enolpyruvate carboxykinase, and glucose-6-phosphatase. Studies in hyperthyroid patients report impairment in insulin suppression of hepatic glucose production. A recent study has also shown the inability to increase the insulin response appropriately to hyperglycemia and increased proinsulin levels, both fasting and in response to a meal (Michael Berelowitz and Lone A Kourides, 2000). Glucose intolerance as a result of hyperthyroidism can be better managed by enhancing the levels of GLP-1 a glucose dependent insulinotrophic agent.

Obesity and Glucose Intolerance

Obesity has been related to insulin resistance and hyperinsulinemia. Visceral obesity is associated with specific changes in skeletal muscle morphology that correlate with insulin resistance and hyperinsulinemia, namely a reduction in capillary density and an increase in the proportion of 'white' or 'glycolytic' fibers which are less insulin sensitive than red (glycolytic) fibers. TNF-alpha is secreted by adipose tissue and its circulating levels parallel total body fat mass. Circulating non-esterified fatty acid (NEFA) levels are raised in obese subjects, especially those with visceral obesity. In the liver, NEFA are oxidised to acetyl CoA, which stimulates pyruvate carboxylase and therefore gluconeogenic production of glucose from pyruvate; hepatic glucose production therefore increases. High NEFA level may also inhibit glucose utilization by skeletal muscle. Increased acetyl CoA levels inhibit pyruvate dehydrogenase, thus decreasing glucose oxidation. The combination of increased hepatic glucose output and reduced peripheral uptake effectively antagonises and would ultimately lead to hyperglycemia (Ronald T Jung, 1997). Glucose intolerance as a result of the above conditions can be managed better by the elevation of GLP-1 levels (as a result of DPP-IV inhibition).

Cushing's Syndrome and Glucose Level

Cushing's syndrome represents a distinctive constellation of clinical features associated with prolonged overproduction of impaired glucose tolerance, overt diabetes (in approximately 20%), loss of libido and impotence. Some of these abnormalities such as obesity, deranged glucose metabolism are directly attributable to increased glucocorticoids. These glucocorticoids stimulate gluconeogenesis in diabetes. Also, they increase amino acid uptake by the liver and kidney and increase the activity of enzymes required for gluconeogenesis and may lead to hyperglycemia (Ronald A DeLellius, 1989)

Glucose metabolism under the above conditions can be managed better by treatment with DPP-IV inhibitors.

Role of DPP-IV in HIV Infection

Prevention and Treatment of HIV Infection

The role of CD26 in HIV infection is also not completely clear yet, but seems to be important. Some DPP-IV inhibitors are reported to inhibit HIV infection such as pyrrolidine-2-nitriles and an irreversible cyclopeptide inhibitor (Nguyen C et al. 1998).

DPP-IV has been originally described to be a marker of activated T lymphocytes and lately DPP-IV/CD26 molecular identity has been proven CD26/DPP-IV serves as an essential cofactor for HIV entry into $CD^{4+}$ cells and that its enzyme activity is an important condition for this function (Sedo A and Kraml J, 1994). Hence inhibition of DPP-IV could prove useful in the management of HIV infection.

Immunosuppressant

It has been shown that DPP-IV/CD26-plays an important role in the immune system by a number of possible mechanisms. The exact mechanism remains to be elucidated, but a few examples are reported where DPP-IV inhibitors are useful immunosuppressants in vivo. A dipeptide diphenyl phosphonate ester was able to abrogate acute rejection and prolong allograft cardiac survival (Korom S. et al. 1997).

Role of DPP-IV Inhibitors in Ulcers, Hyperglucagonemia, Gastric Emptying and Hunger DPP-IV inhibitors increase the level of GLP-1. GLP-1 has multifaceted actions, which include stimulation of insulin gene expression, inhibition of glucagon secretion, promotion of satiety, inhibition of food intake and slowing of gastric emptying (Holst J J and Deacon C F, 1998).

GLP-1 also reduces gastric acid secretion (Michael A Nauck, 1999). Increase in gastric acid secretion is one the main reason for duodenal ulcers. By inhibiting gastric acid secretion, GLP-1 and therefore DPP-IV inhibitors may prove useful for the treatment of ulcers or can be used in combination with other antiulcer agents.

Diarrhea

DPP-IV is involved in metabolic processing of morphiceptin. Co-administration of a DPP-IV and the opiate peptide morphiceptin could be used in case of diarrhoea, as the experiment with DPP-IV deficient rats showed (Tiruppathi, C., et al., Am. J. Physiol. 1993).

Mucosal Regeneration in Patient with Intestinal Disease

DPP-IV hydrolysis of GLP-2 is responsible for its inactivation. GLP-2 has recently been shown to display intestinal growth factor activity in rodents, raising the possibility that GLP-2 may be therapeutically useful for enhancement of mucosal regeneration in patients with intestinal disease (Drucker, D. J. et al. Diabetes 1998; 47:159). The use of [$Gly^2$] GLP-2, resistant to DPP-IV hydrolysis, increases small bowel weight in mice, predominantly due to a significant increase in villous height (Brubaker P. L. et al. Am. J. Physiol. 1997).

Growth Hormone Deficiency

Since GRF is also degraded by DPP-IV, the use of a DPP-IV inhibitor together with GRF could be useful to treat children with growth hormone deficiency (Augustyns K. et al. 1999).

Neurological and Neuropsychological Disorders

Administration of a suitable DPP-IV inhibitor leads as a causal consequence to a reduced degradation of the neuropeptide Y(NPY) in the brain of mammals. Such treatment will result in a reduction or delay in the decrease of the concentration of functionally active neuronal NPY (1-36). As a consequence of the resulting enhanced stability of the endogenous NPY (1-36), NPY activity is prolonged thereby resulting among other things in functionally active NPY YI receptor activity thereby facilitating antidepressive, anxiolytic, analgesic, antihypertension and other neurological effects (WO 02/314243 dated May 02, 2002 by PROBIODRUG AG).

Cancers and Tumours

DPP-IV is able to bind proteins of the extracellular matrix as a cell adhesion molecule. This has been interpreted from the observation that the DPP-IV inhibitors interfere in vitro with the initial spreading of rat hepatocytes on a matrix consisting of fibronectin and collagen. Thus the DPP-IV inhibitors could also be used for the prevention/treatment of cancer metastasis and tumour colonization (WO 03/002595 dated 09 Jan. 2003 by PROBIODRUG AG).

Free Radical Scavenging Activity

It has been reported that compounds exhibiting free radical scavenging activity are useful in treatment of Neurodegenerative disorders such as Alzheimer's Disease, Parkinson's Disease, Huntington's Disease, Motor Neuron Disease, Prion Disease etc, (b) Diabetes and Diabetic Vascular Complications, (c) Intestinal Diseases such as Intestinal Ischemia, Radiation Enteritis, Inflammatory Bowel Disease, Gastric and Colorectal Cancers etc., (d) Liver Diseases such as Alcoholic Liver Disease, Chronic Hepatitis C etc., (e) Cancers such as Lung Cancer, Colorectal Cancer, Cervical Cancer, Breast Cancer, Malignant Melanoma etc, (f) Cardiac Diseases such as Atherosclerosis, Myocardial Infarction, Ischemic Stroke, Endothelial Dysfunction etc., (g) Opthalmic Disorders such as Cataract formation, Macular degeneration etc., (h) HIV Diseases, (i) Respiratory Diseases such as Chronic Obstructive Pulmonary Diseases, Asthma etc., (j) Renal Diseases such as Glomerulonephritis, Acute Renal Failure etc.

Neuro-Degenerative Disorders Such as Alzheimer's Disease (A.D.), Parkinson's Disease (P. D.), Huntington's Disease (H.D.), Motor Neuron Disease (M.N.D), Prion Disease As people age, their antioxidant levels diminish and these low levels are directly linked to the many diseases associated with aging such as Alzheimer's and Parkinson's disease. One of the leading hypotheses is that oxidative stress induced by ROS damages essential components of the neurons, resulting ultimately in the neuronal death. Oxidative stress is involved in various divergent events leading to neuronal damage, including an increase in membrane rigidity, DNA strand break, and impairment in glucose uptake. Several potential sources of oxidative stress in different neurodegenerative disorders have been well identified (Munch G, et al. 1998).

In A.D. mitochondrial dysfunction, amyloid beta mediated processes; transition metal accumulation and genetic factors are responsible for the redox imbalance (Smith M A, et al. 2000).

Point mutations in Superoxide Dismutase enzymes are known in the familial form of MND.

Disturbances of neuronal energy metabolism have been implicated as a pathogenetic mechanism for H.D. (Browne S E, et al. 1999)

Diabetes and Diabetic Vascular Complications (DVCs)

The cause of oxidative stress in diabetes is not yet fully understood but is thought to be due to mitochondrial dysfunction, direct enzyme inhibition by hyperglycemia, autooxidation of glucose, and activation of nicotinamide-adenine dinucleotide phosphate (NADPH)-oxidase. Oxidative stress in diabetes is also increased due to weakened defenses due to reduced endogenous antioxidants. The oxidative stress manifests itself as elevated concentrations of lipid peroxidation products, erythrocyte fragility, and decreases in the antioxidant enzyme systems (CAT, GSH Px, SOD). Recent studies also have shown a positive correlation between blood glucose concentration and oxidant-induced lymphocyte DNA damage (E. J. Harper The $24^{th}$ Annual WALTHAM®/OSU SYMPOSIUM).

ROS are generated during glucose oxidation and formation of advanced glycation end products (AGE). Evidence has accumulated indicating that the generation of ROS plays an important role in the development of DVCs. Many biochemical pathways associated with hyperglycemia such as advanced glycosylation, glucose auto oxidation, and polyol pathway can increase the production of free radicals. Hyperglycemia in diabetic patients leads to excess autooxidation of glucose thereby reducing molecular oxygen and yielding oxidizing intermediates such as superoxide ions ($O_2^-$), hydroxyl radicals ($^-OH$), and hydrogen peroxide ($H_2O_2$). Free radicals accelerate the formation of advanced glycosylation end products (AGE), because fragmentation and conformational changes occurring during glycosylation and glucose oxidation have been shown to be dependent upon free radicals. AGEs in turn supply more free radicals; this process is termed as oxidative glycosylation or glycoxidation. These free radicals impair vascular relaxation by inactivating or quenching nitric oxide (NO) and also adversely affect the endothelial function. Evidence also suggests that Maillard reaction acts as an amplifier of oxidative damage in aging and diabetes.

Intestinal Diseases

Oxidative stress is an important cause of tissue injury that occurs in inflammation and ischemia. Intestinal ischemia, radiation enteritis, inflammatory bowel disease, and promotion of gastric and colorectal cancers are some of the gastrointestinal conditions where oxidative stress is implicated in the pathogenesis.

Liver Diseases

Alcoholic liver disease—Ethanol induces an increase in lipid peroxidation either by enhancing ROS or decreasing the level of endogenous antioxidants. Ethanol also induces variety of cytochrome P450 enzymes in microsomes and xanthine oxidases in cytosol. The role of these enzymes in the generation of oxidative stress has been well established in various studies (Ishii H, et al. 1997).

Chronic hepatitis C—Enhanced oxidative stress initiates a fibrogenesis cascade in the liver of patients with chronic hepatitis C. Evidences are coming up supporting an oxidative stress pathway leading to active fibrogenesis in chronic hepatitis C. This fibrogenesis cascade characteristic of severe chronic hepatitis C (e.g., oxidative stress, induction of c-myb, activation of stellate cells, and collagen gene expression) is stimulated by ROS.

Cancers

Oxidative damage to DNA is a result of interaction of DNA with ROS, in particular the hydroxyl radical. The hydroxyl radicals produce multiple modifications in DNA. Oxidative attack by OH radical on the deoxyribose moiety leads to the release of free bases from DNA, generating strand breaks with various sugar modifications and simple abasic (AP) sites.

ROS also interact with and modify cellular protein, lipid, and DNA, which results in altered target cell function. The accumulation of oxidative damage has been implicated in both acute and chronic cell injury including possible participation in the formation of cancer. Acute oxidative injury may produce selective cell death and a compensatory increase in cell proliferation. This stimulus may result in the formation of newly initiated preneoplastic cells and/or enhance the selective clonal expansion of latent initiated preneoplastic cells. Similarly, sublethal acute oxidative injury may produce unrepaired DNA damage and result in the formation of new mutations and, potentially, new initiated cells. ROS, therefore, can have multiple effects in the initiation stage of carcinogenesis by mediating carcinogen activation, causing DNA damage, and interfering with the repair of the DNA damage.

Benefits of various antioxidants in preventing or treating following cancers have been extensively studied.
1) Lung cancer
2) Colorectal cancer
3) Cervical cancer
4) Breast cancer
5) Malignant melanoma Oxidative Stress in Cardiac Diseases Lifelong high levels of antioxidant nutrients are supposed to protect against the development of heart disease. High doses of antioxidants in the month following an acute heart attack have been shown to significantly reduce the number of deaths, as well as the extent of cardiac damage in non-fatal cases.

It is currently thought that increase in oxidative stress is involved in the pathophysiology of endothelial dysfunction that accompanies a number of cardiovascular risk factors including hypercholesterolemia, hypertension and cigarette smoking. It also plays a pivotal role in the evolution of clinical conditions such as atherosclerosis and heart failure. Oxidative stress can activate redox-sensitive kinase cascades and transcription factors such as $NF_KB$ and AP-1, with resulting increases in the expression of factors associated with an inflammatory response and cellular proliferation. There are three enzyme systems producing reactive oxygen species in the vascular wall: NADH/NADPH oxidase, xanthine oxidoreductase, and endothelial nitric oxide synthase (Zalba G.et al, 2000, Rosenfeld M E., 1998).

Atherogenesis is regarded as the outcome of interactions among multiple stimuli. Endothelial dysfunction plays a key role in the development of atherosclerosis. Elevated homocysteine concentrations are associated with rapid onset endothelial dysfunction, which is another mechanism by which increased oxidative stress contributes to atherosclerosis. Oxidation of low-density lipoprotein plays an important role at several steps in atherogenesis. Oxidative stress also activates $NF_KB$, which induces expression of genes controlling cytokine expression and leukocyte adhesion to vascular wall. (Maxwell, et al. 1997).

Animal studies have provided evidence by suggesting that free radicals may promote thrombosis, directly damage vascular cells and other tissues, and interfere with vasomotor regulation with the clinical sequelae of myocardial infarction and ischemic stroke.

In tissues where oxygen supply becomes used up following ischemia, as in myocardial ischemia, the enzyme xanthine oxidase is changed to a form that has potential to reduce oxygen to superoxides. On readmission of oxygen e.g. by reperfusion there is a burst of free radical generation. ROS are formed at an accelerated rate in post-ischemic myocardium. Thus biochemical damage due to free radicals contributes to the ischemic injury.

Oxidative stress also seems to be one of the mechanisms that may produce membrane defects and result in intracellular calcium overload, and cardiac contractile dysfunction in the stunned myocardium.

Macular Degeneration and Cataract

Oxidative damage to lens of the eye with increase in age has a major contribution in cataract formation. Macular degeneration is also being recognized as a consequence of oxidative damage.

HIV Disease

Perturbation of anti-oxidant defense system has been observed in various tissues in HIV patients. Oxidative stress may contribute to several aspects of HIV disease pathogenesis such as viral replication, inflammatory response, and decreased immune cell proliferation, loss of immune function, apoptosis, chronic weight loss. Antioxidants may offer a promising treatment to HIV patients.

Chronic Obstructive Pulmonary Diseases (COPD)

Alteration in the alveolar and lung metabolism of glutathione is widely recognized as a central feature of many inflammatory lung diseases including COPD. These changes are a result of the alteration in the gene expression of the gamma-glutamyl cystine synthase (Gamma-GCS), the rate-limiting enzyme in glutathione synthesis. Oxidative stress is implicated in the pathogenesis of COPD, since it results in inactivation of anti proteinases, airspace epithelial injury, mucus hypersecretion, increased influx of neutrophils into the lungs, transcription factor activation and gene expression of pro-inflammatory mediators (MacNee W, et al. 2001).

Renal Disease

ROS have been implicated not only in the genesis of different forms of renal disease, predominantly experimentally induced glomerulonephritis, but also in different forms of acute renal failure.

Asthma

Although the pathogenesis of asthma is not fully defined, a typical feature is an increase in the number of inflammatory cells in the lung. Such cells generate ROS, which are involved in the pathophysiology of asthma, including airway smooth muscle contraction, increased airway reactivity, and increased vascular permeability.

Effect of Antioxidant Status on Immunologic Function

The immune system is particularly sensitive to oxidative stress, primarily because immune cells rely heavily on cell-to-cell communication to work effectively. Peroxidation of cell membranes compromises membrane integrity and disrupts intracellular signaling.

Cataract:

Oxidative Damage to Lens of Eye with Increase in Age Has Been a Major Contribution in Cataract Formation.

Thus, by scavenging the free radicals, the following diseases can be treated or controlled:

1) Neurodegenerative disorders
   (a) Alzheimer's Disease
   (b) Parkinson's Disease
   (c) Huntington's Disease
   (d) Motor Neuron Disease
   (e) Prion Disease
2) Diabetes and Diabetic Vascular Complications
3) Intestinal Diseases
   (a) Intestinal Ischemia
   (b) Radiation Enteritis
   (c) Inflammatory Bowel Disease
   (d) Gastric and Colorectal Cancers
4) Liver Diseases
   (a) Alcoholic Liver Disease
   (b) Chronic Hepatitis C
5) Cancers
   (a) Lung Cancer
   (b) Colorectal Cancer
   (c) Cervical Cancer
   (d) Breast Cancer
   (e) Malignant Melanoma
6) Cardiac Diseases
   (a) Atherosclerosis
   (b) Myocardial Infarction
   (c) Ischemic Stroke
   (d) Endothelial dysfunction
7) Opthalmic Disorders
   (a) Cataract formation
   (b) Macular degeneration
8) HIV Disease
9) Respiratory Diseases
   (a) Chronic Obstructive Pulmonary Diseases (COPD)
   (b) Asthma
10) Renal Diseases
    (a) Glomerulonephritis
    (b) Acute Renal failure

OBJECTS OF THE INVENTION

The first object of the present invention is to provide a new class of compounds which normalize elevated blood glucose levels in diabetic patients thereby delaying diabetic complications and preventing transition to type II diabetes in impaired glucose tolerant patients.

These compounds exhibit in vitro DPP-IV inhibitory activity. DPP-IV inhibitors enhance the level of active GLP-1, which would be advantageous in treating hyperglycemia. Added advantage is that there is no risk of hypoglycemia, since GLP-1 increases glucose mediated insulin secretion. Due to non-peptide nature of the compounds, they can be conveniently administered orally. The increase in GLP-1 level in the active form provides for multifaceted action in respect of increase in insulin level, decrease in glucagon level, neogenesis of pancreatic β-cell, stimulation of insulin gene expression, and promotion of satiety, all of which contribute to beneficial effects in a diabetic patient.

Another object of the invention is to provide a method of treatment of a diabetic patient with glucose intolerance by administration of the compounds of the invention or pharmaceutically acceptable salts thereof either singly or in combination with drugs for anti-diabetic or other therapies for Cushing's syndrome, hyperthyroidism, HIV infection, obesity, ulcers, disorders related to hyperglucagonemia, gastric emptying and hunger in required dosage in admixture with pharmaceutically acceptable diluents, solvents, excepients, carriers or other media as may be appropriate for the purpose.

A further object of the invention is to provide a class of compounds having free radical scavenging activity which are useful for treatment of (a) Neurodegenerative disorders such as Alzheimer's Disease, Parkinson's Disease, Huntington's Disease, Motor Neuron Disease, Prion Disease etc, (b) Diabetes and Diabetic Vascular Complications, (c) Intestinal Diseases such as Intestinal Ischemia, Radiation Enteritis, Inflammatory Bowel Disease, Gastric and Colorectal Cancers etc., (d) Liver Diseases such as Alcoholic Liver Disease, Chronic Hepatitis C etc., (e) Cancers such as Lung Cancer, Colorectal Cancer, Cervical Cancer, Breast Cancer, Malignant Melanoma etc., (f) Cardiac Diseases such as Atherosclerosis, Myocardial Infarction, Ischemic Stroke, Endothelial Dysfunction etc., (g) Opthalmic Disorders such as Cataract formation, Macular degeneration etc., (h) HIV Diseases, (i) Respiratory Diseases such as Chronic Obstructive Pulmonary Diseases, Asthma etc., (j) Renal Diseases such as Glomerulonephritis, Acute Renal Failure etc.

Yet another object of the present invention is to provide a method of preparation of these compounds.

A still further object of the invention is to provide a pharmaceutical composition comprising said compound in association with a pharmaceutical acceptable carrier, diluent or excepients.

Yet another object of the invention is to provide a method of treatment and/or prophylaxis of mammals including human beings for diseases relating to glucose intolerance and/or disease conditions caused by accumulation of free radicals in the body cells.

SUMMARY OF THE INVENTION

The present invention provides novel compounds represented by general formula (I) and its pharmaceutically acceptable salts, which is to be understood as also including its derivatives, analogs, tautomeric forms, stereoisomers, polymorphs and their pharmaceutically acceptable solvates, which are useful for one or more of (i) normalizing elevated blood glucose levels in diabetes, (ii) treating disorders related to glucose intolerance and (iii) scavenging free radicals from body cells.

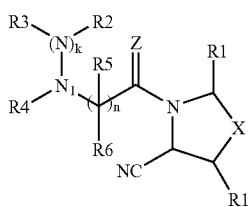

(I)

wherein

X is O, S, SO, $SO_2$, NR7 or CHR1;

n is null or 1;

k is null or 1;

Z is O, S, and NR7;

R1 at two positions are independently selected from hydrogen or a substituted or unsubstituted group selected from linear or branched $(C_1-C_{12})$alkyl, $(C_2-C_{12})$alkenyl, $(C_3-C_7)$cycloalkyl, $(C_5-C_7)$cycloalkenyl, bicycloalkyl, bicycloalkenyl, heterocycloalkyl, aryl, aryloxy, aralkyl, aralkoxy, heteroaryl, heteroaralkyl, heteroaryloxy, heteroaralkoxy, wherein one or more heteroatoms are independently selected from O, N or S;

R2, R3, R4 and R7 are independently selected from hydrogen, perhaloalkyl, —(CO)NR8R9, —(CO)OR8, —(CO)OR8, —SO2R8, —SOR8, substituted or unsubstituted groups selected from linear or branched $(C_1-C_{12})$alkyl, $(C_2-C_{12})$alkenyl, $(C_3-C_7)$cycloalkyl, $(C_5-C_7)$cycloalkenyl, bicycloalkyl, amidino bicycloalkenyl, heterocloalkyl, aryl, aralkyl, heteroaryl, heteroaralkyl, wherein one or more heteroatoms are independently selected from O, N or S;

R5 and R6 are independently selected from by hydrogen or a substituted or unsubstituted group selected from linear or branched $(C_1-C_{12})$alkyl, $(C_2-C_{12})$alkenyl, $(C_3-C_7)$cycloalkyl, $(C_5-C_7)$cycloalkenyl, bicycloalkyl, bicycloalkenyl, heterocycloalkyl, aryl, aralkyl, heteroaryl, heteroaralkyl, wherein one or more heteroatoms are independently selected from O, N or S;

R8 and R9 are independently selected from hydrogen or a substituted and unsubstituted group selected from linear or branched $(C_1-C_{12})$alkyl, alkoxyaryl, alkoxyalkyl, alkoxycycloalkyl, alkoxyaryl, perhaloalkyl, $(C_2-C_{12})$alkenyl, $(C_3-C_7)$cycloalkyl, perhalocycloalkyl, haloheterocycloalkyl, cyanoheterocycloalkyl, perhaloheterocycloalkyl, $(C_5-C_7)$cycloalkenyl, bicycloalkyl, bicycloalkenyl, heterocycloalkyl, aryl, aralkyl, heteroaryl, heteroaralkyl, perhaloaryl, perhaloheteroaryl;

wherein in the groups represented by R1, R2, R3, R4, R5, R6, R7, R8 and R9 when substituted, the substitutents are optionally and independently bridged by —(CO)—, —(CO)O, —(CO)NH—, —NH—, —NR8-, —O—, —S—, —(SO)—, —(SO2)—, —(SO2)NH—, —NH(SO2)—, —O(CO)— or —NH(CO)—; and are selected from halogen, hydroxy, nitro, cyano, amino, oxo, oxime, unsubstituted or substituted by R10 for the groups selected from linear or branched $(C_1-C8)$alkyl, $(C_3-C_7)$ cycloalkyl, alkylcycloalkyl, perhaloalkyl, perhalocycloalkyl, aryl, aralkyl, alkylaryl, alkylheteroaryl, aralkoxylalkyl, perhaloaryl, alkylheterocycloalkyl, heterocycloalkyl, perhaloheterocyclyloalkyl, heteroaryl, heteroaralkyl, alkylaryl, perhaloheteroaryl, acyl, acyloxy, acylamino, alkylamino, arylamino, aralkoxy, alkoxyalkyl, alkylthio, thioalkyl, arylthio, thioaryl, carboxylic acid or its derivatives, or sulfonic acid or its derivatives wherein the groups/substituents present on same or adjacent atoms such as carbon or nitrogen, together optionally and independently may form a five or a six or a seven membered ring optionally containing one or more double bonds and optionally containing one or more heteroatoms selected from O, N or S;

and wherein

R10 is independently selected from halogen, hydroxy, nitro, cyano, amino, oxo or oxime, and pharmaceutically usable hydrates and salts thereof;

with the proviso that, if k is null, then R4 and R6 together form an optionally six or seven membered ring, which optionally contains two to three heteroatoms independently selected from O, S and NR7 with R1 as hydrogen, and $N_1$ is attached to hydrogen.

As used herein, aryl and heteroaryl ring includes up to two conjugated or fused ring systems.

Pharmaceutically acceptable salts forming part of this invention are intended to include not limited to salts of the carboxylic acid moiety such as alkali metal salts like Li, Na and K salts; alkaline earth metal salts like Ca and Mg salts; salts of organic bases such as lysine, arginine, guanidine, diethanolamine, choline, trimethamine and the like; ammonium or substituted ammonium salts and aluminum salts. Salts may be acid addition salts which defines but not limited to sulfates, nitrates, phosphates, perchlorates, borates, hydrohalides, acetates, perhaloacetates, tartrates, maleates, citrates, succinates, palmoates, methanesulfonates, benzoates, salicylates, hydroxynaphthoates, benzensulfonates, ascorbates, glycerophosphates, ketoglutarates and the like.

The invention also provides a process for preparation of the compounds as defined above.

The invention further provides pharmaceutical composition comprising compounds of the invention in association with a pharmaceutically acceptable carrier, diluent or excepient.

The invention also provides a method of treatment of mammals including human beings in disease conditions resulting from glucose intolerance and/or accumulation of free radical in the body cells by administering an effective compound of compounds of the invention to the subject in need thereof.

The invention further provides use of the compounds of invention in the manufacture of a medicament useful for treatment of diseases conditions resulting from glucose intolerance and/or accumulation free radical in the body cells.

BRIEF DESCRIPTION OF ACCOMPANYING DRAWINGS

FIG. 1: This shows the effect of test compound (compound No. 95) on AUC in OGTT for the glucose load of 1 gm/kg in nSTZ induced diabetic rat.

Figure 2:
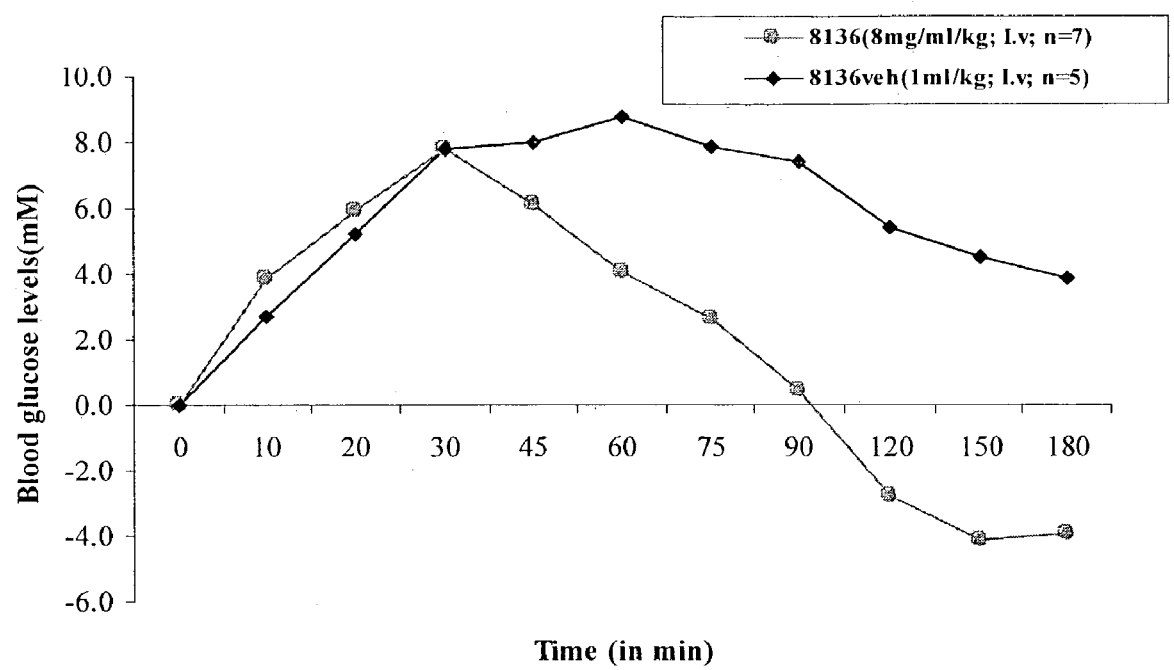

FIG. 2: This shows the effect of test compound (compound No. 95) pre-treatment on the glucose excursion.

DETAILED DESCRIPTION OF THE INVENTION

The representative compounds of formula (I) as referred above are listed in Table 1 below which can be conveniently prepared, by methods as described hereinafter. These compounds may exist both as diastereomeric mixtures or as the diastereomerically pure or enantiomerically pure compounds.

TABLE 1

Representative Compounds

| Comp No. | R1 | R2 | R3 | -R4–R6- | R4 | R5 | R6 | k | n | X | Z | Salt |
|---|---|---|---|---|---|---|---|---|---|---|---|---|
| 1 | H | — | — | —CH$_2$—CH$_2$—NH—CH$_2$— | * | H | * | 0 | 1 | —CH$_2$ | O | 2 CF$_3$COOH |
| 2 | H | — | — | —CH$_2$—CH$_2$—N(isopropyl)-CH$_2$— | * | H | * | 0 | 1 | —CH$_2$ | O | 2 CF$_3$COOH |
| 3 | H | H | H | — | Ph | H | H | 1 | 1 | —CH$_2$ | O | CF$_3$COOH |
| 4 | H | H | H | — | H | H | H | 1 | 1 | —CH$_2$ | O | CF$_3$COOH |
| 5 | H | H | —CO(O)tBu | — | H | H | H | 1 | 1 | S | O | — |
| 6 | H | H | —CO(O)tBu | — | Ph | H | H | 1 | 1 | —CH$_2$ | O | — |
| 7 | H | H | —CO(O)tBu | — | H | H | H | 1 | 1 | —CH$_2$ | O | — |
| 8 | H | H | H | — | p-nitrobenzyl | H | H | 1 | 1 | —CH$_2$ | O | CF$_3$COOH |
| 9 | H | H | H | — | Ph | H | H | 1 | 1 | S | O | CF$_3$COOH |
| 10 | H | H | H | — | CH$_2$CH(CH$_3$)$_2$ | H | H | 1 | 1 | CH$_2$ | O | — |
| 11 | H | H | H | — | Benzyl | H | H | 1 | 1 | —CH$_2$ | O | CF$_3$COOH |
| 12 | H | H | H | — | CH(CH$_3$)$_2$ | H | H | 1 | 1 | —CH$_2$ | O | CF$_3$COOH |
| 13 | H | Ethyl | Ethyl | — | H | H | H | 1 | 1 | S | O | — |
| 14 | H | H | H | — | Ethyl | H | H | 1 | 1 | —CH$_2$ | O | CF$_3$COOH |
| 15 | H | H | H | — | H | H | H | 1 | 1 | S | O | CF$_3$COOH |
| 16 | H | H | H | — | Benzyl | H | H | 1 | 1 | S | O | CF$_3$COOH |
| 17 | H | H | H | — | p-nitrobenzyl | H | H | 1 | 1 | S | O | CF$_3$COOH |
| 18 | H | H | H | — | Cyclopentyl | H | H | 1 | 1 | —CH$_2$ | O | CF$_3$COOH |
| 19 | H | H | H | — | Cyclopentyl | H | H | 1 | 1 | S | O | CF$_3$COOH |
| 20 | H | H | H | — | Cyclohexyl | H | H | 1 | 1 | —CH$_2$ | O | CF$_3$COOH |
| 21 | H | H | H | — | Cyclohexyl | H | H | 1 | 1 | S | O | CF$_3$COOH |
| 22 | H | H | H | — | CH(CH3)CH$_2$ CH$_3$ | H | H | 1 | 1 | —CH$_2$ | O | CF$_3$COOH |
| 23 | H | H | H | — | CH(CH3)CH$_2$ CH$_3$ | H | H | 1 | 1 | S | O | CF$_3$COOH |
| 24 | H | H | H | — | SO$_2$Ph | H | H | 1 | 1 | —CH$_2$ | O | CF$_3$COOH |
| 25** | H | H | H | — | 4-CH$_3$-cyclohexyl | H | H | 1 | 1 | S | O | CF3COOH |
| 26** | H | H | H | — | 4-CH$_3$-cyclohexyl | H | H | 1 | 1 | —CH$_2$ | O | CF3COOH |
| 27 | H | H | H | — | 2-pyridyl | H | H | 1 | 1 | —CH$_2$ | O | 2CF$_3$COOH |
| 28 | H | H | H | — | -cycloheptyl | H | H | 1 | 1 | S | O | CF$_3$COOH |
| 29*** | H | H | H | — | 4-CH$_3$-cyclohexyl | H | H | 1 | 1 | S | O | CF$_3$COOH |
| 30 | H | H | H | — | -cycloheptyl | H | H | 1 | 1 | —CH$_2$ | O | CF$_3$COOH |
| 31 | H | H | H | — | CH(CH3)2 | — | — | 1 | 0 | S | O | HCl |
| 32 | H | H | H | — | -cyclohexyl | — | — | 1 | 0 | —CH$_2$ | O | HCl |
| 33 | H | H | H | — | -cyclohexyl | — | — | 1 | 0 | S | O | HCl |
| 34 | H | H | -cyclohexyl | — | H | H | H | 1 | 1 | —CH$_2$ | O | CF$_3$COOH |
| 35 | H | H | H | — | Phenyl | — | — | 1 | 0 | S | O | CF$_3$COOH |
| 36 | H | H | -isopropyl | — | -cyclohexyl | H | H | 1 | 1 | S | O | HCl |
| 37 | H | H | H | — | 4-CH$_3$-cyclohexyl | H | H | 1 | 1 | —CH$_2$ | O | CF$_3$COOH |
| 38 | H | H | -isopropyl | — | -cyclohexyl | H | H | 1 | 1 | —CH$_2$ | O | — |
| 39 | H | H | H | — | 4-CH$_3$-cyclohexylmethyl | H | H | 1 | 1 | —CH$_2$ | O | CF$_3$COOH |
| 40 | H | H | H | — | 4-chlorophenyl | H | H | 1 | 1 | —CH$_2$ | O | CF$_3$COOH |
| 41 | H | H | H | — | H | H | -isopropyl | 1 | 1 | —CH$_2$ | O | CF$_3$COOH |
| 42 | H | H | -ethyl | — | 4-CH$_3$-cyclohexyl | H | H | 1 | 1 | S | O | — |

TABLE 1-continued

Representative Compounds

| Comp No. | R1 | R2 | R3 | -R4–R6- | R4 | R5 | R6 | k | n | X | Z | Salt |
|---|---|---|---|---|---|---|---|---|---|---|---|---|
| 43 | H | H | H | — | -morpholino-carbonyl | H | H | 1 | 1 | S | O | $CF_3COOH$ |
| 44 | H | H | -isopropyl | — | 4-$CH_3$-cyclohexyl | H | H | 1 | 1 | S | O | $CF_3COOH$ |
| 45 | H | H | -2-oxo-2-(2'-cyano-pyrolidino-1-yl)-ethyl | — | -cyclohexyl | H | H | 1 | 1 | —$CH_2$ | O | $CF_3COOH$ |
| 46 | H | H | -N(2-(2-pyridyl)ethyl)amino carbonyl | — | -N(2-(2-pyridyl)ethyl)amino carbonyl | H | H | 1 | 1 | S | O | $2CF_3COOH$ |
| 47 | H | H | H | — | -4-tertbutyl-cyclohexyl | H | H | 1 | 1 | S | O | $CF_3COOH$ |
| 48 | H | H | H | — | -1-tetralino | H | H | 1 | 1 | —$CH_2$ | O | $CF_3COOH$ |
| 49 | H | H | H | — | -4-tertbutyl-cyclohexyl | H | H | 1 | 1 | S | O | $CF_3COOH$ |
| 50 | H | -cyclohexyl | -2-oxo-2-(2'-cyano-pyrolidino-1-yl)-ethyl | — | H | H | H | 1 | 1 | S | O | — |
| 51 | H | H | H | — | 1-isopropyl-4-piperidinyl | H | H | 1 | 1 | S | O | $CF_3COOH$ |
| 52 | H | H | H | — | 1-(4-cyanobenzyl)-4-piperidinyl | H | H | 1 | 1 | S | O | $2CF_3COOH$ |
| 53 | H | H | 1(3-pyridinyl-methyl)-4-piperidinyl | — | 4-$CH_3$-cyclohexyl | H | H | 1 | 1 | S | O | — |
| 54 | H | H | 1-isopropyl-4-piperidinyl | — | 4-$CH_3$-cyclohexyl | H | H | 1 | 1 | S | O | — |
| 55 | H | H | H | — | 1(p-tolunesulfonyl)-4-piperidinyl | H | H | 1 | 1 | S | O | $CF_3COOH$ |
| 56 | H | H | 1(p-tolune-sulfonyl)-4-piperidinyl | — | -methyl | H | H | 1 | 1 | S | O | $CF_3COOH$ |
| 57 | H | H | H | — | 1(3-pyridinylmethyl)-4-piperidinyl | H | H | 1 | 1 | S | O | $3CF_3COOH$ |
| 58 | H | H | 1-(4-cyanobenzyl)-4-piperidinyl | — | -methyl | H | H | 1 | 1 | S | O | $2CF_3COOH$ |
| 59 | H | H | 1(3-pyridinyl-methyl)-4-piperidinyl | — | -methyl | H | H | 1 | 1 | S | O | $3CF_3COOH$ |
| 60 | H | H | H | — | 4-n-propyl-cyclohexyl | H | H | 1 | 1 | S | O | $CF_3COOH$ |
| 61 | H | H | H | — | 1-(4-nitrobenzyl)-4-piperidinyl | H | H | 1 | 1 | S | O | $CF_3COOH$ |
| 62 | H | H | H | — | 1(4-chlorobenzene-sulfonyl)-4-piperidinyl | H | H | 1 | 1 | S | O | $CF_3COOH$ |
| 63 | H | H | H | — | 2-norcamphoryl | H | H | 1 | 1 | S | O | $CF_3COOH$ |
| 64 | H | H | H | — | 4-n-propyl-cyclohexyl | H | H | 1 | 1 | S | O | $CF_3COOH$ |
| 65 | H | H | H | — | 1(4-methylcyclo-hexylcarbonyl)-4-piperidinyl | H | H | 1 | 1 | S | O | $3CF_3COOH$ |
| 66 | H | H | H | — | 1(acetyl)-4-piperidinyl | H | H | 1 | 1 | S | O | $CF_3COOH$ |
| 67 | H | H | H | — | 4-methylcyclo-hexyl | H | H | 1 | 1 | $SO_2$ | O | $CF_3COOH$ |
| 68 | H | H | 4-methylcyclo-hexyl | — | methyl | H | H | 1 | 1 | S | O | — |
| 69 | H | H | 4-methylcyclo-hexyl | — | methyl | H | H | 1 | 1 | S | O | — |
| 70 | H | H | H | — | 1(2,3-dichlorophenylcarbonyl)-4-piperidinyl | H | H | 1 | 1 | S | O | $CF_3COOH$ |
| 71 | H | H | 1(4-chlorobenzene-sulfonyl)-4-piperidinyl | — | methyl | H | H | 1 | 1 | S | O | $CF_3COOH$ |
| 72 | H | H | H | — | 4-piperidinyl | H | H | 1 | 1 | S | O | $2CF_3COOH$ |
| 73 | H | H | H | — | 1(4-chlorobenzene-sulfonyl)-4-piperidinyl | H | H | 1 | 1 | —$CH_2$ | O | $CF_3COOH$ |
| 74 | H | H | Acetyl | — | 4-$CH_3$-cyclohexyl | H | H | 1 | 1 | S | O | — |
| 75 | H | H | H | — | 2-adamentyl | H | H | 1 | 1 | S | O | $CF_3COOH$ |
| 76 | H | H | H | — | 1(tertbutylcarbonyl)-4-piperidinyl | H | H | 1 | 1 | S | O | $CF_3COOH$ |

TABLE 1-continued

Representative Compounds

| Comp No. | R1 | R2 | R3 | -R4–R6- | R4 | R5 | R6 | k | n | X | Z | Salt |
|---|---|---|---|---|---|---|---|---|---|---|---|---|
| 77 | H | H | H | — | 1(5-trifluoro-methyl-2-pyridyl)-4-piperidinyl | H | H | 1 | 1 | S | O | 2CF$_3$COOH |
| 78 | H | H | H | — | 4-methane-sulfonamido-cyclohexyl | H | H | 1 | 1 | S | O | CF$_3$COOH |
| 79 | H | H | H | — | 3,3,5-trimethyl-cyclohexyl | H | H | 1 | 1 | S | O | CF$_3$COOH |
| 80 | H | H | -ethyl | — | -isopropyl | H | H | 1 | 1 | S | O | CF$_3$COOH |
| 81 | H | H | H | — | 1-benzyl-4-piperidinyl | H | H | 1 | 1 | S | O | CF$_3$COOH |
| 82 | H | H | H | — | 4-(4-chlorophenyl-sulfonamido)-cyclohexyl | H | H | 1 | 1 | S | O | CF$_3$COOH |
| 83 | H | # | H | — | # | H | H | 1 | 1 | S | O | — |
| 84 | H | H | -isopropyl | — | 4-methane-sulfonamido-cyclohexyl | H | H | 1 | 1 | S | O | CF$_3$COOH |
| 85 | H | H | H | — | 1(morpholinocarbonyl)-4-piperidinyl | H | H | 1 | 1 | S | O | CF$_3$COOH |
| 86 | H | H | H | — | 1(methylsulphonyl)-4-piperidinyl | H | H | 1 | 1 | S | O | CF$_3$COOH |
| 87 | H | H | -isopropyl | — | 1(methylsulphonyl)-4-piperidinyl | H | H | 1 | 1 | S | O | CF$_3$COOH |
| 88 | H | H | -ethyl | — | 1(methylsulphonyl)-4-piperidinyl | H | H | 1 | 1 | S | O | CF$_3$COOH |
| 89 | H | H | -ethyl | — | 1(morpholinocarbonyl)-4-piperidinyl | H | H | 1 | 1 | S | O | CF$_3$COOH |
| 90 | H | H | H | — | 1(ethyl methyl aminocarbonyl)-4-piperidinyl | H | H | 1 | 1 | S | O | CF$_3$COOH |
| 91 | H | H | H | — | 1(4-methoxy benzene-sulphonyl)-4-piperidinyl | H | H | 1 | 1 | S | O | CF$_3$COOH |
| 92 | H | H | H | — | 4-(4-methoxy phenyl-sulfonamido)-cyclohexyl | H | H | 1 | 1 | S | O | CF$_3$COOH |
| 93 | H | H | H | — | 4-fluorobenzyl amino cyclohexyl | H | H | 1 | 1 | S | O | 2CF$_3$COOH |
| 94 | H | H | H | — | N-(4-fluoro benzyl) piperidine-4-yl | H | H | 1 | 1 | S | O | 2CF$_3$COOH |
| 95 | H | H | H | — | 1-[{5-chloro pyridin-2-yl carbamoyl}-methyl]-piperidine-4-yl | H | H | 1 | 1 | S | O | CF$_3$COOH |
| 96 | H | H | H | — | 1-trimethylacetamido cyclohexan-4-yl | H | H | 1 | 1 | S | O | CF$_3$COOH |
| 97 | H | H | C$_2$H$_5$ | — | 4-methyl sulfonamido cyclohexyl | H | H | 1 | 1 | S | O | — |
| 98 | H | H | H | — | 1-trimethylacetamido cyclohexan-4-yl | H | H | 1 | 1 | S | O | CF$_3$COOH |
| 99 | H | H | H | — | N-[{4-cyanophenyl Carbomoyl} Methyl]piperidin-4-yl | H | H | 1 | 1 | S | O | 2CF$_3$COOH |
| 100 | H | H | H | — | 4-[fluorophenyl carbomoyl]cyclohexyl | H | H | 1 | 1 | S | O | CF$_3$COOH |
| 101 | H | H | C$_2$H$_5$ | — | N-[{5-chloro Pyridin-2-yl Carbomoyl} methyl] piperidine-4-yl | H | H | 1 | 1 | S | O | 3HCl |
| 102 | H | H | H | — | 1-[(4-trifluromethyl-phenylcarbamoyl)-methyl]-piperidin-4-yl | H | H | 1 | 1 | —S— | O | 2CF$_3$COOH |
| 103 | H | H | H | — | 1-[(adamantan-1-yl-carbamoyl)-methyl]-piperidin-4-yl | H | H | 1 | 1 | —S— | O | 2CF$_3$COOH |
| 104 | H | H | H | — | 1-[(2,3-dihydro-benzo[1,4]dioxin-6-yl-carbamoyl)-methyl]-piperidin-4-yl | H | H | 1 | 1 | —S— | O | 2CF$_3$COOH |
| 105 | H | H | H | — | 1-[(4-chlorophenyl carbamoyl)-methyl]-piperidin-4-yl | H | H | 1 | 1 | —S— | O | 2CF$_3$COOH |
| 106 | H | H | H | — | 1-[(pyrimidin-2-yl-carbamoyl)-methyl]-piperidin-4-yl | H | H | 1 | 1 | —S— | O | 3CF$_3$COOH |
| 107 | H | H | H | — | 1-(2-morpholin-4yl-2-oxo-ethyl)-piperidin-4-yl | H | H | 1 | 1 | —S— | O | 2CF$_3$COOH |

TABLE 1-continued

Representative Compounds

| Comp No. | R1 | R2 | R3 | -R4–R6- | R4 | R5 | R6 | k | n | X | Z | Salt |
|---|---|---|---|---|---|---|---|---|---|---|---|---|
| 108 | H | H | H | — | 1-(cyclopropyl carbamoyl)-methyl-piperidin-4-yl | H | H | 1 | 1 | —S— | O | 2CF$_3$COOH |
| 109 | H | H | H | — | 1-(2'cyano-biphenyl-4-yl-methyl) piperidine-4-yl | H | H | 1 | 1 | —S— | O | 2CF$_3$COOH |
| 110 | H | H | H | — | 1-(morpholin-4-ylacetyl) piperidine-4-yl | H | H | 1 | 1 | —S— | O | 2CF$_3$COOH |
| 111 | H | H | H | — | 4-[{(5-chloropyridin-2-ylcarbomoyl)methyl}amino] cyclohex-1-yl | H | H | 1 | 1 | —S— | O | 3CF$_3$COOH |
| 112 | H | H | H | — | 4-[{(4-cyanophenylcarbamoyl)methyl}amino] cyclohex-1-yl | H | H | 1 | 1 | —S— | O | 2CF$_3$COOH |
| 113 | H | H | H | — | 4-[{(4-chlorophenylcarbamoyl)methyl}amino] cyclohex-1-yl | H | H | 1 | 1 | —S— | O | 2CF$_3$COOH |
| 114 | H | H | H | — | 4-methane-sulfonamido-cyclohex-1-yl | H | H | 1 | 1 | S | O | HCl |
| 115 | H | H | H | — | 1-[{5-chloro pyridin-2-yl carbamoyl}-methyl]-piperidine-4-yl | H | H | 1 | 1 | S | O | HCl |

*This is part of the cyclic structure -R4–R6-
**This compound is obtained by reacting with lower isomer obtained during the reduction step.
***This compound is obtained by reacting with the upper isomer obtained during the reduction step.
R2–R4 combine together to give —CH$_2$—CH$_2$—CH$_2$—CH$_2$—

The Representative Compounds of the Invention Listed in Table I can be Identified by Their Following Chemical Names:

(a) [2-Cyano-1-(piperazine-2-yl)-carbonyl pyrrolidine bis-trifluoroacetate] (Compound No. 1).
(b) [2-Cyano-1-(4-isopropyl-2-piperazinyl)-carbonyl-pyrrolidine bis trifluoroacetate] (Compound No. 2)
(c) 1-[1-Oxo-2-((1-phenyl)-hydrazino)]ethyl-2-cyano pyrrolidine trifluoroacetate (Compound No. 3)
(d) 1-[1-Oxo-2-(1-hydrazino)]ethyl-2-cyano pyrrolidine trifluoroacetate (Compound No. 4)
(e) 3-[1-Oxo-2-((2-(1,1-dimethyl ethyl oxy carbonyl))hydrazino)]ethyl-4-cyano thiazolidine (Compound No. 5)
(f) 1-[1-Oxo-2-((2-(1,1-dimethylethyloxy carbonyl))-1-phenyl hydrazino)]ethyl-2-cyano pyrrolidine (Compound No. 6)
(g) 1-[1-Oxo-2-((2-(1,1-dimethylethyl oxy carbonyl))hydrazino)]ethyl-2-cyano pyrrolidine (Compound No. 7).
(h) 1-[1-Oxo-2-((1-(4-nitrophenylmethyl))hydrazino)]ethyl-2-cyano pyrrolidine trifluoroacetate (Compound No. 8)
(i) 3-[1-Oxo-2-((1-phenyl)hydrazino)]ethyl-4-cyano thiazolidine trifluoroacetate (Compound No. 9)
(j) 1-[1-Oxo-2-(1-(2-methylpropyl)hydrazino)]ethyl-2-cyano pyrrolidine trifluoroacetate (Compound No. 10)
(k) 1-[1-Oxo-2-((1-phenylmethyl)hydrazino)]ethyl-2-cyano pyrrolidine trifluoroacetate (Compound No. 11)
(l) 1-[1-Oxo-2-((1-(1-methyl)ethyl)hydrazino)]ethyl-2-cyano pyrrolidine trifluoroacetate (Compound No. 12)
(m) 1-[1-Oxo-2-((2,2-diethyl)-hydrazino)]ethyl-2-cyano thiazolidine (Compound No. 13)
(n) 1-[1-Oxo-2-((1-ethyl)hydrazino)]ethyl-2-cyano pyrrolidine trifluoroacetate (Compound No. 14)
(o) 3-[1-Oxo-2-(1-hydrazino)]ethyl-4-cyano thiazolidine trifluoroacetate (Compound No. 15)
(p) 3-[1-Oxo-2-((1-phenylmethyl)hydrazino)]ethyl-4-cyano thiazolidine trifluoroacetate (Compound No. 16)
(q) 3-[1-Oxo-2-((1-(4-nitrophenylmethyl))hydrazino)]ethyl-4-cyano thiazolidine trifluoroacetate (Compound No. 17)
(r) 1-[1-Oxo-2-((1-Cyclopentyl)-hydrazino)]ethyl-2-cyano pyrrolidine trifluoroacetate (Compound No. 18)
(s) 3-[1-Oxo-2-((1-Cyclopentyl)-hydrazino)]ethyl-4-cyano thiazolidine trifluoroacetate (Compound No. 19)
(t) 1-[1-Oxo-2-((1-Cyclohexyl)-hydrazino)]ethyl-2-cyano pyrrolidine trifluoroacetate (Compound No. 20)
(u) 3-[1-Oxo-2-((1-Cyclohexyl)-hydrazino)]ethyl-4-cyano thiazolidine trifluoroacetate (Compound No. 21)
(v) 1-[1-Oxo-2-((1-methylpropyl)hydrazino)]ethyl-2-cyano pyrrolidine trifluoroacetate (Compound No. 22)
(w) 3-[1-Oxo-2-((1-methylpropyl)hydrazino)]ethyl-2-cyano thiazolidine trifluoroacetate (Compound No. 23)
(x) 1-[1-Oxo-2-((1-Phenyl sulphonyl)hydrazino)]ethyl-2-cyano pyrrolidine trifluoroacetate (Compound No. 24)
(y) 3-[1-Oxo-2-((1-(4-methyl)cyclohexyl)hydrazino)]ethyl-4-cyano thiazolidine trifluoroacetate (Compound No. 25).
(z) 1-[1-Oxo-2-((4-Methyl)cyclohexyl)hydrazino)]ethyl-2-cyano pyrrolidine trifluoroacetate (Compound No. 26)
(aa) 1-[1-Oxo-2-(1-(2-Pyridyl)-hydrazino)]ethyl-2-cyano pyrrolidine bis-trifluoroacetate (Compound No. 27).
ab) 3-[1-Oxo-2-((1-Cycloheptyl)-hydrazino)]ethyl-4-cyano thiazolidine-trifluoroacetate (Compound No. 28)
ac) 3-[1-Oxo-2-((1-(4-methyl)cyclohexyl)-hydrazino)]ethyl-4-cyano thiazolidine trifluoroacetate (Compound No. 29)
ad) 1-[1-Oxo-2-((1-Cycloheptyl)-hydrazino)]ethyl-2-cyano pyrrolidine trifluoroacetate (Compound No. 30)
ae) [4-Cyano-3-(1-isopropylhydrazino)carbonyl thiazolidine hydrochloride] (Compound No. 31)
af) [2-Cyano-1-(1-cyclohexyl hydrazino)carbonyl pyrrolidine hydrochloride] (Compound No. 32)

ag) [4-Cyano-3-(1-cyclohexylhydrazino)carbonyl thiazolidine hydrochloride] (Compound No. 33)
ah) 1-[1-Oxo-2-(2-cyclohexyl)hydrazino]ethyl-2-cyanopyrrolidine trifluoroacetate (Compound No. 34)
ai) [4-Cyano-3-(1-phenyl hydrazino)carbonyl thiazolidine trifluoroacetate] (Compound No. 35
aj) 3-[1-Oxo-2-(1-cyclohexyl-2-isopropyl)hydrazino]ethyl-4-cyanothiazolidine hydrochloride (Compound No. 36)
ak) 1-[1-Oxo-2-(4-methylcyclohexyl)hydrazino]ethyl-2-cyanopyrrolidine trifluoroacetate (Compound No. 37)
al) 1-[1-Oxo-2-(1-cyclohexyl-2-isopropyl)hydrazino]ethyl-2-cyano pyrrolidine (Compound No. 38)
am) 1-[1-Oxo-2-(1-(4-methylcyclohexylmethyl)hydrazino)]ethyl-2-cyanopyrrolidine trifluoroacetate (Compound No. 39)
an) 1-[1-Oxo-2-(4-chlorophenyl)hydrazino]ethyl-2-cyanopyrrolidine trifluoroacetate (Compound No. 40)
ao) 1-[1-Oxo-2-isopropyl-2-hydrazino]ethyl-2-cyano pyrrolidine trifluoroacetate (Compound No. 41)
ap) 3-[1-Oxo-2-(1-(4-methylcyclohexyl)-2-ethyl)hydrazino]ethyl-4-cyanothiazolidine trifluoroacetate (Compound No. 42)
aq) 3-[1-Oxo-2-(1-(4-morpholinocarbonyl)hydrazino)ethyl]-4-cyanothiazolidine trifluoroacetate (Compound No. 43)
ar) 3-[1-Oxo-2-(1-(4-methylcyclohexyl)-2-isopropyl)hydrazino]ethyl-4-cyanothiazolidine trifluoroacetate (Compound No. 44)
as) 1-[1-Oxo-2-[(1-cyclohexyl)-2-(2-cyano-1-pyrrolidino acetyl)]hydrazino]ethyl-2-cyanopyrrolidine trifluoroacetate (Compound No. 45)
at) 3-[1-Oxo-2-(1,2-bis-(2-(2-pyridyl)ethylaminocarbonyl)hydrazino)]ethyl-4-cyano thiazolidine bis trifluoroacetate (Compound No. 46)
au) 3-[1-Oxo-2-(1-(4-tert-butyl cyclohexyl)hydrazino)]ethyl-4-cyanothiazolidine trifluoro acetate (Compound No. 47)
av) 1-[1-Oxo-2-(1-tetralinyl)hydrazino]ethyl-2-cyanopyrrolidine trifluoroacetate (Compound No. 48)
aw) 3-[1-Oxo-2-(1-(4-tertbutylcyclohexyl)hydrazino)]ethyl-4-cyanothiazolidine trifluoroacetate (Compound No. 49)
ax) 1-[1-Oxo-2-(1-cyclohexyl)-2-(4-cyano-3-thiazolidino acetyl)]hydrazino]ethyl-2-cyano pyrrolidine (Compound No. 50)
ay) 3-[1-Oxo-2-(1-isopropyl-4-piperidinyl)hydrazino)]ethyl-4-cyano thiazolidine trifluoroacetate (Compound No. 51)
az) 3-[1-Oxo-2-(1-(4-cyanophenylmethyl)-piperidin-4-yl)hydrazino)]ethyl-4-cyanothiazolidine bis trifluoroacetate (Compound No. 52)
ba) 3-[1-Oxo-2-[1-(4-methylcyclohexyl)-2-(3-pyridinylmethyl)-4-piperidinyl)]hydrazino]ethyl-4-cyanothiazolidine (Compound No. 53)
(bb) 3-[1-Oxo-2-[1-(4-methylcyclohexyl)-2-(1-isopropyl-4-piperidinyl)]hydrazino]ethyl-4-cyanothiazolidine (Compound No. 54)
bc) 3-[1-Oxo-2-(1-(1-(4-methylphenylsulphonyl)-4-piperidinyl)-hydrazino)]ethyl-4-cyanothiazolidine trifluoroacetate (Compound No. 55)
bd) 3-[1-Oxo-2-[1-methyl-2-(1-(4-methylphenylsulphonyl)-piperidin-4-yl)]hydrazino]ethyl-4-cyanothiazolidine trifluoroacetate (Compound No. 56)
be) 3-[1-Oxo-2-(1-(1-(3-pyridinemethyl)-4-piperidinyl)hydrazino)]ethyl-4-cyanothiazolidine tris trifluoroacetate (Compound No. 57)
bf) 3-[1-Oxo-2-[1-methyl-2-(1-(4-cyanophenylmethyl)piperidin-4-yl)]hydrazino]ethyl-4-cyanothiazolidine bis trifluoroacetate (Compound No. 58)
bg) 3-[1-Oxo-2-[1-methyl-2-(1-(3-pyridinylmethyl)-piperidin-4-yl)]hydrazino]ethyl-4-cyanothiazolidine tris trifluoroacetate (Compound No. 59)
bh) 3-[1-Oxo-2-(1-(4-n propylcyclohexyl)hydrazino)]ethyl-4-cyanothiazolidine trifluoro acetate (Compound No. 60)
bi) 3-[1-Oxo-2-(1-(1-(4-nitrophenylmethyl)-piperidin-4-yl)hydrazino]ethyl-4-cyanothiazolidine trifluoroacetate (Compound No. 61)
bj) 3-[1-Oxo-2-[1-(1-(4-chlorophenylsulphonyl)-piperidin-4-yl)]hydrazino]ethyl-4-cyanothiazolidine trifluoroacetate (Compound No. 62)
bk) 3-[1-Oxo-2-(1-(1-norcamphoranyl)hydrazino)]ethyl-4-cyanothiazolidine trifluoroacetate (Compound No. 63)
bl) 3-[1-Oxo-2-(1-(4-n propylcyclohexyl)hydrazino)]ethyl-4-cyanothiazolidine trifluoroacetate (Compound No. 64)
bm) 3-[1-Oxo-2-[1-(1-(4-methylcyclohexyl carbonyl)-piperidin-4-yl)]hydrazino]ethyl-4-cyanothiazolidine trifluoroacetate (Compound No. 65)
bn) 3-[1-Oxo-2-(1-(1-acetyl)-piperidin-4-yl)hydrazino]ethyl-4-cyanothiazolidine trifluoroacetate (Compound No. 66)
bo) 1,1-Dioxo-3-[1-oxo-2-(1-(4-methylcyclohexyl)hydrazino)]ethyl-4-cyanothiazolidine trifluoroacetate (Compound No. 67)
bp) 3-[1-Oxo-2-(1-methyl-2-(4-methylcyclohexyl)hydrazino)]ethyl-4-cyanothiazolidine (Compound No. 68)
bq) 3-[1-Oxo-2-(1-methyl-2-(4-methylcyclohexyl)hydrazino)]ethyl-4-cyanothiazolidine (Compound No. 69)
br) 3-[1-Oxo-2-(1-(1-(2,3-dichlorophenyl carbonyl)-piperidin-4-yl)hydrazino)]ethyl-4-cyanothiazolidine trifluoroacetate (Compound No. 70)
bs) 3-[1-Oxo-2-[1-methyl-2-(1-(4-chlorophenylsulphonyl)-piperidin-4-yl)]-hydrazino]ethyl-4-cyanothiazolidine (Compound No. 71)
bt) 3-[1-Oxo-2-(1-(4-piperidinyl)hydrazino)]ethyl-4-cyanothiazolidine bis trifluoroacetate (Compound No. 72)
bu) [1-Oxo-2-(1-(1-(4-chlorophenylsulphonyl)-piperdin-4-yl)-hydrazino)]ethyl-2-cyanopyrrolidine trifluoroacetate (Compound No. 73)
bv) 3-[1-Oxo-2-(1-(4-methylcyclohexyl)-2-acetyl)hydrazino]ethyl-4-cyanothiazolidine (Compound No. 74)
bw) 3-[1-Oxo-2-(1-(1-adamantanyl)hydrazino)]ethyl-4-cyanothiazolidine trifluoroacetate (Compound No. 75)
bx) 3-[1-Oxo-2-(1-(1-(tert-butyl carbonyl)-piperidin-4-yl)hydrazino)]ethyl-4-cyanothiazolidine trifluoroacetate (Compound No. 76)
by) 3-[1-Oxo-2-(1-(1-(5-trifluoromethyl-2-pyridinyl)-piperidin-4-yl)hydrazino)]ethyl-4-cyano thiazolidine bis trifluoroacetate (Compound No. 77)
bz) 3-[1-Oxo-2-(1-(1-methanesulphonylamino-4-cyclohexyl)hydrazino)]ethyl-4-cyanothiazolidine trifluoroacetate (Compound No. 78)
ca) 3-[1-Oxo-2-(1-(3,3,5-trimethyl cyclohexyl)-hydrazino)]ethyl-4-cyanothiazolidine trifluoroacetate (Compound No. 79)
cb) 3-[1-Oxo-2-(1-isopropyl-2-ethyl)-hydrazino]-ethyl-4-cyanothiazolidine trifluoroacetate (Compound No. 80)
(cc) 3-[1-Oxo-2-[1-(1-phenylmethyl-piperidin-4-yl)]-hydrazino]-ethyl-4-cyanothiazolidine trifluoroacetate (Compound No. 81)
cd) 3-[1-Oxo-2-(1-(4-chlorophenyl sulphonylamino-4-cyclohexyl)hydrazino)]ethyl-4-cyanothiazolidine trifluoroacetate (Compound No. 82)

ce) 3-[1-Oxo-2-(pyridazin-1-yl)]ethyl-4-cyanothiazolidine (Compound No. 83)

cf) 3-[1-Oxo-2-(1-(1-methanesulphonylamino-4-cyclohexyl)-2-isopropyl)hydrazino]ethyl-4-cyanothiazolidine trifluoroacetate (Compound No. 84)

cg) 3-[1-oxo-2-[1-(1(morpholinocarbonyl)-piperidin-4-yl)]hydrazino]ethyl-4-cyano-thiazolidine trifluoroacetate (Compound No. 85)

ch) 3-[1-oxo-2-[1-(1-(methylsulphonyl)-piperidin-4-yl)]hydrazino]ethyl-4-cyanothiazolidine trifluoroacetate (Compound No. 86)

ci) 3-[1-oxo-2-[1-(1-(methylsulphonyl)-piperidin-4-yl)-2-isopropyl]hydrazino]ethyl-4-cyanothiazolidine trifluoroacetate (Compound No. 87)

cj) 3-[1-oxo-2-[1-(1-(methylsulphonyl)-piperidin-4-yl)-2-ethyl]hydrazino]ethyl-4-cyanothiazolidine trifluoroacetate (Compound No. 88)

ck) 3-[1-oxo-2-[1-(1-(morpholinocarbonyl)-piperidin-4-yl)-2-ethyl]hydrazino]ethyl-4-cyanothiazolidine trifluoroacetate (Compound No. 89)

cl) 3-[1-oxo-2-[1-(1-(N-ethylmethylaminocarbonyl)-piperidin-4-yl)]hydrazino]ethyl-4-cyanothiazolidine trifluoroacetate (Compound No. 90)

cm) 3-[1-oxo-2-[1-(1-(4-methoxyphenylsulphonyl)-piperidin-4-yl)]hydrazino]ethyl-4cyanothiazolidine trifluoroacetate (Compound No. 91)

cn) 3-[1-oxo-2-[1-(1-(4-methoxyphenylsulphonyl)aminocyclohexan-4-yl)]hydrazino]ethyl-4-cyanothiazolidine trifluoroacetate (Compound No. 92)

co) 3-[1-oxo-2-[1-(1-(4-fluorobenzyl)aminocyclohexan-4-yl)]hydrazino]ethyl-4-cyanothiazolidine bis-trifluoroacetate (Compound No. 93)

cp) 3-[1-oxo-2-[1-(1-(4-fluorobenzyl)-piperidin-4-yl)]hydrazino]ethyl-4-cyanothiazolidine bis-trifluoroacetate (Compound No. 94)

cq) 3-[1-oxo-2-[(1-(1-(2-oxo-2-(5-chloropyridin-2-yl)aminoethyl)piperidin-4-yl)]hydrazino]ethyl-4-cyanothiazolidine tris-trifluoroacetate (Compound No. 95)

cr) 3-[1-oxo-2-[1-(1-(trimethyl acetamido)cyclohexan-4-yl)]hydrazino]ethyl-4-cyanothiazolidine trifluoroacetate (Compound No. 96)

cs) 3-[1-oxo-2-[1-(1-(methanesulphonyl)aminocyclohexan-4-yl)-2-ethyl]hydrazino]ethyl-4-cyanothiazolidine (Compound No. 97)

ct) 3-[1-oxo-2-[(1-(trimethyl acetamido)cyclohexan-4-yl)]hydrazino]ethyl-4-cyanothiazolidine trifluoroacetate (Compound No. 98)

cu) 3-[1-oxo-2-[1-(1-(2-oxo-2-(4-cyanophenyl)aminoethyl)piperidin-4-yl)]hydrazino]ethyl-4-cyanothiazolidine bis-trifluoroacetate (Compound No. 99)

cv) 3-[1-oxo-2-[1-(4-fluorobenzoyl)aminocyclohexan-4-yl)]hydrazino]ethyl-4-cyanothiazolidine trifluoroacetate (Compound No. 100) cw) 3-[1-oxo-2-[1-(1-(2-oxo-2-(5-chloropyridin-2-yl)aminoethyl)piperidin-4-yl)ethylhydrazino]ethyl-4-cyanothiazolidine tris-hydrochloride (Compound No. 101)

cx) 3-[1-oxo-2-[-1-(1-(2-oxo-2-(4-trifluorophenyl)aminoethyl)piperidin-4-yl)]hydrazino]ethyl-4-cyanothiazolidine bis-trifluoroacetate (Compound No. 102)

cy) 3-[1-oxo-2-[1-(1-(2-oxo-2(-adamant-1-yl)amino ethyl)piperidin-4-yl)]hydrazino]ethyl-4-cyanothiazolidine bis-trifluoroacetate (Compound No. 103)

cz) 3-[1-oxo-2-[1-(1-(2-oxo-2(2,3-dihydrobenzo(1,4)dioxan-6-yl)aminoethyl)piperidin-4-yl)]hydrazino]ethyl-4-cyano-thiazolidine bis-trifluoroacetate (Compound No. 104)

da) 3-[1-oxo-2-[1-(1-(2-oxo-2(4-chlorophenyl)aminoethyl)piperidin-4-yl)]hydrazino]ethyl-4-cyanothiazolidine bis-trifluoroacetate (Compound No. 105)

db) 3[2-oxo-2-[1-(1-(2-oxo-2(pyrimidin-2-yl)aminoethyl)piperidin-4-yl)]hydrazino]ethyl-4-cyanothiazolidine tris-trifluoroacetate (Compound No. 106)

dc) 3-[1-oxo-2-[1-(1-(-2-oxo-2(morpholin-4-yl)ethyl)piperidin-4-yl)]hydrazino]ethyl-4-cyanothiazolidine bis-trifluoroacetate (Compound No. 107)

(dd) 3[1-oxo-2-[1-(1-(2-oxo-2-(cyclopropyl)aminoethyl)piperidin-4-yl)]hydrazino]ethyl-4-cyanothiazolidine bis-trifluoroacetate (Compound No. 108)

de) 3-[1-oxo-2-[1-(1-(2-cyanobiphenyl-4-yl)methyl)piperidine-4-yl]hydrazino]ethyl-4-cyanothiazolidine bis-trifluoroacetate (Compound No. 109)

df) 3-[1-oxo-2-[1-(1-(1-oxo-2-(morpholin-4-yl)ethyl)piperidin-4-yl)]hydrazino]ethyl-4-cyanothiazolidine bis-trifluoroacetate (Compound No. 110)

dg) 3-[1-oxo-2-[1-(4-(2-oxo-2-(5-chloropyridin-2-yl)aminoethyl)amino cyclohex-1yl)]hydrazino]ethyl-4-cyanothiazolidine tris-trifluoroacetate (Compound No. 111)

dh) 3-[1-oxo-2-[1-(4-(2-oxo-2-(4-cyanophenyl)aminoethyl)aminocyclohex-1-yl)]hydrazino]ethyl-4-cyanothiazolidine bis-trifluoroacetate (Compound No. 112)

di) 3-[1-oxo-2-[1-(4-(2-oxo-2-(4-chlorophenyl)aminoethyl)aminocyclohex-1-yl)]hydrazino]ethyl-4-cyanothiazolidine bis-trifluoroacetate (Compound No. 113)

dj) 3-[1-oxo-2-(1-(1-methanesulphonylamino-4-cyclohexyl)hydrazino)]ethyl-4-cyanothiazolidine hydrochloride (Compound No. 114)

dk) 3-[-1-oxo-2-[1-(1-(-2-oxo-2-(5-chloropyridin-2-yl)aminoethyl)piperidine-4yl)]hydrazino]ethyl-4-cyanothiazolidine trihydrochloride (Compound No. 115)

Assay of DPP-IV Enzyme Inhibitory Activity.

The assay method is a modified method (as described by Welch et al, 1998) based on spectrophotometric determination of the product formed by penultimate proline cleaving activity of the enzyme.

The following equation explains the principle of the assay method:

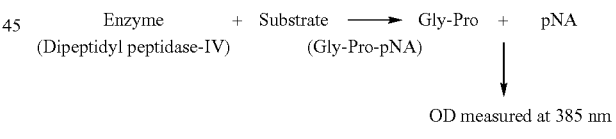

Gly-Pro-pNA: Glycine-Proline-p-nitroanilide

Assay protocol involves incubation of the enzyme dipeptidyl peptidase IV with the test substance at 30° C. for 30 min followed by addition of this reaction mixture to the substrate Gly-Pro-pNA that was equilibrated at 30° C. for 2 min. The enzyme cleaves the substrate at penultimate proline and releases p-nitroanilide, the optical density of which is measured at 385 nm. The formation of p-nitroanilide will be reduced in the presence of inhibitor. Optical density is measured for 2 hours for every 10 min using a spectrophotometer and $V_{max}$ is calculated to find the activity of new chemical entities. The activity of molecule is expressed in terms of % inhibition. At least three different concentrations were tried out for each of the test substances. The percentage inhibitions for each of the concentrations were plotted and an $IC_{50}$ of the test compound was worked out. The enzyme inhibitory activity of different test compounds were compared based on the IC$_{50}$ values.

The percentage inhibition % I, is calculated using the formula:

% $I=[(1-v_i/v_0)]*100$ where $v_1$ and $v_0$ are the $V_{max}$ values with and without the test substance, respectively.

Reagents and Their Preparation:
Substrate solution: 0.5 mM in 45 mM phosphate buffer
Substrate used: Gly-Pro-p-nitroanilide (Source: Sigma-Aldrich Co. Germany)
M. Wt of Gly-Pro-p-nitroanilide=328.8

3.288 mg substrate in 1 ml 45 mM phosphate buffer was prepared as stock solution. 0.25 ml of this stock solution was diluted to 5 ml to get 0.5 mM substrate solution (90 µl to be added in each well). The stock solution of the substrate was used within three days of preparation.

Enzyme solution: Porcine DPP-IV (Sigma-Aldrich Germany) was used throughout the study. 0.4 mU in 80 µl of Tris. HCl buffer was prepared. Fresh solutions were prepared everyday for the assays.

Inhibitor Solution:

The compounds of the present invention were dissolved in their respective vehicles.
E.g. 1. Compound No. 95 (in MilliQ water)
Mol. Wt. of Compound No. 95: 779

Various concentrations of inhibitor were used: 0.391 µM, 0.781 µM, and 3.125 µM. Solutions of inhibitor were prepared and used on the same day.

Experimental Procedure:

Different concentrations of inhibitor (compound 95), vehicle, substrate and enzyme were prepared as per standard procedures. 280 µl of enzyme solution (0.4-mU/80 µl in Tris HCl buffer) was added to the eppendorf containing 70 µl solution of inhibitor or vehicle and mixed. This reaction mixture was incubated for 30 min at 30° C. The 96 well plate containing substrate solution was thermally equilibrated in the spectrophotometer for 2 min at 30° C. Later 100 µl of the enzyme-inhibitor pre-incubation solution was added to respective wells in a 96 well plate. Each concentration-of the inhibitor was tested in triplicates.

The rate of change in UV absorbance (in presence of various concentrations of the inhibitor) was measured at 385 nm, with respect to wells containing only 0.5 mM substrate in 45 mM phosphate buffer as blank at every 10 min for 2 hours after adding enzyme-inhibitor mixture to wells containing substrate solution.

TABLE 2

The inhibitory activity of the compounds on DPP-IV enzyme activity

| Compound No. | IC$_{50}$ (µM) Mean ± SD |
|---|---|
| 1 | 47.56 ± 2.72 |
| 3 | 34.11 ± 4.57 |
| 4 | 88.60 ± 18.05 |
| 9 | 6.18 ± 0.88 |
| 10 | 69.84 ± 17.48 |
| 12 | 61.29 ± 4.55 |
| 13 | 57.05 ± 3.76 |
| 14 | 93.72 ± 5.54 |
| 15 | 41.92 ± 11.56 |
| 16 | 9.29 ± 0.64 |
| 17 | 35.80 ± 1.03 |
| 18 | 32.07 ± 1.65 |

TABLE 2-continued

The inhibitory activity of the compounds on DPP-IV enzyme activity

| Compound No. | IC$_{50}$ (µM) Mean ± SD |
|---|---|
| 19 | 1.46 ± 0.16 |
| 20 | 33.71 ± 0.99 |
| 21 | 2.01 ± 0.16 |
| 22 | 76.52 ± 7.51 |
| 23 | 2.94 ± 0.15 |
| 25 | 0.67 ± 0.03 |
| 26 | 10 ± 0.79 |
| 27 | 42.96 ± 2.76 |
| 28 | 2.29 ± 0.11 |
| 29 | 0.80 ± 0.15 |
| 30 | 35.07 ± 2.66 |
| 34 | 30.31 ± 5.50 |
| 36 | 23.33 ± 2.54 |
| 37 | 28.26 ± 4.60 |
| 38 | 96.90 ± 23.03 |
| 39 | 50.42 ± 4.59 |
| 41 | 48.27 ± 1.75 |
| 42 | 0.53 ± 0.09 |
| 43 | 38.18 ± 2.56 |
| 44 | 2.86 ± 0.18 |
| 45 | 43.99 ± 1.92 |
| 46 | 78.62 ± 4.58 |
| 47 | 1.14 ± 0.09 |
| 48 | 45.18 ± 1.21 |
| 49 | 1.04 ± 0.25 |
| 50 | 60.06 ± 5.50 |
| 51 | 3.50 ± 0.06 |
| 52 | 0.71 ± 0.06 |
| 53 | 16.74 ± 2.07 |
| 54 | 6.43 ± 0.15 |
| 55 | 2.70 ± 0.16 |
| 56 | 44.23 ± 1.36 |
| 57 | 4.77 ± 0.41 |
| 58 | 17.07 ± 0.30 |
| 59 | 9.27 ± 0.42 |
| 60 | 0.69 ± 0.03 |
| 61 | 0.70 ± 0.03 |
| 62 | 1.54 ± 0.34 |
| 63 | 0.73 ± 0.02 |
| 64 | 0.34 ± 0.07 |
| 65 | 0.87 ± 0.06 |
| 66 | 1.53 ± 0.01 |
| 67 | 72.49 ± 7.05 |
| 68 | 45.26 ± 3.03 |
| 69 | 68.99 ± 10.07 |
| 70 | 1.79 ± 0.12 |
| 71 | 86.16 ± 5.30 |
| 72 | 12.08 ± 0.13 |
| 73 | 48.87 ± 1.81 |
| 74 | 97.74 ± 13.12 |
| 75 | 0.31 ± 0.05 |
| 76 | 4.15 ± 0.29 |
| 77 | 0.67 ± 0.06 |
| 78 | 0.25 ± 0.02 |
| 79 | 0.92 ± 0.03 |
| 80 | 2.27 ± 0.19 |
| 81 | 1.63 ± 0.15 |
| 82 | 0.66 ± 0.10 |
| 83 | 81.97 ± 18.04 |
| 84 | 5.78 ± 0.18 |
| 85 | 0.79 ± 0.072 |
| 86 | 1.46 ± 0.22 |
| 87 | 18.26 ± 3.2 |
| 88 | 3.755 ± 0.101 |
| 89 | 0.985 ± 0.086 |
| 90 | 1.23 ± 0.3 |
| 91 | 6.7 ± 0.4 |
| 92 | 1.33 ± 0.124 |
| 93 | 5.56 ± 0.18 |
| 94 | 2.23 ± 0.08 |
| 95 | 0.12 ± 0.013 |
| 96 | 4.0 ± 0.144 |
| 97 | 1.03 ± 0.07 |
| 98 | 0.71 ± 0.01 |

TABLE 2-continued

The inhibitory activity of the compounds on DPP-IV enzyme activity

| Compound No. | IC$_{50}$ (μM) Mean ± SD |
|---|---|
| 99 | 0.2 ± 0.04 |
| 100 | 0.93 ± 0.015 |
| 101 | 0.488 ± 0.017 |
| 102 | 0.308 ± 0.06 |
| 103 | 0.523 ± 0.017 |
| 104 | 0.222 ± 0.023 |
| 105 | 0.258 ± 0.027 |
| 106 | 0.143 ± 0.02 |
| 107 | 0.525 ± 0.098 |
| 108 | 0.236 ± 0.025 |
| 109 | 1.022 ± 0.14 |
| 110 | 0.830 ± 0.05 |
| 111 | 0.563 ± 0.077 |
| 112 | 1.471 ± 0.07 |
| 113 | 1.065 ± 0.3 |
| 114 | 0.397 ± 0.02 |
| 115 | 0.088 ± 0.006 |

(Values are mean ± SD of three.experiments)

Note: The IC$_{50}$ values for compounds 1–32 as reported in the provisional specification No. 60/370,224, which is incorporated in the instant patent application by reference, were subjected to same experimental procedure as reported here to determine IC50 values. However, in view of an erroneous dilution factor taken for calculation of IC50 values in the provisional specification, the reported figures, though showing the same trend of activity are 9.5 times of the figures reported above for the compounds 1,3,4,9,10,12–23 and 25–30 recalculated by using the correct dilution factor.

Invivo Oral Glucose Tolerance Studies

The anti-hyperglycemic effect of compound no. 95 (8 mg/ml/kg, i.v) after an oral glucose load of 1 gm/kg was studied in STZ induced diabetic rats (modified method of Balkan et al 1999).

Animals: Male STZ induced diabetic rats aged 10–12 weeks and weighing between 200–250 gm were used for the study. These rats were treated with streptozotocin administered intraperitoneally on the day of birth at a dose of 90 mg/kg. They were maintained under standard conditions till the age of 10–12 weeks when they were used for the study.

Materials: Glucose solution (1 gm/4 ml of saline), Diethyl ether compound no. 95 (8 mg/ml/kg), vehicle (1 ml/kg), Heparinized saline (100 IU/ml), glucometer and strips.

Method: Animals were divided into two groups.

Group I: 8 hours fasted rats were treated with compound no. 95 vehicle (1 ml/kg, i.v.) 5 min before administration of glucose load.

Group II: 8 hours fasted rats were treated with compound no. 95 (8 mg/ml/kg, i.v) 5 min before administration of glucose load.

In both groups, blood samples were taken before administration of vehicle/compound no. 95 and glucose load for blood glucose estimation. Blood glucose level before administration of compound no. 95 or its vehicle was considered as –5 min reading. Blood glucose level before administration of glucose was considered as 0 min reading.

After 10, 20, 30, 45, 60, 75, 90, 120, 150 and 180 min of glucose administration, blood glucose level was estimated by the glucose oxidase method using a LifeScan glucometer (Ca, USA). Blood glucose level at various time points was subtracted from the basal (0 min) reading. This was done to avoid changes in AUC because of variation in basal glucose level. The glucose excursion at various time points was plotted against time and the AUC was calculated.

The activity of compound no. 95 was expressed as % reduction in AUC as compared with that of its vehicle.

Results:

The AUC for the group treated with compound no. 95 was found to be 413.3±134.6 mM*min and the AUC for the group treated with vehicle for compound no. 95 was found to be 1070.5±342.4 mM*min. compound no. 95 significantly (p<0.05) reduced the AUC values as compared to the group treated with their corresponding vehicle.

Table A: Effect of compound no. 95 on AUC of glucose excursion in nSTZ induced diabetic rats.

TABLE A

| GROUP (n) | DOSE | AUC values mM * min |
|---|---|---|
| compound no. 95 (7) | 8 mg/ml/kg | 413.3 ± 134.6a |
| Vehicle for (compound no. 95) (5) | 1 ml/kg | 1070.5 ± 342.4 |

Values of AUC are Mean ± SD
a = P < 0.05 vs Vehicle for compound no. 95 group

Table B: Effect of compound no. 95 (8 mg/ml/kg; i.v) pre-treatment on glucose excursions after a 1 gm/kg glucose load in nSTZ induced diabetic rats

TABLE B

| | Glucose excursions after a 1 gm/kg glucose load | |
|---|---|---|
| TIME | compound no. 95 (n = 7) | Vehicle for compound no. 95 (n = 5) |
| 0 | 0.0 | 0.0 |
| 10 | 3.9 | 2.7 |
| 20 | 5.9 | 5.2 |
| 30 | 7.8 | 7.8 |
| 45 | 6.2 | 8.0 |
| 60 | 4.1 | 8.8 |
| 75 | 2.7 | 7.9 |
| 90 | 0.5 | 7.4 |
| 120 | −2.8 | 5.4 |
| 150 | −4.1 | 4.5 |
| 180 | −3.9 | 3.9 |

The results of the above analysis are also depicted in FIG. 1 and FIG. 2 of the drawings.

Free Radical Scavenging Activity:

1. Aim:

To determine the in-vitro free radical scavenging activity of compounds of general formula-I on 2,2,-diphenyl-1-picrylhydrazyl (DPPH) radical (Ref: W. Brand-Williams, M. E. Cuvelier, C. Berset "Use of a free radical method to evaluate antioxidant activity ", Lebensm.—Wiss.u.Technol., 1995,28, Nr.1:25–30).

2. Principle Involved:

To evaluate the free radical scavenging activity of compounds they are allowed to react with stable radical DPPH*. In its radical form, DPPH* absorbed at the characteristic wave length of 515 nm, but upon reduction by an antioxidant or radical scavenger (AH), the absorption disappears.

Equation:

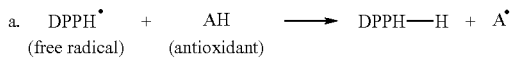

a. DPPH• + AH → DPPH—H + A•
   (free radical)   (antioxidant)

3. Reagents and Chemicals:
DPPH* (Sigma Aldrich)
Methanol (Merck)

4. Instrument Used:
UV-visible spectrophotometer (Jasco)
Quartz Microcuvette (1 ml capacity)

5. Procedure:
Preparation of DPPH* Solution:
$10^{-4}$ M solution of DPPH* was prepared in methanol.
Preparation of Drug Solution:
Various concentrations (10 mM, 1 mM, 0.5 mM, 0.25 mM and 0.125 mM) of drug solutions were prepared in methanol.
Preparation of Control Solution:
900 μl of DPPH* radical solution was added to an eppendorf tube. To it was added 100 μl of methanol.
Preparation of Test Solution:
900 μl of DPPH* radical solution was added to an eppendorf tube. To it was added 100 μl of various concentrations of drug solutions in methanol.
Measurement of Absorbance (O.D):
The absorbance of control and test samples was recorded after incubation at 30° C. for 30 minutes, at 515 nm taking methanol as blank.

6. Calculation:
The percent antioxidant activity was calculated according to the formula:

% Antioxidant activity=100−[O.D of test sample/ O.D of control*100]

TABLE 3

IN-VITRO FREE RADICAL SCAVENGING ACTIVITY OF THE MOLECULES USING DPPH FREE RADICAL

| Control/Compound No. | Concentration (μM) | % Activity |
|---|---|---|
| ASCORBIC ACID (Control) | 12.5 | 28.01 |
|  | 25 | 54.10 |
|  | 50 | 95.31 |
|  | 100 | 96.18 |
| 25 | 100 | 95.66 |
| 19 | 100 | 94.55 |
| 21 | 100 | 95.71 |
| 29 | 100 | 93.70 |
| 85 | 12.5 | 15.25 |
|  | 25 | 30.67 |
|  | 50 | 49.97 |
|  | 100 | 67.23 |
| 86 | 12.5 | 22.72 |
|  | 25 | 45.27 |
|  | 50 | 70.18 |
|  | 100 | 88.14 |
| 87 | 12.5 | 12.87 |
|  | 25 | 30.88 |
|  | 50 | 44.03 |
|  | 100 | 55.94 |
| 88 | 12.5 | 14.49 |
|  | 25 | 44.12 |
|  | 50 | 56.11 |
|  | 100 | 69.34 |

TABLE 3-continued

IN-VITRO FREE RADICAL SCAVENGING ACTIVITY OF THE MOLECULES USING DPPH FREE RADICAL

| Control/Compound No. | Concentration (μM) | % Activity |
|---|---|---|
| 89 | 12.5 | 10.37 |
|  | 25 | 20.74 |
|  | 50 | 36.94 |
|  | 100 | 55.07 |
| 90 | 12.5 | 21.81 |
|  | 25 | 42.93 |
|  | 50 | 62.91 |
|  | 100 | 82.75 |
| 91 | 12.5 | 17.16 |
|  | 25 | 38.11 |
|  | 50 | 58.87 |
|  | 100 | 85.69 |
| 92 | 12.5 | 10.07 |
|  | 25 | 30.36 |
|  | 50 | 58.48 |
|  | 100 | 78.77 |
| 93 | 12.5 | 15.18 |
|  | 25 | 28.08 |
|  | 50 | 44.13 |
|  | 100 | 64.24 |
| 94 | 12.5 | 9.34 |
|  | 25 | 24.05 |
|  | 50 | 39.04 |
|  | 100 | 55.85 |
| 95 | 12.5 | 22.06 |
|  | 25 | 36.87 |
|  | 50 | 44.81 |
|  | 100 | 65.52 |
| 96 | 12.5 | 19.11 |
|  | 25 | 34.43 |
|  | 50 | 48.83 |
|  | 100 | 63.26 |
| 97 | 12.5 | 18.06 |
|  | 25 | 38.30 |
|  | 50 | 66.99 |
|  | 100 | 91.67 |
| 98 | 12.5 | 21.99 |
|  | 25 | 40.77 |
|  | 50 | 59.21 |
|  | 100 | 73.35 |
| 99 | 12.5 | 15.12 |
|  | 25 | 24.87 |
|  | 50 | 39.13 |
|  | 100 | 53.33 |
| 100 | 12.5 | 31.14 |
|  | 25 | 41.49 |
|  | 50 | 59.54 |
|  | 100 | 77.75 |
| 101 | 12.5 | 20.41 |
|  | 25 | 31.00 |
|  | 50 | 32.19 |
|  | 100 | 61.15 |
| 102 | 12.5 | 20.90 |
|  | 25 | 29.56 |
|  | 50 | 34.26 |
|  | 100 | 50.15 |
| 103 | 12.5 | 20.41 |
|  | 25 | 40.80 |
|  | 50 | 44.09 |
|  | 100 | 54.81 |
| 104 | 12.5 | 19.40 |
|  | 25 | 36.23 |
|  | 50 | 42.20 |
|  | 100 | 50.14 |
| 105 | 12.5 | 24.03 |
|  | 25 | 35.27 |
|  | 50 | 49.25 |
|  | 100 | 49.63 |
| 106 | 12.5 | 24.86 |
|  | 25 | 42.52 |
|  | 50 | 70.39 |
|  | 100 | 72.86 |

TABLE 3-continued

IN-VITRO FREE RADICAL SCAVENGING ACTIVITY
OF THE MOLECULES USING DPPH FREE RADICAL

| Control/Compound No. | Concentration (µM) | % Activity |
|---|---|---|
| 108 | 12.5 | 20.19 |
|  | 25 | 26.25 |
|  | 50 | 34.71 |
|  | 100 | 52.72 |
| 114 | 12.5 | 19.23 |
|  | 25 | 39.37 |
|  | 50 | 78.16 |
|  | 100 | 92.76 |
| 115 | 12.5 | 19.46 |
|  | 25 | 26.94 |
|  | 50 | 46.24 |
|  | 100 | 75.84 |

The test compounds listed in the Table 3 above exhibit invitro (antioxidant) free radical scavenging activity. Excessive production of free radicals; reactive oxygen species (ROS) results in oxidative stress. Therefore, these molecules would be very effective in reducing oxidative stress by their ability to trap ROS. Antioxidants (free radicals scavengers) are reported to be effective in the management of various diseases linked with oxidative stress.

Also, the novel compounds show Free Radical Scavenging Activity which is useful for (a) Neurodegenerative disorders such as Alzheimer's Disease, Parkinson's Disease, Huntington's Disease, Motor Neuron Disease, Prion Disease etc, (b) Diabetes and Diabetic Vascular Complications, (c) Intestinal Diseases such as Intestinal Ischemia, Radiation Enteritis, Inflammatory Bowel Disease, Gastric and Colorectal Cancers etc., (d) Liver Diseases such as Alcoholic Liver Disease, Chronic Hepatitis C etc., (e) Cancers such as Lung Cancer, Colorectal Cancer, Cervical Cancer, Breast Cancer, Malignant Melanoma etc., (f) Cardiac Diseases such as Atherosclerosis, Myocardial Infarction, Ischemic Stroke, Endothelial Dysfunction etc., (g) Opthalmic Disorders such as Cataract formation, Macular degeneration etc., (h) HIV Diseases, (i) Respiratory Diseases such as Chronic Obstructive Pulmonary Diseases, Asthma etc., (j) Renal Diseases such as Glomerulonephritis, Acute Renal Failure etc.

Discussion of Test Results:

Oral glucose tolerance test is one of the methods to test pre-diabetic or diabetic condition and to evaluate insulin secretagogues and/or releasers. Glucose level in the body is mainly controlled by insulin although many other factors contribute to insulin release. Administration of glucose by oral route will increase the glucose level in the blood, which induces the release of insulin. This glucose stimulated insulin release is impaired in diabetes. By pretreatment with drugs that releases or stimulates insulin release before taking food/glucose, the rise in glucose level can be controlled.

FIG. 2 and Table-2 show a distinct decrease in the compound no. 95 treated animal's blood glucose values as compared to the corresponding vehicle treated group. This is also reflected in the decrease in AUC of glucose in compound no. 95 treated group as compared to vehicle group. From the graphs shown in FIGS. 1 and 2 it is evident that compound no. 95 controls hyperglycemia and brings the glucose levels to normoglycemic range. Please note that the negative values do not represent hypoglycemia; it is only a fall below the basal hyperglycemic level. This could be explained by an increase in glucose mediated insulin secretion by compound no. 95. Hence, it is concluded that compound no. 95 would be a useful in the management of hyperglycemia in type II diabetes.

Free radicals along with AGE formation contributes to macroangiopathic (atherosclerosis, coronary artery disease) and microangiopathic (neuropathy, retinopathy, nephropathy) complication of diabetes.

The test compounds listed in Table-3 exhibit in vitro (antioxidant) free radical scavenging activity. The novel compounds show free radical scavenging activity, which would be useful for treatment of diabetes and diabetic vascular complications (DVCs).

The DPP-IV inhibitors under study are preferably expected to not only control diabetes, but also to prevent diabetic complications by their antioxidant actions.

Compound numbers 78, 95, 99, 104, 108 and 115 showed prominent dipeptidyl peptidase-IV inhibitory actions with their $IC_{50}$'s in the range of 88 to 250 nM. These compounds could be used to prevent the degradation of the insulinotrophic hormone GLP-1; and thereby elevate their circulating levels. These compounds are expected to exert their anti-hyperglycemic action in a glucose dependent way and hence the usual side effect of hypoglycemia observed with the classical sulphonylureas would not be observed.

Preparation of Representative Compounds of the Invention:

The compounds of the invention may be prepared by alternative synthetic routes as per Scheme I, II or III as described below:

SCHEME-I

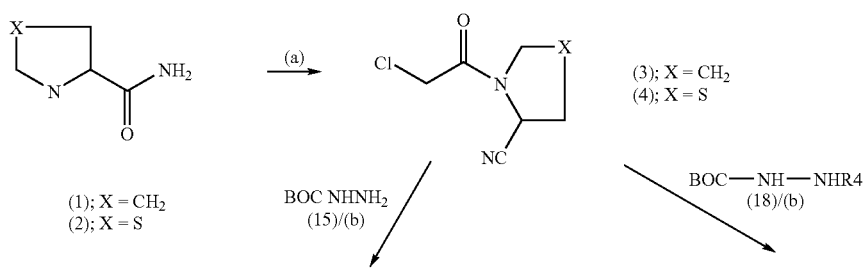

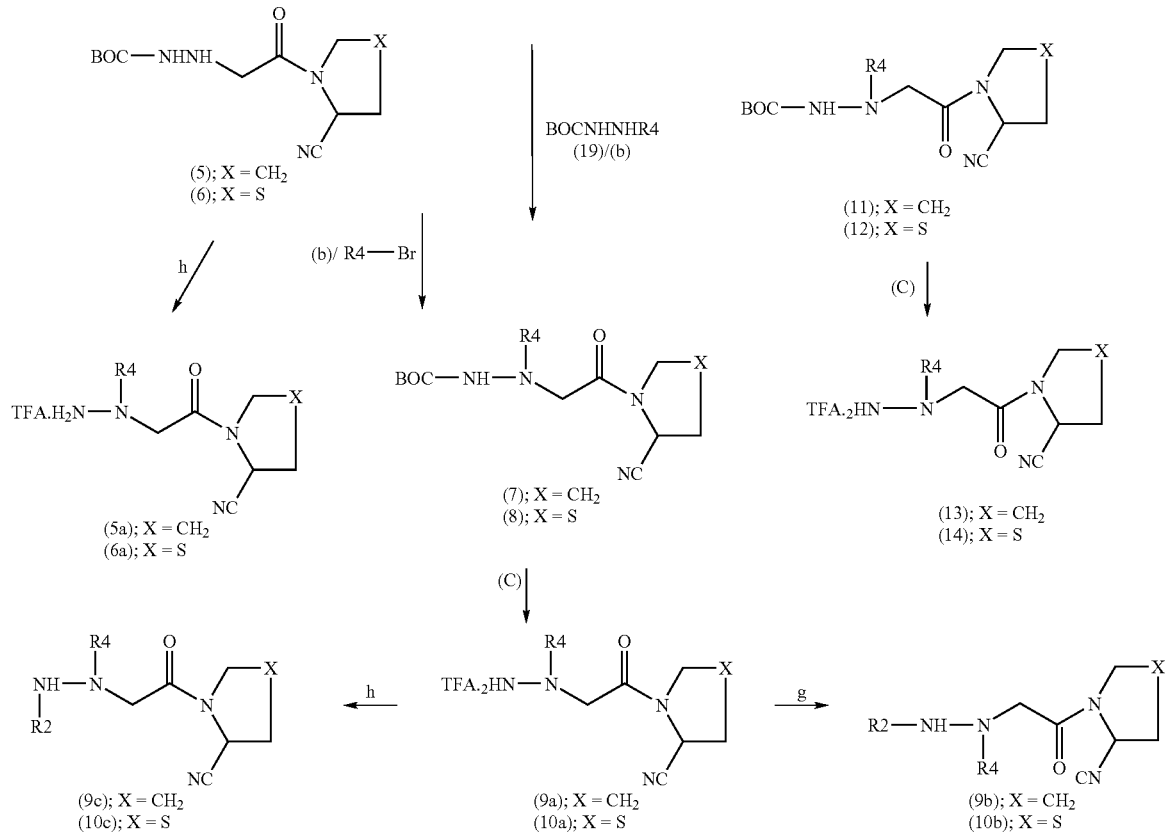

Route 1:

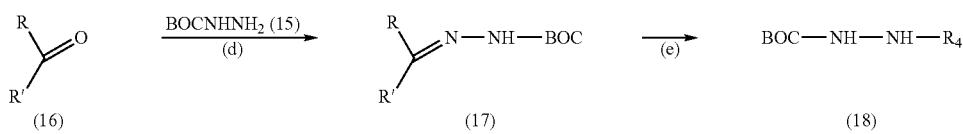

Route 2:

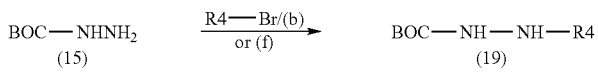

Reagents and Conditions for Scheme-I:

[a] (I) Et$_3$N, THF, K$_2$CO$_3$, ClCH$_2$COCl, 0–20° C., 2.5–3.0 hrs. (II) (CF3CO)2O/THF;

[b] K2CO3, KI, THF, Reflux, 6–20 hrs.

[c] CF3COOOH, Room Temp., 10–20 min.

[d] Hexane/Reflux, 2–4 hrs.

[e] NaBH4, MeOH, Reflux, 4–20 hrs.

[f] Neat, Reflux.

[g] (i) Aldehyde/ketone, MeOH, Reflux, (ii) NaCNBH$_3$, TiCl$_4$, MeOH

[h] (i) R8NHCOCl or R8SO$_2$Cl or R8COCl, TEA, THF, 0–20° C. (ii) [c]

Description:

The compounds of present invention may be prepared by the general methods as depicted in Scheme (I). The starting amide compound of formula (1) i.e L-prolinamide is prepared in four steps from L-proline following the same methods as described in literature for the synthesis of (R)-(−)-thiazolidine-4-amide of formula (2) from the corresponding acid.

Ref. U.S. Pat. No. 6,110,949 dated Aug. 29, 2000, Doreen M et al, Bio.Org. Med. Chem. Lett. 6(22), 1996, 2745–48]. L-prolinamide (1) is then converted to 1-chloroacetyl-2-cyanopyrrolidine of formula (3) in two steps which involves chloroacylation of the amide followed by dehydration [Ref. U.S. Pat. No. 6,124,305 dated Sep. 26, 2000, WO-0034241 dated Jun. 15, 2000 and U.S. Pat. No. 6,011,155 dated Apr. 4, 2000].

In a similar manner, the another starting material 3-chloroacetyl-4-cyano thiazolidine of formula (4) is prepared by following two step reactions sequence. Step-1 involves the reaction of thiazolidine amide of formula (2) with chloroacetylchloride in presence of a base such as potassium carbonate and an inert organic solvent like tetrahydrofuran at a temperature of from 0° C. to 20° C. for 2.5 to 3 hrs. Step 2 involves the dehydration of 3-chloroacetyl-thiazolidine-4-amide prepared in step-1, with 2-equivalents of trifluoroacetic anhydride conducted in presence of an inert organic solvent such as tetrahydrofuran at a temperature preferably at 20° C.

The second major component of the present invention i.e. N-2-substituted-tertbutyl carbazates of formulae (18) and (19), is prepared by the conventional manner. The tert-butyl alkylidine carbazates of formula (17) is prepared by refluxing hexane or tetrahydrofuran solution of tert-butyl carbazate (15) with appropriate aldehyde or ketone of formula (16) in 1:1 molar ratio for 2–4 hrs. [Ref. Dutta Anand S et.al., J. Chem. Soc. Perkin I, 1975, 1712–1720. Ghali N. I et al, J. Org. Chem. 46, 1981, 5413–5414].

The alkylidine carbazates thus formed in the previous step is reduced to N-2 substituted-tert-butyl carbazates of formula (18) using metal hydrides like sodium borohydride or lithium aluminium hydride, preferably sodium borohydride and Sodium cyanoborohydride. The solvent used in the reaction is organic solvent like methanol or tetrahydrofuran at a temperature ranging from 25° C. to 70° C. for 4 to 20 hrs.

On the other hand, direct alkylation of tert-butyl carbazate with alkyl or aryl halides preferably with the corresponding chlorides or bromides either in neat reaction condition or in presence of an inorganic base such as potassium carbonate and a catalyst such as potassium iodide in presence of THF provides carbazate derivatives of formula (19). Coupling of chloroacyl derivatives of formula (3) or (4) with the tert-butyl carbazate derivatives (18) or (19) in presence of $K_2CO_3$/KI in THF gives rise to hydrazinoacyl derivatives (11),(7),(12) or (8) which on deprotection using trifluoroaceticacid provides the final compounds (13), (9a),(14) or (10a) respectively as trifluoroacetate salts and further reaction of 9(a) or 10(a) with appropriate aldehyde followed by reduction using metal hydride like sodium borohydride or sodium cyanoborohydride in presence of catalytic compound of $TiCl_4$ (Titanium tetrachloride) gives rise to compounds 9(b) or 10(b).

Similar reaction of 9(a) or 10(a) with appropriate acid chloride or sulfonyl chloride gives rise to respective compounds 9(c) or 10(c).

Alternatively, the hydrazino derivatives (5) or (6) can be prepared from the corresponding chloroacyl derivatives (3) or (4) by reaction with tert-butyl carbazate itself. Alkylation of (5) or (6) with alkyl halides gives rise to penultimate intermediates (7) or (8) respectively.

Also, the reaction of compound (5) or (6) with appropriate carbamoyl chloride, sulphonyl chloride or acid chloride followed by deprotection with trifluroacetic acid gives rise to compound 5(a) or 6(a) respectively.

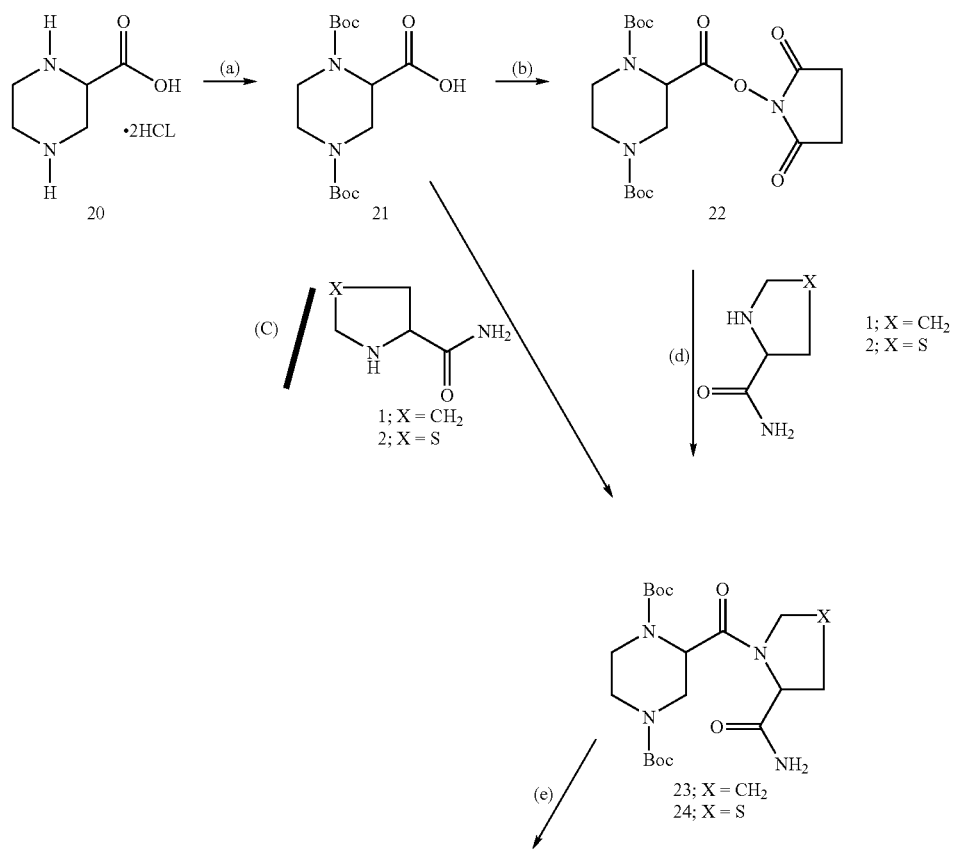

SCHEME-2

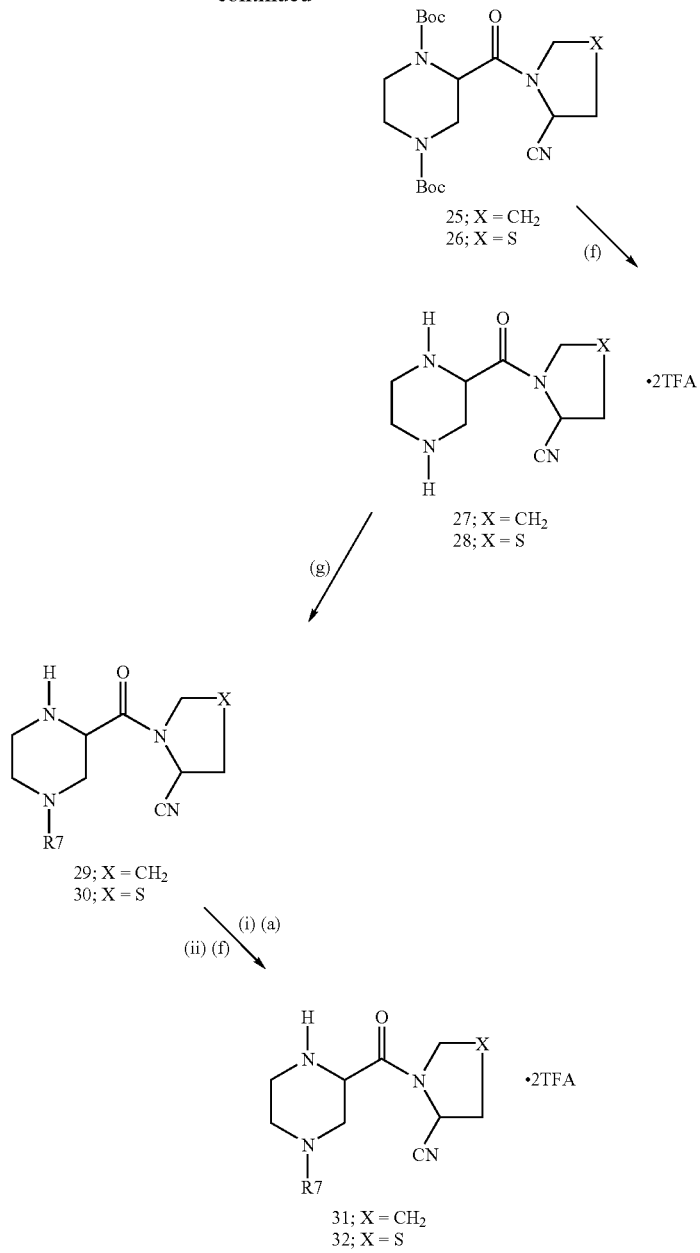

Reagents and Conditions for Scheme-II:
[a]: (Boc)$_2$O, NaOH, Dioxan, H$_2$O, 0°–25° C., 2–4 hrs;
[b]: NOSU, DCC, DCM, THF, 0°–15° C., 3–5 hrs;
[c]: HOBT, DCC, DIEA, DCM, −5°–25° C., 6–16 hrs;
[d]: DCM or THF, 5°–25° C., 12–22 hrs;
[e]: (CF$_3$CO)$_2$O, DCM or THF, Room Temp., 1–3 hrs;
[f]: CF$_3$COOH, CH$_3$CN, Room Temp., 3–4 hrs;
[g]: R7Br, Et$_3$N, K$_2$CO$_3$, THF, CH$_3$CN or RBr, Et$_3$N, THF, 0°–60° C., 1–25 hrs.

In an another embodiment of the present invention in which compounds, wherein the value of "k" mentioned in the general formula (I) is "null", then R$_4$ and R$_6$ together form optionally six or seven membered ring optionally containing two or three heteroatoms independently selected from O, S and NR$_7$, with R$_1$ is hydrogen, and N$_1$ is attached to hydrogen. As described represented by the formula (II), compounds may be prepared by the general methods as depicted in Scheme-II.

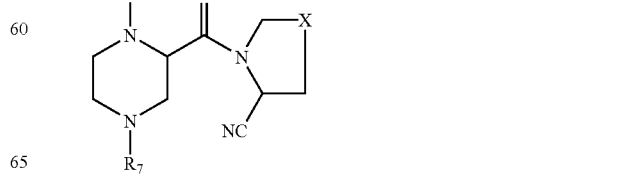

(II)

Piperazine-2-carboxylic acid dihydrochloride (20) is first protected by using usual protecting groups like Boc (tert-butyloxycarbonyl) or CBZ (benzyloxycarbonyl). The protected acid (21) is subjected to coupling with L-prolinamide (1) or (R)-(−)-thiazolidine-4-amide (2) to give the coupled products (23) or (24). This can either be done by first dicyclohexylcarbodiimide (DCC) mediated coupling of the acid (21) with N-hydroxysuccinimide (NOSU) to form the active ester (22) followed by its reaction with the amides (1 or 2), or by direct coupling of the protected acid (21) with the amides (1 or 2) in presence of 1-hydroxybenzotriazole (HOBT), DCC and the tertiaryamine like, diisopropylethyl amine (DIEA). Dehydration of the coupled products (23 or 24) using trifluroacetic anhydride as dehydrating agent provides the corresponding cyano derivatives (25 or 26). Deprotection of the compounds (25 or 26) in presence of trifluroacetic acid followed by regioselective functionalization of the deprotected compounds (27 or 28) at N-4 of piperazine ring using alkyl or aryl halides, or with acyl or sulphonyl halides yield the target compounds as represented by formula (29,30). They (29,30) can optionally be purified by reprotecting them at N-1 of the piperazine ring with a non-polar protecting group like Boc group, thereby, making these compounds more non polar, followed by deprotection of Boc group of this column purified intermediate using trifluroacetic acid results in the formation of final compounds as trifluroacetate salts (31,32).

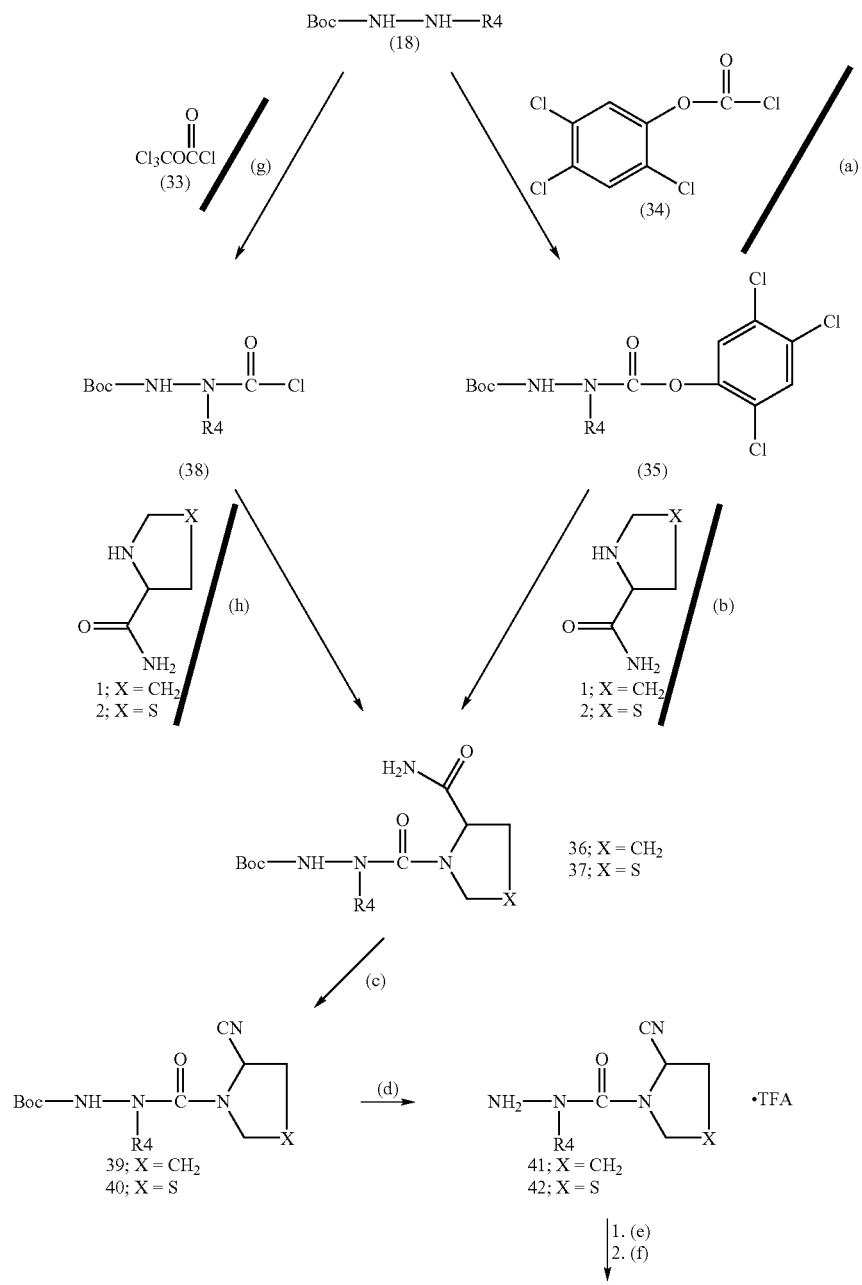

-continued

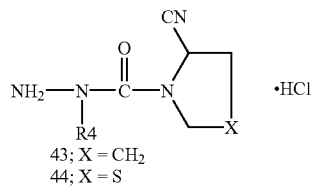

43; X = CH$_2$
44; X = S

Reagents and Conditions for Scheme-III:
a) Et$_3$N, THF or DCM, −25° to 4° C., N$_2$, 10–16 hrs.
b) Et$_3$N, THF or DCM, Reflux, 6–10 hrs.
c) (CF$_3$CO)$_2$O, THF, Room temp. 2–4 hrs.,
d) CF$_3$COOH, THF, 5° C. to Room temp. 0.5 to 2 hrs.,
e) Aqueous NaHCO$_3$,
f) MeOH.HCl
g) Et$_3$N, THF, −5° to 0° C., 1–2 hrs., N$_2$,
h) Et$_3$N, THF, 5° to 60° C., 12–18 hrs.

In a yet another embodiment of the present invention in which compounds described represented by the formula (III), wherein the value of "n" mentioned in the formula (I) is "null", may be prepared by the general methods as depicted in Scheme-III.

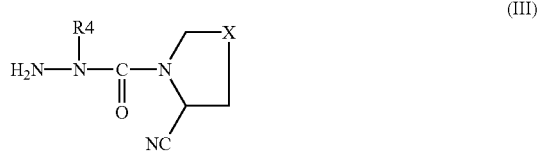

N-2-substituted tert-butyl carbazate (18) on reaction with 2,4,5-trichlorophenyl chloroformate (34), prepared from 2,4,5-trichlorophenol and trimethyl chloroformate (33) by the method as described in the literature, in presence of triethylamine as base results in the formation of carbazate derivatives (35). [Ref. Konakahara T et al, Synthesis, 1993, 103–106.]

The carbazate derivatives (35) on coupling with L-prolinamide (1) or thiazolidine amide (2) in presence of a tertiary amine as a base preferably triethylamine in an organic solvent like THF under reflux for 4–10 hrs. give the coupled products (36,37). These amide derivatives (36,37) can also be obtained by chlorocarbonylation of tert-butyl-carbazates (18) with trichloromethyl chloroformate (33) in presence of Et$_3$N at a low temperature(−5° to 0° C.), followed by coupling of the amides (1,2) with the chlorocarbonyl derivative of carbazates (38) in presence of Et$_3$N/THF at a temperature ranging from 25° to 60° C. for 8–12 hrs.

Subsequently usual dehydration of the amide derivatives (36,37) with trifluoroacetic anhydride in THF at a temperature from 5° to 30° C. for 2–4 hrs. followed by deprotection of the corresponding cyano derivatives (39,40) with a deprotecting agent like trifluoroacetic acid at a temperature in the range of 5° C. to 30° C. for 0.5 to 2 hrs, results in the formation of the final compounds (41,42) as trifluoroacetate salts. They can optionally be purified by neutralizing with an aqueous alkali like sodium bicarbonate (aqueous), purifying the free base thus obtained by column chromatography followed by converting to hydrochloride salts (43,44) by treating with methanolic hydrochloric acid at 10° C. to 20° C. for 1 to 2 hrs.

Representative example of Scheme I:

EXAMPLE-1

3-[1-Oxo-2-(-(1-cyclohexyl)hydrazino)]ethyl-4-cyano thiazolidine trifluoroacetate
[Compound No. 21).

Step: 1
A solution of tert-butyl cyclohexylidine (8.0 g, 37.7 mmol) in methanol (50 ml) was warmed to 50° C. and then added sodium borohydride (11.4 g, 301.6 mmol) in portions over a period of 20 minutes. Refluxed for 8 hrs. Reaction mixture is concentrated in vacuo. Reaction mixture diluted with water and extracted with ethylacetate. Ethylacetate layer washed with water, dried (Na$_2$ SO4), evaporated to dryness yielding the crude mass which is purified by column chromatography (5% ethyl acetate/hexane) gives N-cyclohexyl tert-butyl carbazate. (Yield 5.81 g, 71.95%).

Step: 2
To a solution of carbazate derivative (0.535 g, 2.5 mmol) thus formed in Step 1, and 3-chloroacyl-4-cyanothiazolidine (0.475 g, 2.5 mmol) (prepared in analogous manner as for corresponding pyrrolidine derivative) in THF (30 ml) is added K$_2$CO$_3$ (1.03 g, 7.5 mmol) and KI (0.29 g, 1.75 mmol). Reaction mixture is then refluxed for 6 hrs. Cooled, filtered, filtrate evaporated to dryness and the crude material purified by column chromatography (5% ethylacetate/hexane). (Yield 0.45 g, 48.9%).

Step: 3
Product obtained in step-2 (0.25 g, 0.68 mmol) is taken with trifluoroaceticacid (2.0 ml) at 0° C. and allowed to stir at 5–10° C. for 10 minutes. Trifluoroaceticacid removed in vacuo and final traces of trifluoroaceticacid removed by stripping off with toluene and methanol respectively, gives white solid as a trifluoroacetate salt, final product. (Yield 0.179 g, 69%).

EXAMPLE-2

3-[1-oxo-2-(1-cyclohexyl-2-isopropyl)hydrazino]ethyl-4-cyanothiazolidine hydrochloride
(Compound No. 36)

Product obtained in step-2 of example-1 (0.6 g, 1.57 mmol) was stirred with trifluoroacetic acid (5 ml) at 5–10° C. for 10 minutes. Trifluoro acetic acid removed in vacuo. To the residue, added 5 ml water and 5 ml saturated sodium carbonate solution, extracted with ethylacetate, evaporated to dryness yielded a mass. Resulting mass was refluxed in acetone (10 ml) for 2 hrs. Excess solvent was removed in vacuo. Obtained mass was taken in methanol (15 ml), cooled to 0° C., added sodium cyanoborohydride (8.1 mmol, 0.30 g) in portions, and stirred for 1 hr. Reaction mixture was concentrated in vacuo, treated with water, extracted with ethylacetate. Dried organic layer was evaporated to dryness, yielding a mass, which is purified by column chromatography (15% ethylacetate/hexane). Free base was stirred with methanolic hydrochloric acid (2 ml) for 15 min, solvent was removed in vacuo yielded hydrochloride salt. (200 mg, yield: 40%).

EXAMPLE-3

1,1-dioxo-3-[1-oxo-2-(1-methylcyclohexyl)hy-drazino)]ethyl-4-cyanothiazolidine trifluoroacetate (Compound No. 67).

Title compound is prepared by same method described in example-1 using N-(4-methyl-cyclohexyl)ter-butyl carbazate and 3-chloro-acyl-4-cyanothiazolidine-1,1-dioxide (prepared as followed).
To stirred solution of 3-chloroacyl-4-cyanothiazolidine (0.50 g, 2.6 mmol) in dichloromethane added meta-perchlorobenzoic acid (0.91 g, 5.2 mmol) in portions at 5–10° C. Reaction mixture was then stirred for 30 minutes and evaporated to dryness. Resulting crude mass was column chromatographed (20% ethylacetate/hexane) yielded desired compound (0.2 g, yield: 30%).

EXAMPLE-4

3-[1-oxo-2-(pyridizin-1yl)ethyl-4-cyanothiazolidine (Compound No. 83).

The solution of $N^+$-benzyloxycarbonyl-N-ter-butyloxycarbonyl hydrazine (4 g, 15 mmol) and 1,4-diabromobutane (5.8 g, 25.9 mmol) in acetonitrile (50 ml) was refluxed for 15 hrs in presence of potassium carbonate (4.2 g, 30 mmol). Reaction mixture was filtered, evaporated to dryness, purified by column chromatography (10% ethylacetate-hexane, 4 g, yield: 83%). The solution of obtained solid in 50% methanol-water (100 ml) was stirred with 5% palladium-charcoal (400 mg) at 50 psi for 6 hrs, filtered evaporated, and purified by column chromatography (ethylacetate 1.9 g, yield: 82%). The solution of obtained N-ter-butyloxypyridazine (1 g, 5.3mmol) was stirred with 3-chloroacyl-4-cyanothiazolidine (1.5 g, 7.8 mmol) in tetrahydrofuran (60 ml) at room temperature for 5 hrs in presence of cesium carbonate (2.6 g, 7.8 mmol) and then heated at 55° C. for 30 hrs. Reaction mixture was filtered, evaporated, column chromatographed (35% ethylacetate-hexane) yielded desired product (0.4 g, yield: 20%). Obtained product stirred with trifluoroacetic acid for 10 minutes at 5–10° C. Trifluoroacetic acid removed in vacuo neutralised with aqueous sodium carbonate, extracted with ethylacetate. Dried organic layer was evaporated to dryness, purified by column chromatography (2% methanol/dichloromethane) yielded 90 ml final compound (yield: 30%).

Representative Example of Scheme II:

EXAMPLE-5

2-Cyano-1-(4-isopropyl-2-piperazinyl)-carbonyl pyrrolidine trifluoroacetate (Compound No. 2).

Step-1
To an aqueous (100 ml) sodium hydroxide (4.0 g, 100 mmol) solution of piperazine-2-carboxylic acid dihydrochloride (5 g, 24.63 mmol) is added a solution of di-tert-butyl dicarbonate (11.0 g, 50.45 mmol) in dioxan (50 ml) at 0° C. over a period of half an hour. The reaction mixture is stirred at 0° C. for 1 hr. followed by stirring at room temperature (25° C.) for another 2 hrs. Neutralized (pH 6–7) with aqueous 2N HCl, extracted with ethyl acetate. Organic layer washed with brine solution, dried ($Na_2SO_4$) and evaporated in vacuo to yield an oil which solidifies on cooling. (Yield 8.02 g, 98.76%).

Step-2
Method-A
(i) To a dichloromethane (DCM, 40 ml) solution of Boc-protected acid (5.01 g, 15.18 mmol) as prepared in step-1 is added a solution of N-hydroxysuccinimide (1.75 g, 15.21 mmol) in THF (20ml) and a solution of DCC (3.6 g, 17.47 mmol) in DCM (20 ml) at 0° C. in the order specified. Reaction mixture stirred at 0–5° C. for 4–5 hrs, filtered, filtrate washed successively with water, aqueous sodium bicarbonate solution and finally with brine. Organic layer dried ($Na_2SO_4$) evaporated in vacuo to give the product as white solid. (Yield 5.8 g, 86.05%).
(ii) To a solution of the succinimide derivative (1.92 g, 4.49 mmol) in DCM (20 ml) as prepared in (i) of step-2, is added a solution of L-prolinamide (0.6 g, 5.26 mmol). Reaction mixture stirred at 25° C. for 16 hrs. washed with aqueous $NaHCO_3$ solution and brine, dried ($Na_2SO_4$), evaporated in vacuo yielding a crude residue. Desired coupled product was isolated by column chromatography (40% ethyl acetate/hexane), (Yield 0.53 g, 27.74%).

Method-B
Alternatively the above prolinamide derivative can be prepared by the following method.
DIEA (1.35 g, 10.46 mmol), HOBT (1.40 g, 10.37 mmol) sequentially added to piperazine acid (3.30 g, 10 mmol) and L-prolinamide (1.14 g, 10 mmol) in DCM (40 ml) at 0° C. A solution of DCC (2.40 g, 11.65 mmol) in DCM (30 ml) is added slowly at 0° C. over a period of 1 hr. Stirred another 1 hr. at 0° C. and then at 25° C. for 14 hrs. Filtered, DCM distilled off, diluted with ethyl acetate, washed sequentially with saturated aqueous solution of $NaHCO_3$ and brine. Organic layer dried ($Na_2SO_4$), evaporated in vacuo purified by column chromatography (ethyl acetate). (Yield 2.6 g, 61.03%).

Step-3
Prolinamide derivative (0.8 g, 1.87 mmol) in THF (15 ml) is stirred with trifluoroacetic anhydride (TFAA) (1.5 g, 7.14 mmol) at room temperature (25° C.) for 4 hrs. Excess TFAA and THF is distilled off in vacuo, diluted with ethyl acetate, washed with aqueous sodium bicarbonate solution and brine. Organic layer dried ($Na_2SO_4$), evaporated in vacuo and the required cyano compound purified by column chromatography (50% ethyl acetate/hexane). (Yield 0.6 g, 78.32%).

Step-4
Deprotection of the above compound as obtained in step-3 is done by stirring a solution of the compound (0.5 g, 1.22 mmol) in $CH_3CN$ (10 ml) with TFA (7 ml) at room temperature for 2 hrs. Excess TFA and $CH_3CN$ removed in vacuo followed by stripping off with toluene and methanol respectively results in the formation of deprotected product as trifluoroacetate salt. (Yield 0.52 g, 97.32%).

Step-5
To a solution of the deprotected compound (0.64 g, 1.46 mmol) as obtained in step-4, in acetone (30 ml), was added triethylamine (0.45 g, 4.45 mmol), $K_2CO_3$ (0.3 g, 2.17 mmol) and isopropyl bromide (0.23 g, 1.88 mmol) and refluxed for 15 hrs. The reaction mixture is filtered and the filtrate is evaporated in vacuo to give the product as an oily residue. (Yield 0.2 g, 54.51%).

The crude material thus obtained is purified as follows:

The compound is protected using di-tert-butyl dicarbonate (0.18 g, 0.82 mmol) and NaOH (0.05 g, 1.25 mmol) in the same way as described in step-1 and purified by column chromatography (50% ethyl acetate/hexane). (Yield 0.15 g, 53.57%). This is finally deprotected using trifluoroacetic acid (2 ml) resulting in the formation of the final product as trifluoroacetate salt. (Yield 0.11 g, 53.92%).

Representative Example of Scheme III:

EXAMPLE-6

[4-Cyano-3-(1-cyclohexylhydrazino)carbonyl thiazolidine hydrochloride] (Compound No. 33).

Step-1

A solution of trichloromethyl chloroformate (3.43 g, 17.50 mmol) in THF (15 ml) is added slowly at 0° C. to a stirred solution of tert-butyl-cyclohexyl carbazate (2.5 g, 11.68 mmol) in THF (15 ml) under $N_2$ atmosphere. Triethylamine (1.77 g, 17.52 mmol) in THF (15 ml) is next added at 0° C. slowly over a period of 20 minutes. Stirred at 0° C. for 1.5 hrs, THF distilled off, diluted with DCM (30 ml), washed sequentially with water and 5% aqueous citric acid solution. Organic layer dried ($Na_2SO_4$) and removed in vacuo to give the product. (Yield 3.10 g, 96.27%).

Step-2

To a solution of thiazolidine amide (0.66 g, 5.0 mmol) and the product obtained in step-1 (1.96 g, 7.10 mmol) in THF (30 ml) is added a solution of triethylamine (1.6 g, 15.84 mmol) in THF (10 ml) dropwise at 5° C. over a period of half an hr. Stirred at room temp. for 15 hrs, followed by refluxing for 1 hr. THF distilled off, diluted with ethyl acetate, washed successively with water and 5% aqueous citric acid, organic layer dried ($Na_2SO_4$), evaporated in vacuo and crude material purified by column chromatography (50% ethyl acetate/hexane). (Yield 0.85 g, 45.70%).

Step-3

Trifluoroacetic anhydride (0.54 g, 2.57 mmol) is added to a solution of the amide compound (0.80 g, 2.15 mmol) as obtained in step-2, in THF (15 ml) at 5° C. and stirred at 30° C. for 3 hrs. Excess solvents removed in vacuo, diluted with ethyl acetate, washed with aqueous 5% $NaHCO_3$ solution, dried ($Na_2SO_4$) and concentrated. Crude material purified by column chromatography (20% ethyl acetate/hexane). (Yield 0.43 g, 56.48%).

Step-4

The deprotection is done by stirring a solution of the cyano compound (0.43 g, 1.21 mmol) with TFA (5 ml) in THF (5 ml) at 5° C. for 1 hr. Excess solvents distilled off in vacuo, diluted with ethyl acetate, washed with saturated aqueous solution of $NaHCO_3$. Organic layer dried ($Na_2SO_4$), evaporated and the required pure compound is isolated as a free base after column chromatography (35% ethyl acetate/hexane). (Yield 0.10 g, 32.46%).

This is converted to its hydrochloride salt by treating with methanolic HCl at 10° C. for 1 hr. and removing excess solvents in vacuo followed by crystallization from ether.

The following representative compounds may be prepared by following the synthetic route of Scheme I.

EXAMPLE-7

1-[1-Oxo-2-((1-Cycloheptyl)-hydrazino)]ethyl-2-cyano pyrrolidine trifluoroacetate (Compound No. 30)

| | |
|---|---|
| Yield | 60.6%; |
| m.p. | 138–140° C.; |
| Mass(m/z) | 265($M^+$+1), 287($M^+$+Na); |
| $^1$HNMR(400 MHz, $CDCl_3$)δ | 4.88–4.90(m, 1H), 4.10–4.34(m, 3H), |
| | 3.58–3.79(m, 2H), 2.19–2.29(m, 6H), |
| | 1.73–1.81(m, 4H), 1.54–1.57(m, 6H); |
| IR.(KBr, $cm.^{-1}$) | 3460, 3170, 2270, 1673, 1605, and 1524. |

EXAMPLE-8

3-[1-Oxo-2-((1-(4-methyl)cyclohexyl)-hydrazino)] ethyl-4-cyano thiazolidine trifluoroacetate (Compound No. 29)

| | |
|---|---|
| Yield | 58.2%; |
| m.p. | 140–142° C.; |
| Mass(m/z) | 283($M^+$+1), 267; |
| $^1$HNMR(400 MHz, $CDCl_3$)δ | 5.27–5.29(m, 1H), 4.13–4.57(m, 4H), |
| | 3.49–3.75(m, 4H), 1.82(bs, 4H), |
| | 1.38(bs, 4H), 0.98(d, 3H, J=8Hz); |
| IR(KBr, $cm.^{-1}$) | 3460, 3175, 2250, 1670, 1605, and 1523. |

EXAMPLE-9

3-[1-Oxo-2-((1-Cycloheptyl)-hydrazino)]ethyl-4-cyano thiazolidine trifluoroacetate (Compound No. 28)

| | |
|---|---|
| Yield | 72.8%; |
| m.p. | 141–142° C.; |
| Mass(m/z) | 283($M^+$+1); |
| $^1$HNMR (400 MHz, $d_4$-MeOH)δ | 5.34–5.36(t, 1H, J=4Hz), 4.72–4.74 (d, 1H, J=8Hz), |
| | 4.64–4.66(d, 1H, J=8Hz), |
| | 4.06–4.18(m, 2H), 3.39–3.50 |
| | (m, 2H), 2.04(bs, 2H), 1.82(bs, 2H), |
| | 1.70–1.73(m, 2H), 1.56–1.63(m, 7H); |
| IR(KBr, $cm.^{-1}$) | 3477, 3408, 2340, 1672, 1626, 1562, 1524. |

EXAMPLE-10

1-[1-Oxo-2-(1-(2-Pyridyl)-hydrazino)]ethyl-2-cyano pyrrolidine bis-trifluoroacetate (Compound No. 27)

| | |
|---|---|
| Yield | 36.50%; |
| Mass(m/z) | 246(M⁺+1), 150, 167; |
| ¹HNMR(400 MHz, d₄-MeOH)δ | 8.65–8.67(d, 1H, J=8Hz), 8.48–8.52 (t, 1H, J=8Hz), 7.79–7.81(d, 1H, J=8Hz), 7.58–7.62(t, 1H, J=8Hz), 4.69–4.73 (t, 1H, J=8Hz), 3.40–3.51(m, 4H), 2.20–2.33(m, 4H); |
| IR(CCl₄, cm.⁻¹) | 3445, 2248, 1677, 1519. |

EXAMPLE-11

1-[1-Oxo-2-((4-Methyl)cyclohexyl)hydrazino)]ethyl-2-cyano pyrrolidine trifluoroacetate (Compound No. 26)

| | |
|---|---|
| Yield | 87.70%; |
| Mass(m/z) | 265(M⁺+1), 287(M⁺+Na); |
| ¹HNMR(400 MHz, d₄-MeOH)δ | 4.04(bs, 1H), 3.65–3.71(m, 1H), 3.48–3.55(m, 1H), 3.15–3.17(m, 1H), 2.26–2.31(m, 2H), 2.18–2.22(t, 2H, J=8Hz), 2.03–2.05 (m, 2H), 1.86–1.89(m, 2H), 1.30–1.45(m, 7H), 0.92–0.94(d, 3H, J=8Hz); |
| IR(CCl₄, cm.⁻¹) | 3400, 2248, 1676, 1454. |

EXAMPLE-12

3-[1-Oxo-2-((1-(4-methyl)cyclohexyl)hydrazino)] ethyl-4-cyano thiazolidine trifluoroacetate (Compound No. 25). [** This compound obtained by reacting with lower isomer obtained during the reduction step]

| | |
|---|---|
| Yield | 73.9%; |
| m.p. | 89–90° C.; |
| Mass(m/z) | 283(M⁺+1), 305(M⁺+Na), 266; |
| ¹HNMR(400 MHz, d₄-MeOH)δ | 5.33–5.35(t, 1H, J=4Hz), 4.71–4.73 (d, 1H, J=8Hz), 4.64–4.66(d, 1H, J=8Hz), 4.05–4.16(m, 2H), 3.38–3.40(m, 2H), 3.12–3.18(m, 1H), 2.01–2.03(m, 2H), 1.86–1.89(m, 2H), 1.36–1.43(m, 3H), 1.01–1.10 (m, 2H), 0.93–0.95(d, 3H, J=8Hz); |
| IR(KBr, cm.⁻¹) | 3477, 3403, 2340, 1670, 1629, 1567, 1523. |

EXAMPLE-13

1-[1-Oxo-2-((1-Phenyl sulphonyl)hydrazino)]ethyl-2-cyano pyrrolidine trifluoroacetate (Compound No. 24)

| | |
|---|---|
| Yield | 80.6%; |
| Mass (m/z) | 331 (M⁺ + Na), 283; |
| ¹HNMR (400 MHz, d₄-MeOH) δ | 7.36–7.84 (m, 5H), 4.72–4.75 (m, 1H), 3.55–3.70(m, 2H), 2.12–2.33 (m, 6H); |
| IR (CCl₄, cm.⁻¹) | 3444, 2337, 1639, 1424. |

EXAMPLE-14

3-[1-Oxo-2-((1-methylpropyl)hydrazino)]ethyl-4-cyano thiazolidine trifluoroacetate (Compound No. 23)

| | |
|---|---|
| Yield | 90.3%; |
| Mass (m/z) | 243 (M⁺ + 1), 225; |
| ¹HNMR (400 MHz, d₄-MeOH) δ | 5.34–5.36 (t, 1H, J=4Hz), 4.75–4.77 (d, 1H, J=8Hz), 4.67–4.69 (d, 1H, J=8Hz), 4.04 (bs, 2H), 3.39-3.47 (m, 3H), 1.36–1.42 (m, 2H), 1.26–1.28 (d, 3H, J=8Hz), 0.99–1.03 (t, 3H, J=8Hz) |
| IR (CCl₄, cm.⁻¹) | 3470, 2340, 1676, 1632, 1521 |

EXAMPLE-15

1-[1-Oxo-2-((1-methylpropyl)hydrazino)]ethyl-2-cyano pyrrolidine trifluoroacetate (Compound No. 22)

| | |
|---|---|
| Yield | 86.9%; |
| Mass (m/z) | 225 (M⁺ + 1); |
| ¹HNMR (400 MHz, d₄-MeOH) δ | 4.79–4.80 (bs, 1H), 3.98 (bs, 2H), 3.67–3.72 (m, 1H), 3.49–3.56 (m, 1H), 2.18–2.31 (m, 3H), 1.77–1.80(m, 1H), 1.52–1.54 (m, 1H), 1.35–1.38(m, 2H), 1.28–1.30 (d, 3H, J=8Hz), 1.00–1.04 (t, 3H, J=8Hz); |
| IR (CCl₄, cm.⁻¹) | 3441, 2280, 1676, 1521. |

EXAMPLE-16

3-[1-Oxo-2-((1-Cyclohexyl)-hydrazino)]ethyl-4-cyano thiazolidine trifluoroacetate (Compound No. 21)

| | |
|---|---|
| Yield | 69%; |
| m.p. | 154–155° C.; |
| Mass (m/z) | 269(M⁺ + 1), 291(M⁺ + Na); |
| ¹HNMR (400 MHz, d₄-MeOH) δ | 5.33 (t, 1H, J=4Hz), 4.72–4.74 (d, 1H, J=8Hz), 4.64–4.66 (d, 1H, J=8Hz), 4.02–4.12 (m, 2H), 3.38–3.40 (d, 2H, J=8Hz), 3.19–3.26 (m, 1H), 1.92–2.01 (m, 4H), 1.69–1.72 (m, 1H), 1.32–1.38 (m, 4H), 1.22–1.24 (m, 1H); |
| IR (KBr, cm.⁻¹) | 3172, 2342, 1676, 1608, 1521. |

EXAMPLE-17

1-[1-Oxo-2-((1-Cyclohexyl)-hydrazino)]ethyl-2-cyano pyrrolidine trifluoroacetate
(Compound No. 20)

| | |
|---|---|
| Yield | 81.7%: |
| m.p. | 148–150° C.; |
| Mass (m/z) | 251 ($M^+$ + 1), 273($M^+$ + Na), 225; |
| $^1$HNMR (400 MHz, $d_4$-MeOH)δ | 4.81–4.84 (bs, 1H), 3.99–4.03 (m, 2H), 3.66–3.70 (m, 1H), 3.50–3.55 (m, 1H), 3.33–3.36 (m, 1H), 3.18–3.22 (m, 1H), 2.26–2.29 (m, 1H), 2.18–2.23 (m, 2H), 2.00–2.02 (m, 2H), 1.90–1.90 (m, 2H), 1.69–1.73 (m, 1H), 1.35–1.41 (m, 5H); |
| IR (KBr, cm.$^{-1}$) | 3159, 2241, 1676, 1607, 1519. |

EXAMPLE-18

3-[1-Oxo-2-((1-Cyclopentyl)-hydrazino)]ethyl-4-cyano thiazolidine trifluoroacetate
(Compound No. 19)

| | |
|---|---|
| Yield | 48.3%: |
| m.p. | 136–137° C.; |
| Mass (m/z) | 255 ($M^+$ + 1), 277($M^+$ + Na) |
| $^1$HNMR (400 MHz, $d_4$-MeOH)δ | 5.34–5.36 (t, 1H, J=4Hz), 4.73–4.75 (d, 1H, J=8Hz), 4.63–4.65 (d, 1H, J=8Hz), 4.02–4.14 (m, 2H), 3.65–3.69 (m, 1H), 3.38–3.39 (d, 2H, J=4Hz), 1.98–2.02 (m, 2H), 1.81–1.85 (m, 2H), 1.65–1.69 (m, 4H); |
| IR (KBr, cm.$^{-1}$) | 3180, 2365, 1677, 1602, 1524. |

EXAMPLE-19

1-[1-Oxo-2-((1-Cyclopentyl)-hydrazino)]ethyl-2-cyano pyrrolidine trifluoroacetate
(Compound No. 18)

| | |
|---|---|
| Yield | 64.1%: |
| m.p. | 118–119° C.; |
| Mass (m/z) | 237 ($M^+$ + 1), 259($M^+$ + Na); |
| $^1$HNMR (400 MHz, $d_4$-MeOH)δ | 4.71–4.75 (bs, 1H), 3.97–4.01 (m, 2H), 3.66–3.69 (m, 2H), 3.48–3.52 (m, 1H), 2.18–2.29 (m, 4H), 1.98–2.02 (m, 2H), 1.80–1.85 (m, 2H), 1.65–1.69 (m, 4H); |
| IR (KBr, cm.$^{-1}$) | 3169, 2241, 1679, 1605, 1522. |

EXAMPLE-20

3-[1-Oxo-2-((1-(4-nitrophenylmethyl))hydrazino)]ethyl-4-cyano thiazolidine trifluoroacetate
(Compound No. 17)

| | |
|---|---|
| Yield | 76.9%: |
| Mas (m/z) | 322 ($M^+$ + 1); |
| $^1$HNMR (400 MHz, $d_4$-MeOH)δ | 8.24–8.31 (dd, 2H, J=8Hz, 12Hz), 7.63–7.70(dd, 2H, J=8Hz, 12Hz,), 5.35–5.37 (t, 1H, J=4Hz,), 4.66-4.79 (m, 2H), 4.01–4.41 (m, 4H), 3.37–3.38 (m, 2H); |
| IR (CCl$_4$, cm.$^{-1}$) | 3422, 2338, 1655, 1510. |

EXAMPLE-21

3-[1-Oxo-2-((1-phenylmethyl)hydrazino)]ethyl-4-cyano thiazolidine trifluoroacetate
(Compound No. 16)

| | |
|---|---|
| Yield | 64.3%; |
| Mass (m/z) | 277 ($M^+$ + 1), 299($M^+$ + Na), 261; |
| $^1$HNMR (400 MHz, $d_4$-MeOH)δ | 7.35–7.46 (m, 5H), 5.33–5.35 (t, 1H, J=4Hz,), 4.43–4.49 (m, 2H), 4.25 (s, 2H), 3.90 (s, 2H), 3.36–3.37 (d, 2H, J=4Hz,); |
| IR (KBr, cm.$^{-1}$) | 3470, 2340, 1671, 1620, 1508. |

EXAMPLE-22

3-[1-Oxo-2-(1-hydrazino)]ethyl-4-cyano thiazolidine trifluoroacetate (Compound No. 15)

| | |
|---|---|
| Yield | 63.7%: |
| Mass (m/z) | 187 ($M^+$ + 1); |
| $^1$HNMR (400 MHz, $d_4$-MeOH)δ | 5.04 (bs, 1H), 4.41–4.49 (m, 2H), 3.58–3.62 (dd, 2H, J=5.6Hz, 4.8Hz), 3.26–3.33 (m, 2H); |
| IR (CCl$_4$, cm.$^{-1}$) | 3460, 2260, 1676, 1508. |

EXAMPLE-23

1-[1-Oxo-2-((1-ethyl)hydrazino)]ethyl-2-cyano pyrrolidine trifluoroacetate (Compound No. 14)

| | |
|---|---|
| Yield | 38.2%; |
| Mass (m/z) | 197($M^+$ + 1), 219($M^+$ + Na); |
| $^1$HNMR (400 MHz, $d_4$-MeOH)δ | 4.82–4.84 (bs, 1H), 4.22–4.24 (bs, 1H), 3.98–4.00 (m, 1H), 3.65–3.70 (m, 1H), 3.48–3.54 (m, 1H), 3.17–3.23 (q, 2H, J=8Hz), 2.13–2.31 (m, 4H), 1.26–1.30 (t, 3H, J=8Hz); |
| IR (CCl$_4$, cm.$^{-1}$) | 3424, 2247, 1676, 1521. |

EXAMPLE-24

1-[1-Oxo-2-((2,2-diethyl)-hydrazino)]ethyl-2-cyano thiazolidine (Compound No. 13)

| | |
|---|---|
| Yield | 52.3%; |
| Mass (m/z) | 243($M^+$ + 1); |
| $^1$HNMR (400 MHz, $d_4$-MeOH)δ | 5.36–5.38(t, 1H, J=4Hz), 4.75–4.77 (d, 1H, J=8Hz), 4.61–4.63 (d, 1H, J=8Hz), 3.82–3.85 (dd, 1H, J=4Hz, 4Hz), 3.75–3.78 (dd, 1H, J=4Hz, 4Hz), 3.40–3.41 (d, 2H, J=4Hz), 3.20–3.26 (q, 4H, J=8Hz), 1.31–1.35 (t, 6H, J=8Hz); |
| IR (CCl$_4$, cm.$^{-1}$) | 3440, 2253, 1678, 1460. |

EXAMPLE-25

1-[1-Oxo-2-((1-(1-methyl)ethyl)hydrazino)]ethyl-2-cyano pyrrolidine trifluoroacetate (Compound No. 12)

| | |
|---|---|
| Yield | 38.3%; |
| Mass (m/z) | 211($M^+$ + 1), 233 ($M^+$ + Na); |
| $^1$HNMR (400 MHz, $d_4$-MeOH)δ | 4.83–4.86(t, 1H, J=4Hz), 4.05–4.11 (m, 2H), 3.67–3.72 (m, 1H), 3.50–3.61 (m, 2H), 2.28–2.32 (m, 2H), 2.16–2.23 (m, 2H), 1.30–1.32 (d, 6H, J=8Hz); |
| IR (CCl$_4$, cm.$^{-1}$) | 3280, 2250, 1675, 1522. |

EXAMPLE-26

1-[1-Oxo-2-((1-phenylmethyl)hydrazino)]ethyl-2-cyano pyrrolidine trifluoroacetate (Compound No. 11)

| | |
|---|---|
| Yield | 67.6%; |
| Mass (m/z) | 259 ($M^+$ + 1), 281 ($M^+$ + Na), 158; |
| $^1$HNMR (400 MHz, $d_4$-MeOH)δ | 7.37–7.44(m, 5H), 4.82–4.84 (t, 1H, J=4Hz), 4.26 (s, 2H), 3.79 (s, 2H), 3.39–3.45 (m, 1H), 3.27–3.32 (m, 1H), 2.22–2.27 (m, 2H), 2.09–2.16 (m, 2H); |
| IR (CCl$_4$, cm.$^{-1}$) | 3470, 2340, 1676, 1451. |

EXAMPLE-27

1-[1-Oxo-2-(1-(2-methylpropyl)hydrazino)]ethyl-2-cyano pyrrolidine trifluoroacetate (Compound No. 10)

| | |
|---|---|
| Yield | 88%; |
| Mass (m/z) | 225 ($M^+$ + 1), 247 ($M^+$ + Na); |
| $^1$HNMR (400 MHz, $d_4$-MeOH)δ | 4.82–4.84 (t, 1H, J=4Hz), 3.83–3.89 (m, 2H), 3.64–3.69 (m, 1H), 3.47–3.53 (m, 1H), 2.84–2.86 (d, 2H, J=8Hz), 2.25–2.30 (m, 2H), 2.16–2.21 (m,2H), 1.30–1.37 (m, 1H), 0.99–1.00 (d, 6H, J=4Hz) |
| IR (CCl$_4$, cm.$^{-1}$) | 3443, 2280, 1675, 1557, 1453. |

EXAMPLE-28

3-[1-Oxo-2-((1-phenyl)hydrazino)]ethyl-4-cyano thiazolidine trifluoroacetate (Compound No. 9)

| | |
|---|---|
| Yield | 56.4%; |
| Mass (m/z) | 263 ($M^+$ + 1), 285 ($M^+$ + Na), 235; |
| $^1$HNMR (400 MHz, $d_4$-MeOH)δ | 7.22–7.40 (m, 3H), 6.77–6.94 (m, 2H), 4.95–4.97 (m, 1H), 4.62–4.82 (m, 2H), 4.12–4.20 (m, 2H), 3.32–3.36 (m, 2H); |
| IR (CCl$_4$, cm.$^{-1}$) | 3440, 2339, 1677, 1436. |

EXAMPLE-29

1-[1-Oxo-2-((1-(4-nitrophenylmethyl))hydrazino)]ethyl-2-cyano pyrrolidine trifluoroacetate (Compound No. 8)

| | |
|---|---|
| Yield | 52%; |
| m.p. | 107–108° C.; |
| Mass (m/z) | 304 ($M^+$ + 1), 326 ($M^+$ + Na); |
| $^1$HNMR (400 MHz, $d_4$-MeOH)δ | 8.29–8.31 (d, 2H, J=8Hz), 7.68–7.70 (d, 2H, J=8Hz), 4.84–4.86(t, 1H, J=4Hz), 4.39 (s, 2H), 3.90–3.91 (d, 2H, J=4Hz), 3.50–3.54 (m, 2H), 2.24–2.28 (m, 2H), 2.14–2.18 (m, 2H); |
| IR (KBr, cm.$^{-1}$) | 3420, 3180, 2339, 1675, 1604, 1515. |

EXAMPLE-30

1-[1-Oxo-2-((2-(1,1-dimethylethyloxy carbonyl))hydrazino)]ethyl-2-cyano pyrrolidine (Compound No. 7)

| | |
|---|---|
| Yield | 45.3%; |
| Mass (m/z) | 269 ($M^+$ + 1), 291 ($M^+$ + Na), 213; |
| $^1$HNMR (400 MHz, $d_4$-MeOH)δ | 4.77–4.79 (t, 1H, J=4Hz), 3.61–3.74 (m, 3H), 3.46–3.54 (m, 1H), 2.23–2.28 (m, 2H), 2.13–2.20 (m, 2H), 1.46 (s.9H); |
| IR (CCl$_4$, cm.$^{-1}$) | 3306, 2979, 2242, 1678, 1530. |

EXAMPLE-31

1-[1-Oxo-2-((2-(1,1-dimethylethyloxy carbonyl))-1-phenyl hydrazino)]ethyl-2-cyano pyrrolidine (Compound No. 6)

| | |
|---|---|
| Yield | 53.7%; |
| Mass (m/z) | 345 (M$^+$+ 1), 367 (M$^+$ + Na), 267; |
| $^1$HNMR (400 MHz, CDCl$_3$)δ | 7.22–7.26(m, 2H), 6.75–6.89 (m, 3H), 6.37 (bs, 1H), 4.77–4.80(t, 1H, J=8Hz), 4.07 (s, 2H), 3.72–3.76 (m, 1H), 3.60–3.66 (m, 1H), 2.20–2.37 (m, 4H), 1.35 (s, 9H); |
| IR (CCl$_4$, cm.$^{-1}$) | 3470, 3333, 2242, 1663, 1602, 1496. |

EXAMPLE-32

3-[1-Oxo-2-((2-(1,1-dimethyl ethyl oxy carbonyl)) hydrazino)]ethyl-4-cyano thiazolidine (Compound No. 5)

| | |
|---|---|
| Yield | 33.3%; |
| Mass (m/z) | 287 (M$^+$ + 1), 309 (M$^+$ + Na), 231; |
| $^1$HNMR (400 MHz, CDCl$_3$)δ | 7.44–7.48(m, 1H), 7.20–7.24 (m, 1H), 5.24–5.34 (m, 1H), 4.68–4.75 (m, 1H), 4.55 (s, 1H), 3.84 (bs, 1H), 3.46–3.56 (m, 1H), 3.30–3.35 (m, 2H), 1.48 (s, 9H); |
| IR (CCl$_4$, cm.$^{-1}$) | 3401, 2241, 1733, 1578, 1540. |

EXAMPLE-33

1-[1-Oxo-2-(1-hydrazino)]ethyl-2-cyano pyrrolidine trifluoroacetate (Compound No. 4)

| | |
|---|---|
| Yield: | 42.3%; |
| Mass (m/z): | 168 (M$^+$ + 1), 191 (M$^+$ + Na); |
| $^1$HNMR (400 MHz, d$_4$-MeOH)δ: | 4.79–4.81 (m,1H), 3.88 (s, 2H), 3.62–3.69 (m, 2H), 2.24–2.29 (m, 2H), 2.12–2.20 (m, 2H); |
| IR (CCl$_4$, cm.$^{-1}$): | 3470, 3250, 2240, 1678, 1435. |

EXAMPLE-34

1-[1-Oxo-2-((1-phenyl)-hydrazino)]ethyl-2-cyano pyrrolidine trifluoroacetate (Compound No. 3)

| | |
|---|---|
| Yield: | 96.1%; |
| Mass (m/z): | 245 (M$^+$ + 1), 267 (M$^+$ + Na), 228; |
| $^1$HNMR (400 MHz, CDCl$_3$) δ: | 7.00–7.42 (m, 5H), 4.78–4.80 (b,s), 4.08 (s, 2H), 3.64–3.83 (m, 2H), 2.24–2.34 (m, 4H); |
| IR (CCl$_4$, cm.$^{-1}$): | 3441, 2339, 1679, 1432. |

EXAMPLE-35

1-[1-Oxo-2-(2-cyclohexyl)hydrazino]ethyl-2-cyanopyrrolidine trifluoroacetate (Compound No. 34)

| | |
|---|---|
| Yield: | 97%. |
| Mass: | 251 (M$^+$ + 1), 273 (M$^+$ + Na); |
| $^1$HNMR (CDCl$_3$) δ: | 4.70 (bs, 1H), 3.97–4.01 (d, 1H, J=16 Hz), 3.81–3.85 (d, 1H, J=16Hz), 3.58–3.65 (m, 2H), 3.45–3.53 (m, 2H), 3.14–3.20 (m, 3H), 2.18–2.21 (m, 4H), 1.86–1.89 (m, 4H), 1.68–1.71 (m, 2H); |
| IR (Neat, Cm$^{-1}$): | 2938, 2246 and 1670 |

EXAMPLE-36

[4-Cyano-3-(1-phenyl hydrazino)carbonyl thiazolidine trifluoroacetate] (Compound No. 35)

| | |
|---|---|
| Yield: | 37.8%. |
| Mass: | 249 (M$^+$ + 1), 271 (M$^+$ + Na); |
| $^1$HNMR (CDCl$_3$) δ: | 7.51–7.54 (d, 2H, J=12Hz), 7.35–7.39 (dd, 2H, J=8Hz, 8Hz), 7.19–7.23 (dd, 1H, J=8Hz, 8Hz) 5.36–5.38 (d, 1H, J=8Hz), 4.31–4.33 (d, 1H, J=8Hz), 4.22–4.26 (dd, 1H, J=6Hz, 6Hz), 4.08 (bs, 2H), 3.33–3.37 (dd, 1H, J=8Hz, 8Hz), 3.08–3.14 (t, 1H, J=12Hz); |
| IR (Neat, Cm$^{-1}$): | 2935, 2244 and 1663. |

EXAMPLE-37

3-[1-Oxo-2-(1-cyclohexyl-2-isopropyl)hydrazino] ethyl-4-cyanothiazolidine hydrochloride (Compound No. 36)

| | |
|---|---|
| Yield: | 40%. |
| Mass: | 311 (M$^+$ + 1); |
| $^1$HNMR (d$_4$-MeOH) δ: | 5.60 (bs, IH), 3.71–3.74 (d, 1H, J=12Hz), 3.61–3.64 (d, 1H, J=12Hz), 3.01 (s, 1H), 2.28–2.35 (m, 7H), 1.30 (m, 1H), 0.83–1.06 (m, 3H), 0.67–.0.82 (m, 10H); |
| IR (Neat, Cm$^{-1}$): | 2931, 2497, 1654 |

EXAMPLE-38

1-[1-Oxo-2-(4-methylcyclohexyl)hydrazino]ethyl-2-cyanopyrrolidine trifluoroacetate (Compound No. 37)

| | |
|---|---|
| Yield: | 50%. |
| Mass: | 265 (M$^+$ + 1), 287 (M$^+$ + Na); |
| $^1$HNMR (d$_4$-McOH) δ: | 4.84 (bs, 1H), 4.01–4.03 (m, 2H), 3.66–3.70 (m, 1H), 3.50–3.53 (m, 1H), 2.26–2.29 (m, 2H), 2.18–2.22 (m, 2H), 1.74–1.77 (m, 6H), 1.51–1.58 (m, 4H), 0.99–1.01 (d, 3H, J=8Hz); |
| IR (KBr, Cm$^{-1}$): | 3169, 2917, 2240, 1673 |

EXAMPLE-39

1-[1-Oxo-2-(1-cyclohexyl-2-isopropyl)hydrazino]ethyl-2-cyano pyrrolidine (Compound No. 38)

| | |
|---|---|
| Yield: | 30%. |
| Mass: | 293 ($M^+ + 1$), 315 ($M^+ + Na$); |
| $^1$HNMR (CDCl$_3$) δ: | 4.75 (bs, 1H), 3.85–3.87 (m, 1H), 3.64–3.71 (m, 2H), 3.29–3.35 (m, 3H), 2.83–2.90 (m, 2H), 2.61–2.65 (m, 2H), 2.11–2.22 (m, 6H), 1.78–1.88 (m, 4H), 0.96–0.98 (d, 6H, J=8Hz); |
| IR(Neat, Cm$^{-1}$): | 3263, 2924, 2241, 1645 |

EXAMPLE-40

1-[1-Oxo-2-(1-(4-methylcyclohexylmethyl)hydrazino)]ethyl-2-cyanopyrrolidine trifluoroacetate (Compound No. 39)

| | |
|---|---|
| Yield: | 5%. |
| Mass: | 279 ($M^+ + 1$), 301 ($M^+ + Na$); |
| $^1$HNMR (CDCl$_3$) δ: | 4.79 (bS, 1H), 3.96–3.98 (m, 1H), 3.53–3.61 (m, 2H), 3.06–3.10 (m, 1H), 2.25–2.29 (m, 3H), 1.84–1.88 (m, 1H), 1.72–1.75 (m, 1H), 1.51–1.55 (m, 4H), 1.35–1.37 (m, 1H), 1.22–1.35 (m, 4H), 0.89–0.96 (m, 5H); |
| IR (Neat, Cm$^{-1}$): | 2856, 2248, 1669, 1513 |

EXAMPLE-41

1-[1-Oxo-2-(4-chlorophenyl)hydrazino]ethyl-2-cyanopyrrolidine trifluoroacetate (Compound No. 40)

| | |
|---|---|
| Yield: | 35.3%. |
| Mass: | 279 ($M^+ + 1$), 301 ($M^+ + Na$); |
| $^1$HNMR (CDCl$_3$) δ: | 7.16–7.18 (d, 2H, J=8Hz), 6.86–6.88 (d, 2H, J=8Hz), 4.76 (bs, 1H), 3.55–3.84 (m, 4H), 2.11–2.33 (m, 4H); |
| IR (Neat, Cm$^{-1}$): | 2244, 1650, 1597 |

EXAMPLE-42

1-[1-Oxo-2-isopropyl-2-hydrazino]ethyl-2-cyano pyrrolidine trifluoroacetate (Compound No. 41)

| | |
|---|---|
| Yield: | 66.6%. |
| Mass: | 211 ($M^+ + 1$), 233 ($M^+ + Na$); |
| $^1$HNMR (d$_4$-MeOH) δ: | 5.01 (bs, 1H), 3.62–3.64 (m, 1H), 3.60–3.61 (m, 1H), 2.28–2.31 (m, 2H), 2.08–2.18 (m, 4H), 0.99–1.01 (d, 6H, J=8Hz); |
| IR (Neat, Cm$^{-1}$): | 2877, 2251, 1651, 1555 |

EXAMPLE-43

3-[1-Oxo-2-(1-(4-methylcyclohexyl)-2-ethyl)hydrazino]ethyl-4-cyanothiazolidine trifluoroacetate (Compound No. 42)

| | |
|---|---|
| Yield | 21.8%. |
| Mass | 311 ($M^+ + 1$), 333 ($M^+ + Na$); |
| $^1$HNMR (CDCl$_3$) δ | 5.31–5.33 (bs, 1H), 4.70–4.72 (d, 1H, J=8Hz), 4.63–4.65 (d, 1H, J=8Hz), 4.02–4.15 (m, 2H), 3.30–3.42 (m, 4H), 2.14–3.12 (m, 3H), 1.82–1.90 (m, 5H), 1.32–1.42 (m, 3H), 1.05–1.08 (m, 2H), 0.92–0.94 (d, 3H, J=8Hz); |
| IR (KBr, Cm$^{-1}$) | 3470, 3403, 2340, 1665, 1630. |

EXAMPLE-44

3-[1-Oxo-2-(1-(4-morpholinocarbonyl)hydrazino)ethyl]-4-cyanothiazolidine trifluoroacetate (Compound No. 43)

| | |
|---|---|
| Yield | 10.5%. |
| Mass | 300 ($M^+ + 1$), 322 ($M^+ + Na$); |
| $^1$HNMR (CDCl$_3$) δ | 4.62 (bs, 1H), 3.68–3.72 (m, 5H), 3.44–3.55 (m, 2H), 3.18–3.40 (m, 7H) |
| IR (KBr, Cm$^{-1}$) | 2828, 1670, 1429 |

EXAMPLE-45

3-[1-Oxo-2-(1-(4-methylcyclohexyl)-2-isopropyl)hydrazino]ethyl-4-cyanothiazolidine trifluoroacetate (Compound No. 44)

| | |
|---|---|
| Yield | 40%. |
| Mass | 325 ($M^+ + 1$); |
| $^1$HNMR (CDCl$_3$) δ | 5.28 (bs, 1H), 4.57–4.59 (m, 2H), 3.88–4.10 (dd, 2H, J=16Hz, 16Hz), 3.60–3.63 (t, 1H, J=6Hz), 3.22–3.33 (m, 2H), 1.96–2.08 (m, 2H), 1.80–1.83 (m, 2H), 1.41–1.44 (t, 6H, J=5.5Hz), 1.27–1.37 (m, 4H), 1.01–1.06 (m, 2H), 0.87–0.90 (d, 3H, J=11Hz); |
| IR (Neat, Cm$^{-1}$ | 2249, 1673, 1560 |

EXAMPLE-46

1-[1-Oxo-2-[(1-cyclohexyl)-2-(2-cyano-1-pyrrolidino acetyl)]hydrazino]ethyl-2-cyanopyrrolidine trifluoroacetate (Compound No. 45)

| | |
|---|---|
| Yield | 66.6%. |
| Mass | 385 ($M^+ - 1$); |
| $^1$HNMR (CDCl$_3$) δ | 4.84 (bs, 1H), 4.76 (bs, 1H), 4.05–4.19 (m, 4H), 3.98–4.01 (m, 1H), 3.80–3.87 (m, 1H), 3.61–3.68 (m, 7H), 1.42–4.48 (m, 6H), 1.31–1.34 (m, 8H); |
| IR (Neat, Cm$^{-1}$) | 2933, 2239, 1669, 1609, 1534. |

EXAMPLE-47

3-[1-Oxo-2-(1,2-bis-(2-(2-pyridyl)ethylaminocarbonyl)hydrazino)]ethyl-4-cyano thiazolidine bis trifluoroacetate (Compound No. 46)

| | |
|---|---|
| Yield | 96%. |
| Mass | 483 (M⁺ + 1), 505 (M⁺ + Na); |
| ¹HNMR (d₄-MeOH) δ | 8.71–8.75 (dd, 2H, J=8Hz, 8Hz), 8.44–8.52 (m, 2H), 7.85–7.99 (m, 4H), 5.25 (bs, 1H), 4.56–4.58 (d, 1H, J=8.5Hz), 3.94–3.99 (dd, 1H, J=9Hz, 9Hz), 3.61–3.66 (m, 4H), 3.36–3.39 (m, 3H), 3.22–3.26 (m, 5H); |
| IR (Neat, Cm⁻¹) | 2362, 1673, 1524 |

EXAMPLE-48

3-[1-Oxo-2-(1-(4-tert-butyl cyclohexyl)hydrazino)]ethyl-4-cyanothiazolidine trifluoro acetate (Compound No. 47)

| | |
|---|---|
| Yield | 82.2%. |
| Mass | 325 (M⁺ + 1), 347 (M⁺ + Na); |
| ¹HNMR (d₄-MeOH) δ | 5.33–5.36 (t, 1H, J=4Hz), 4.72–4.74 (d, 1H, J=8Hz), 4.63–4.65 (d, 1H, J=8Hz), 4.06–4.09 (m, 2H), 3.47–3.51 (m, 1H), 3.36–3.40 (m, 2H), 1.95–2.10 (m, 4H), 1.04–1.21 (m, 5H), 0.90 (s, 9H); |
| IR (KBr, Cm⁻¹) | 3025, 2964, 2207, 1678, 1610. |

EXAMPLE-49

1-[1-Oxo-2-(1-tetralinyl)hydrazino]ethyl-2-cyanopyrrolidine trifluoroacetate (Compound No. 48)

| | |
|---|---|
| Yield | 69.4%. |
| Mass | 299 (M⁺ + 1), 321 (M⁺ + Na); |
| ¹HNMR (CDCl₃) δ | 7.47–7.51 (d, 1H, J=14Hz), 7.33–7.35 (d, 1H, J=8Hz), 7.19–17.21 (d, 2H, J=8Hz), 4.71 (bs, 1H), 3.74–4.00 (m, 3H), 3.42–3.55 (m, 3H), 2.77–2.92 (m, 2H), 2.05–2.21 (m, 7H); |
| IR (Neat, Cm⁻¹) | 3414, 2950, 2246, 1675 |

EXAMPLE-50

3-[1-Oxo-2-(1-(4-tertbutylcyclohexyl)hydrazino)]ethyl-4-cyanothiazolidine trifluoroacetate (Compound No. 49)

| | |
|---|---|
| Yield | 71%. |
| Mass | 325 (M⁺ + 1), 347 (M⁺ + Na); |
| ¹HNMR (d4-MeOH) δ | 5.32–5.34 (t, 1H, J=4Hz), 4.67–4.74 (dd, 2H, J=8Hz, 8Hz), 4.08–4.11 (d, 2H, J=12Hz), 3.47–3.51 (m, 1H), 3.37–3.38 (d, 2H, J=4Hz), 1.95–2.05 (m, 2H), 1.57–1.60 (m, 4H), 1.32–1.38 (m, 3H), 0.90 (s, 9H); |
| IR (KBr, Cm⁻¹) | 2942, 2867, 2247, 1662, 1498. |

EXAMPLE-51

1-[1-Oxo-2-(1-cyclohexyl)-2-(4-cyano-3-thiazolidino acetyl)]hydrazino]ethyl-2-cyano pyrrolidine (Compound No. 50)

| | |
|---|---|
| Yield | 17.7%. |
| Mass | 403 (M⁺ − 1); |
| ¹HNMR (CDCl₃) δ | 5.32 (bs, 1H), 4.71–4.87 (m, 3H), 4.11–4.23 (m, 2H), 3.75–3.79 (m, 2H), 3.51–3.64 (m, 4H), 3.27–3.36 (m, 4H), 1.86–1.90 (m, 2H), 1.77–180 (m, 4H), 1.30–1.35 (m, 5H); |
| IR (Neat, Cm⁻¹) | 2936, 2247, 1675, 1540. |

EXAMPLE-52

3-[1-Oxo-2-(1-isopropyl-4-piperidinyl)hydrazino)]ethyl-4-cyano thiazolidine trifluoroacetate (Compound No. 51)

| | |
|---|---|
| Yield | 43.9%. |
| Mass | 312 (M⁺ + 1); |
| ¹HNMR (d6-DMSO) δ | 5.32 (bS, 1H), 4.58–4.80 (m, 4H), 4.28–4.49 (m, 2H), 3.93–4.05 (m, 4H), 2.99–3.01 (m, 2H), 1.24–1.25 (d, 6H, J=6Hz); |
| IR (KBr, Cm⁻¹) | 2934, 2245, 1669, 1512. |

EXAMPLE-53

3-[1-Oxo-2-(1-(1-(4-cyanophenylmethyl)-piperidin-4-yl)hydrazino)]ethyl-4-cyanothiazolidine bis trifluoroacetate (Compound No. 52)

| | |
|---|---|
| Yield | 55%. |
| Mass | 385 (M⁺ + 1); |
| ¹HNMR (d₄-MeOH) δ | 7.88–7.90 (d, 2H, J=8Hz), 7.71–7.73 (d, 2H, J=8Hz), 5.31–.533 (t, 1H, J=4Hz), 4.77–4.78 (d, 1H, J=8Hz), 4.70–4.72 (d, 1H, J=8Hz), 4.41–4.44 (m, 3H), 4.0–4.12 (m, 1H), 3.46–3.53 (m, 4H), 3.37–3.39 (m, 3H), 1.42–1.46 (m, 4H); |
| IR (Neat, Cm⁻¹) | 3416, 2946, 2234, 1676, 1541. |

EXAMPLE-54

3-[1-Oxo-2-[1-(4-methylcyclohexyl)-2-(1-(3-pyridinylmethyl)-4-piperidinyl)]hydrazino]ethyl-4-cyanothiazolidine (Compound No. 53)

| | |
|---|---|
| Yield | 45.7%. |
| Mass | 457 (M$^+$ + 1), 479 (M$^+$ + Na); |
| $^1$HNMR (d$_4$-MeOH) δ | 8.70–8.72 (d, 2H, J=8Hz), 8.04–8.09 (t, 1H, J=9Hz), 7.59–7.61 (t, 1H, J=4Hz), 5.25–5.28 (t, 1H, J=4.5Hz), 4.68–4.70 (d, 1H, J=8Hz), 4.35–4.45 (m, 2H), 3.38-3.71 (m, 4H), 3.01–3.09 (m, 3H), 1.70–1.86 (m, 6H), 1.22–1.36 (m, 11H), 0.88–0.90 (d, 3H, J=8Hz); |
| IR (Neat, Cm$^{-1}$) | 3418, 2925, 2246, 1651 |

EXAMPLE-55

3-[1-Oxo-2-[1-(4-methylcyclohexyl)-2-(1-isopropyl-4-piperidinyl)]hydrazino]ethyl-4-cyanothiazolidine (Compound No. 54)

| | |
|---|---|
| Yield | 36%. |
| Mass | 408 (M$^+$ + 1); |
| $^1$HNMR (CDCl$_3$) δ | 5.23 (bs, 1H), 4.76–4.78 (d, 1H, J=8Hz), 4.68–4.70 (d, 1H, J=8Hz), 4.51-4.53 (d, 1H, J=8Hz), 3.47–3.52 (m, 1H), 3.30–3.37 (m, 4H), 3.10–3.17 (m, 2H), 2.90–2.94 (m, 2H), 2.75–2.78 (m, 1H), 2.64–2.68 (m, 1H), 2.33–2.36 (m, 1H), 2.03–2.11 (m, 2H), 1.75-1.86 (m, 5H), 1.41–1.43 (d, 3H, J=8Hz), 1.38–1.40 (d, 3H, J=8Hz), 1.12–1.22 (m, 4H), 0.89–0.91 (d, 3H, J=8Hz); |
| IR (Neat, Cm$^-$) | 3423, 2931, 2340, 1636 |

EXAMPLE-56

3-[1-Oxo-2-(1-(1-(4-methylphenylsulphonyl)-4-piperidinyl)-hydrazino)]ethyl-4-cyanothiazolidine trifluoroacetate (Compound No. 55)

| | |
|---|---|
| Yield | 65.5%. |
| Mass | 424 (M$^+$ + 1), 446 (M$^+$ + Na); |
| $^1$HNMR (d$_4$-MeOH) δ | 7.67–7.69 (d, 2H, J=8Hz), 7.44–7.46 (d, 2H, J=8Hz), 5.29–5.31 (t, 1H, J=4Hz), 4.67–4.69 (d, 1H, J=8Hz), 4.60–4.62 (d, 1H, J=8Hz), 3.99–4.01 (d, 2H, J=8Hz), 3.75–3.78 (m, 2H), 3.36–3.37 (d, 2H, J=8Hz), 3.10–3.16 (m, 1H), 2.46 (s, 3H), 2.38–2.41 (m, 2H), 1.98–2.01 (m, 2H), 1.62–1.72 (m, 2H); |
| IR (KBr, Cm$^{-1}$) | 3464, 2842, 2111, 1672, 1606 |

EXAMPLE-57

3-[1-Oxo-2-[1-methyl-2-(1-(4-methylphenylsulphonyl)-piperidin-4-yl)]hydrazino]ethyl-4-cyanothiazolidine trifluoroacetate (Compound No. 56)

| | |
|---|---|
| Yield | 16%. |
| Mass | 438 (M$^+$ + 1), 460 (M$^+$ + Na); |
| $^1$HNMR (CDCl$_3$) δ | 7.65–7.67 (d, 2H, J=8Hz), 7.33–7.35 (d, 2H, J=8Hz), 5.24–5.26 (t, 1H, J=4Hz), 4.68–4.70 (d, 1H, J=8Hz), 4.58–4.60 (d, 1H, J=8Hz), 3.49–3.57 (m, 5H), 3.26–3.27 (t, 1H, J=9Hz), 2.56–2.60 (m, 6H), 2.46 (s, 6H); |
| IR (Neat, Cm$^{-1}$) | 3424, 2939, 2251, 1666, 1599. |

EXAMPLE-58

3-[1-Oxo-2-(1-(1-(3-pyridinemethyl)-4-piperidinyl) hydrazino)]ethyl-4-cyanothiazolidine tris-trifluoroacetate (Compound No. 57)

| | |
|---|---|
| Yield | 68.2%. |
| Mass | 361 (M$^+$ + 1); |
| $^1$HNMR (d$_4$-MeOH) δ | 8.98–9.00 (d, 2H, J=8Hz), 8.72–8.74 (d, 1H, J=8Hz), 8.23–8.29 (dd, 1H, J=8Hz, 8Hz), 4.74–4.78 (t, 1H, J=8Hz), 4.32–4.35 (d, 1H, J=8Hz), 4.23–4.25 (d, 1H, J=8Hz), 3.42–3.70 (m, 5H), 3.02–3.10 (m, 6H), 2.17–2.20 (m, 4H); |
| IR (Neat, Cm$^{-1}$) | 3392, 2949, 2250, 1676. |

EXAMPLE-59

3-[1-Oxo-2-[1-methyl-2-(1-(4-cyanophenylmethyl) piperidin-4-yl)]hydrazino]ethyl-4-cyanothiazolidine bis-trifluoroacetate (Compound No. 58)

| | |
|---|---|
| Yield | 33.6%. |
| Mass | 399 (M$^+$ + 1); |
| $^1$HNMR (d$_4$-MeOH) δ | 7.87–7.89 (d, 2H, J=8Hz), 7.69–7.71 (d, 2H, J=8Hz), 5.25–5.27 (t, 1H, J=4Hz), 4.69–4.71 (d, 2H, J=8Hz), 4.35–4.39 (m, 2H), 3.49–3.64 (m, 4H), 3.06–3.22 (m, 2H), 3.02–3.04 (m, 1H), 2.49–2.58 (m, 2H), 1.35 (s, 3H); |
| IR (CCl$_4$, Cm$^{-1}$) | 3354, 2236, 1678. |

EXAMPLE-60

3-[1-Oxo-2-[1-methyl-2-(1-(3-pyridinylmethyl)-piperidin-4-yl)]hydrazino]ethyl-4-cyanothiazolidine tris-trifluoroacetate (Compound No. 59)

| | |
|---|---|
| Yield | 32.7%. |
| Mass | 375 (M$^+$ + 1); |

-continued

| | |
|---|---|
| ¹HNMR (CDCl₃) δ | 8.70–8.72 (d, 2H, J=8Hz), 8.04–8.08 (t, 1H, J=8Hz), 7.59–7.61 (t, 1H, J=8Hz), 5.25–5.27 (t, 1H, J=4Hz), 4.68–4.70 (d, 1H, J=8Hz), 4.35–4.43 (m, 3H), 3.51–3.71 (m, 2H), 3.09–3.15 (m, 3H), 2.01–2.03 (m, 4H), 1.36 (s, 3H); |
| IR (CCl₄, Cm⁻¹) | 3358, 2142, 1678. |

EXAMPLE-61

3-[1-Oxo-2-(1-(4-n-propylcyclohexyl)hydrazino)]ethyl-4-cyanothiazolidine trifluoro acetate (Compound No. 60)

| | |
|---|---|
| Yield | 97.5%. |
| Mass | 311 (M⁺ + 1), 333 (M⁺ + Na); |
| ¹HNMR (d₄-MeOH) δ | 5.33–5.35 (t, 1H, J=4Hz), 4.72–4.74 (d, 1H, J=8Hz), 4.64–4.68 (d, 1H, J=8Hz), 4.05–4.20 (m, 2H), 3.38–3.47 (m, 3H), 1.70–1.74 (m, 5H), 1.52–1.60 (m, 4H), 1.33–1.39 (m, 4H), 0.92–0.96 (t, 3H, J=8Hz); |
| IR (KBr, Cm⁻¹) | 3461, 2942, 2117, 1670, 1640. |

EXAMPLE-62

3-[1-Oxo-2-(1-(1-(4-nitrophenylmethyl)-piperidin-4-yl)hydrazino]ethyl-4-cyanothiazolidine trifluoroacetate (Compound No. 61)

| | |
|---|---|
| Yield | 56%. |
| Mass | 405 (M⁺ + 1); |
| ¹HNMR (d₄-MeOH) δ | 8.35–8.37 (d, 2H, J=8Hz), 1.77–1.79 (d, 2H, J=8Hz), 5.31–5.33 (t, 1H, J=4Hz), 4.78–4.80 (d, 1H, J=8Hz), 4.63–4.65 (d, 1H, J=8Hz), 4.45 (s, 2H), 3.44–3.50 (m, 3H), 3.37–3.38 (m, 4H), 3.11–3.15 (m, 2H), 188–2.20 (m, 4H); |
| IR (KBr, Cm⁻¹) | 2939, 2679 and 1652 |

EXAMPLE-63

3-[1-Oxo-2-[1-(1-(4-chlorophenylsulphonyl)-piperidin-4-yl)]hydrazino]ethyl-4-cyanothiazolidine trifluoroacetate (Compound No. 62)

| | |
|---|---|
| Yield | 55.5%. |
| Mass | 444 (M⁺ + 1); |
| ¹HNMR (d₄-MeOH) δ | 7.78–7.80 (d, 2H, J=8Hz), 7.65–7.67 (d, 2H, J=8Hz), 5.29–5.31 (t, 1H, J=4Hz), 4.68–4.70 (d, 1H, J=8Hz), 4.60–4.62 (d, 1H, J=8Hz), 4.00–4.01 (d, 1H, J=8Hz), 3.77–3.81 (dd, 2H, J=4Hz, 6Hz), 3.31–3.36 (m, 2H), 3.06–3.18 (m, 2H), 2.44–2.49 (m, 2H), 1.99–2.05 (m, 2H), 1.65–1.72 (m, 2H); |
| IR (KBr, Cm⁻¹) | 3171, 2357, 1674, 1605, 1534, 1440 |

EXAMPLE-64

3-[1-Oxo-2-(1-(1-norcamphoranyl)hydrazino)]ethyl-4-cyanothiazolidine trifluoroacetate (Compound No. 63)

| | |
|---|---|
| Yield | 58.3%. |
| Mass | 281 (M⁺ + 1), 303 (M⁺ + Na); |
| ¹HNMR (d₄-MeOH) δ | 5.33–5.35 (t, 1H, J=4Hz), 4.71–4.72 (d, 1H, J=6Hz), 4.64–4.65 (d, 1H, J=6Hz), 3.93–3.97 (dd, 2H, J=4Hz, 8Hz), 3.50–3.54 (m, 2H), 3.37–3.39 (d, 2H, J=6Hz), 2.38–2.40 (m, 1H), 2.28–2.32 (m, 1H), 1.78–1.88 (m, 2H), 1.60–1.63 (m, 1H), 1.42–1.54 (m, 4H); |
| IR (KBr, Cm⁻¹) | 2950, 216, 1675, 1628, 1511. |

EXAMPLE-65

3-[1-Oxo-2-(1-(4-n-propylcyclohexyl)hydrazino)]ethyl-4-cyanothiazolidine trifluoroacetate (Compound No. 64)

| | |
|---|---|
| Yield | 85.3%. |
| Mass | 311 (M⁺ + 1); |
| ¹HNMR (d₄-MeOH) δ | 5.33–5.35 (t, 1H, J=4Hz), 4.71–4.73 (d, 1H, J=8Hz), 4.63–4.65 (d, 1H, J=8Hz), 4.11–4.16 (m, 1H), 3.38–3.39 (d, 2H, J=4Hz), 3.12–3.16 (m, 1H), 1.92–2.05 (m, 4H), 1.39–1.41 (m, 1H), 1.32–1.38 (m, 4H), 1.20–123 (m, 3H), 0.90–0.94 (t, 3H, J=8Hz); |
| IR (KBr, Cm⁻¹) | 3496, 2328, 1667, 1551. |

EXAMPLE-66

3-[1-Oxo-2-[1-(1-(4-methylcyclohexyl carbonyl)-piperidin-4-yl)]hydrazino]ethyl-4-cyanothiazolidine trifluoroacetate (Compound No. 65)

| | |
|---|---|
| Yield | 61%. |
| Mass | 394 (M⁺ + 1), 416 (M⁺ + Na); |
| ¹HNMR (CDCl₃) δ | 5.31–5.33 (t, 1H, J=4Hz), 4.68–4.70 (d, 1H, J=8Hz), 4.52–4.54 (d, 1H, J=8Hz), 4.01–4.05 (m, 4H), 3.51–3.63 (m, 5H), 2.56–2.68 (m, 2H), 2.11–2.20 (m, 2H), 1.71–1.80 (m, 4H), 1.44–1.53 (m, 6H), 0.90–0.92 (m, 3H; J=8Hz); |
| IR (CCl₄, Cm⁻¹) | 3372, 2944, 2240, 1679. |

EXAMPLE-67

3-[1-Oxo-2-(1-(1-acetyl)-piperidin-4-yl)hydrazino]ethyl-4-cyanothiazolidine trifluoroacetate (Compound No. 66)

| | |
|---|---|
| Yield | 43%. |
| Mass | 312 (M⁺ + 1), 334 (M⁺ + Na); |
| ¹HNMR (d₄-MeOH) δ | 5.32–5.35 (t, 1H, J=4Hz), 4.71–4.73 |

-continued

| | |
|---|---|
| | (d, 1H, J=8Hz), 4.64–4.66 (d, 1H, J=8Hz), 4.54–4.57 (m, 1H), 4.05–4.15 (m, 2H), 3.38–3.51 (m, 4H), 3.15–3.19 (m, 1H), 2.70–2.83 (m, 1H), 2.13 (s, 3H), 1.97–2.05 (m, 2H), 1.44–1.55 (m, 1H), 1.24–1.29 (m, 1H); |
| IR (Neat, $Cm^{-1}$) | 2922, 1680 and 1651 |

EXAMPLE-68

1,1-Dioxo-3-[1-oxo-2-(1-(4-methylcyclohexyl)hydrazino)]ethyl-4-cyanothiazolidine trifluoroacetate (Compound No. 67)

| | |
|---|---|
| Yield | 70.5%. |
| Mass | 315 ($M^+ + 1$), 337 ($M^+ + Na$); |
| 1HNMR (CDCl3) δ | 5.62–5.65 (dd, 1H, J=4Hz, J=4Hz), 4.95–4.97 (d, 1H, J=8.Hz), 4.73–4.75 (d, 1H, J=8Hz), 3.97–4.08 (m, 2H), 3.79–3.93 (m, 2H), 3.11–3.15 (m, 1H), 1.98–2.05 (m, 2H), 1.85–1.89 (dd, 2H, J=4Hz, 4Hz), 1.36–1.41 (m, 3H), 1.0–1.09 (m, 2H), 0.93–0.95 (d, 3H, J=8Hz); |
| IR (Neat, $Cm^{-1}$) | 3398, 2252, 1678, 1530. |

EXAMPLE-69

3-[1-Oxo-2-(1-methyl-2-(4-methylcyclohexyl)hydrazino)]ethyl-4-cyanothiazolidine (Compound No. 68)

| | |
|---|---|
| Yield | 15%. |
| Mass | 297 ($M^+ + 1$), 319 ($M^+ +Na$); |
| $^1$HNMR (CDCl$_3$) δ | 5.32 (bs, 1H), 4.64–4.66 (d, 1H, J=8Hz), 4.61–4.63 (d, 1H, J=1Hz), 3.51 (s, 3H), 3.32–3.36 (m, 3H), 2.96–2.99 (m, 1H), 2.84–2.87 (m, 1H), 2.03–2.06 (m, 1H), 1.92–1.94 (m, 1H), 1.23–1.36 (m, 5H), 1.03–1.11 (m, 2H), 0.94–0.96 (d, 3H, J=8Hz); |
| IR (Neat, $Cm^{-1}$) | 3302, 2923, 2244, 1667. |

EXAMPLE-70

3-[1-Oxo-2-(1-methyl-2-(4-methylcyclohexyl)hydrazino)]ethyl-4-cyanothiazolidine (Compound No. 69)

| | |
|---|---|
| Yield | 15%. |
| Mass | 297 ($M^+ + 1$), 319 ($M^+ + Na$); |
| $^1$HNMR (d$_4$-MeOH) δ | 5.26–5.28 (t, 1H, J=4Hz), 4.75–4.77 (d, 1H, J=8Hz), 4.57–4.59 (d, 1H, J=8Hz), 3.41–3.50 (m, 2H), 2.64–2.67 (m, 1H), 2.54–2.60 (m, 2H), 2.19 (s, 3H), 1.85–1.88 (m, 2H), 1.70–1.73 (m, 2H), 1.28–1.32 (m, 2H), 1.03–1.12 (m, 3H), 0.89–0.91 (d, 3H, J=8Hz); |
| IR (Neat, $Cm^{-1}$) | 3421, 2244, 1660. |

EXAMPLE-71

3-[1-Oxo-2-(1-(1-(2,3-dichlorophenyl carbonyl)-piperidin-4-yl)hydrazino)]ethyl-4-cyanothiazolidine trifluoroacetate (Compound No. 70)

| | |
|---|---|
| Yield | 60%. |
| Mass | 442 ($M^+ + 1$), 464 ($M^+ + Na$); |
| $^1$HNMR (d$_4$-MeOH) δ | 7.65–7.68 (dd, 1H, J=4Hz, 4Hz) 7.42–7.45 (dd, 1H, J=4Hz, 4Hz), 7.31–7.35 (dd, 1H, J=4Hz) 4Hz), 5.34 (bs, 1H), 4.71–4.73 (d, 1H, J=8Hz), 4.62–4.64 (d, 1H, J=8Hz), 4.02–4.08 (m, 1H), 3.25–3.53 (m, 4H), 2.84–3.15 (m, 3H), 2.07–2.13 (m, 1H), 1.88–1.95 (m, 1H), 1.62–1.65 (m, 1H), 1.48–1.51 (m, 1H), 1.21–1.31 (m, 1H); |
| IR (Neat, $Cm^{-1}$) | 3351, 2227, 1676, 1629. |

EXAMPLE-72

3-[1-Oxo-2-[1-methyl-2-(1-(4-chlorophenylsulphonyl)-piperidin-4-yl)]-hydrazino]ethyl-4-cyanothiazolidine (Compound No. 71)

| | |
|---|---|
| Yield | 23.5%. |
| Mass | 458 ($M^+ + 1$), 480 ($M^+ + Na$); |
| $^1$HNMR (CDCl$_3$) δ | 7.76–7.78 (d, 2H, J=8Hz), 7.62–7.64 (d, 2H, J=8Hz), 5.17–5.19 (t, 1H, J=4Hz), 4.83–4.85 (d, 1H, J=8Hz), 4.71–4.73 (d, 1H, J=8Hz), 4.63 (s, 1H), 4.51–4.57 (m, 1H), 3.66–3.69 (d, 1H, J=12Hz), 3.50–3.53 (m, 1H), 3.41–3.47 (m, 4H), 3.35–3.39 (m, 1H), 2.52 (s, 3H), 1.84–1.88 (m, 2H), 1.43–1.47 (m, 2H); |
| IR (Neat, $Cm^{-1}$) | 2943, 2240, 1728, 1666, 1584. |

EXAMPLE-73

3-[1-Oxo-2-(1-(4-piperidinyl)hydrazino)]ethyl-4-cyanothiazolidine bis-trifluoroacetate (Compound No. 72)

| | |
|---|---|
| Yield | 52.8%. |
| Mass | 270 ($M^+ + 1$); |
| $^1$HNMR (d$_4$-MeOH) δ | 5.32–5.34 (t, 1H, J=4Hz), 4.74–4.76 (d, 1H, J=8Hz), 4.62–4.64 (d, 1H, J=8Hz), 3.36–3.53 (m, 8H), 2.17–2.21 (m, 3H), 1.77–1.86 (m, 2H); |
| IR (Neat, $Cm^{-1}$) | 3394, 2250, 1679. |

EXAMPLE-74

[1-Oxo-2-(1-(1-(4-chlorophenylsulphonyl)-piperidin-4-yl)-hydrazino)]ethyl-2-cyanopyrrolidine trifluoroacetate (Compound No. 73)

| | |
|---|---|
| Yield | 67%. |
| Mass | 426 ($M^+ + 1$), 448 ($M^+ + Na$); |

-continued

| | |
|---|---|
| ¹HNMR (d₄-MeOH) δ | 7.78–7.80 (d, 2H, J=8Hz), 7.65–7.67 (d, 2H, J=8Hz), 4.79–4.81 (t, 1H, J=4Hz), 3.92 (s, 2H), 3.79–3.82 (m, 2H), 3.62–3.66 (m, 1H), 3.47–3.51 (m, 1H), 3.14–3.17 (m, 1H), 2.43–2.49 (t, 2H, J=8Hz), 2.16–2.29 (m, 4H), 2.01–2.03 (d, 2H, J=8Hz), 1.61–1.68 (m, 2H); |
| IR (KBr, Cm⁻¹) | 3415, 2332, 1663, 1580. |

EXAMPLE-75

3-[1-Oxo-2-(1-(4-methylcyclohexyl)-2-acetyl)hydrazino]ethyl-4-cyanothiazolidine (Compound No. 74)

| | |
|---|---|
| Yield | 47.6%. |
| Mass | 325 (M⁺ + 1), 347 (M⁺ + Na); |
| ¹HNMR (CDCl₃) δ | 5.18–5.20 (t, 1H, J=4Hz), 4.76–4.78 (d, 1H, J=8Hz) 4.67–4.70 (d, 1H, J=9.6Hz), 4.56–4.58 (d, 1H, J=8Hz), 4.42–4.44 (d, 1H, J=9Hz), 3.96–3.99 (m, 1H), 3.81–3.92 (m, 1H), 3.77–3.81 (m, 2H), 3.52–3.55 (m, 2H), 3.30–3.35 (m, 4H), 2.85–2.92 (m, 1H), 2.63–2.67 (m, 1H), 1.89 (s, 3H), 0.90–0.92 (d, 3H, J=8Hz); |
| IR (Neat, Cm⁻¹) | 3343, 2248, 1676, 1570. |

EXAMPLE-76

3-[1-Oxo-2-(1-(1-adamantanyl)hydrazino)]ethyl-4-cyanothiazolidine trifluoroacetate (Compound No. 75)

| | |
|---|---|
| Yield | 38.9%. |
| Mass | 321 (M⁺+1), 343 (M⁺+Na); |
| ¹HNMR (d₄-MeOH) δ | 5.32–5.34 (t, 1H, J=4Hz), 4.70–4.72 (d, 1H, J=8Hz), 4.61–4.63 (d, 1H, J=8Hz), 4.04–4.06 (d, 1H, J=8Hz), 3.53 (bs, 1H), 3.47–3.50 (m, 1H), 3.37–3.38 (d, 2H, J=4Hz), 1.92–2.12 (m, 6H), 1.85–1.94 (m, 2H), 1.76–1.82 (m, 4H), 1.58–1.61 (m, 2H); |
| IR (KBr, Cm⁻¹) | 2927, 2242, 1663, 1508. |

EXAMPLE-77

3-[1-Oxo-2-(1-(1-(tert-butyl carbonyl)-piperidin-4-yl)hydrazino)]ethyl-4-cyanothiazolidine trifluoroacetate (Compound No. 76)

| | |
|---|---|
| Yield | 76.4%. |
| Mass | 354 (M⁺ + 1), 376 (M⁺ + Na); |
| ¹HNMR (d₄-MeOH) δ | 5.33–5.35 (t, 1H, J=4Hz), 4.76–4.78 (d, 1H, J=8Hz), 4.63–4.65 (d, 1H, J=8Hz), 4.47–4.50 (d, 2H, J=12Hz), 4.08–4.10 (d, 2H, J=8Hz), 3.33–3.53 (m, 5H), 2.01–2.03 (m, 2H), 1.48–1.54 (m, 2H), 1.30 (s, 9H); |
| IR (KBr, Cm⁻¹) | 3427, 2248, 1673, 1614. |

EXAMPLE-78

3-[1-Oxo-2-(1-(1-(5-trifluoromethyl-2-pyridinyl)-piperidin-4-yl)hydrazino)]ethyl-4-cyano thiazolidine bis trifluoroacetate (Compound No. 77)

| | |
|---|---|
| Yield | 63.3%. |
| Mass | 415 (M⁺ + 1), 437 (M⁺+ Na); |
| ¹HNMR (d₄-MeOH) δ | 8.36 (s, 1H), 7.73–7.77 (dd, 1H, J=4Hz, 8Hz), 6.94–6.96(d, 1H, J=8Hz), 5.34–5.36 (t, 1H, J=4Hz), 4.71–4.73 (d, 1H, J=8Hz), 4.63–4.65 (d, 1H, J=8Hz), 4.54–4.58 (d, 2H, J=13Hz), 4.09–4.13 (t, 2H, J=8Hz), 3.36–3.40 (m, 1H), 3.01–3.04 (m, 3H), 2.03–2.07 (m, 2H), 1.58–1.62 (m, 2H); |
| IR (Neat, Cm⁻¹) | 2943, 2248 and 1672 |

EXAMPLE-79

3-[1-Oxo-2-(1-(1-methanesulphonylamino-4-cyclohexyl)hydrazino)]ethyl-4-cyanothiazolidine trifluoroacetate (Compound No. 78)

| | |
|---|---|
| Yield | 66.6%. |
| Mass | 362 (M⁺ + 1), 384 (M⁺ + Na); |
| ¹HNMR (d₄-MeOH) δ | 5.33–5.35 (t, 1H, J=4Hz), 4.73–4.75 (d, 1H, J=8Hz), 4.59–4.61 (d, 1H, J=8Hz), 4.02–4.14 (m, 2H), 3.19–3.24 (m, 4H), 2.97 (s, 3H), 2.14–2.17 (d, 2H, J=10Hz), 2.05–2.07 (d, 2H, J=8Hz), 1.36–1.44 (m, 4H); |
| IR (KBr, Cm⁻¹) | 2940, 2248, 1677, 1437. |

EXAMPLE-80

3-[1-Oxo-2-(1-(3,3,5-trimethyl cyclohexyl)-hydrazino)]ethyl-4-cyanothiazolidine trifluoroacetate (Compound No. 79)

| | |
|---|---|
| Yield | 48.5%. |
| Mass | 311 (M⁺ + 1); |
| ¹HNMR (d₄-MeOH) δ | 5.34 (bs, 1H), 4.73–4.75 (d, 1H, J=8Hz), 4.65–4.67 (d, 1H, J=8Hz), 4.04–4.14 (m, 2H), 3.61–3.64 (m, 1H), 3.38–3.39 (d, 2H, J=4Hz), 1.95–1.99 (m, 1H), 1.77–1.80 (m, 1H), 1.62–1.65 (m, 1H), 1.46–1.49 (m, 4H), 1.10–1.12 (d, 3H, J=8Hz), 0.99 (s, 6H); |
| IR (KBr, Cm⁻¹) | 3099, 2246, 1665, 1628, 1516. |

EXAMPLE-81

3-[1-Oxo-2-(1-isopropyl-2-ethyl)-hydrazino]-ethyl-4-cyanothiazolidine trifluoroacetate
(Compound No. 80)

| | |
|---|---|
| Yield | 97%. |
| Mass | 257 (M$^+$+ 1), 279 (M$^+$+ Na); |
| $^1$HNMR (CDCl$_3$) δ | 5.27 (bs, 1H), 4.71–4.73 (d, 1H, J=8Hz), 4.55–4.57 (d, 1H, J=8Hz), 3.84–3.90 (m, 2H), 3.66–3.69 (t, 1H, J=6Hz), 3.28–3.37 (m, 4H), 1.35–1.37 (t, 3H, J=4Hz), 1.26–1.27 (d, 6H, J=6Hz); |
| IR (Neat, Cm$^{-1}$) | 2983, 2251, 1670. |

EXAMPLE-82

3-[1-Oxo-2-[1-(1-phenylmethyl-piperidin-4-yl)]-hydrazino]-ethyl-4-cyanothiazolidine trifluoroacetate
(Compound No. 81)

| | |
|---|---|
| Yield | 56%. |
| Mass | 360 (M$^+$ + 1); |
| $^1$HNMR (d$_4$-MeOH) δ | 7.52 (bs, 5H), 5.43 (bs, 1H), 4.69–4.71 (d, 1H, J=8Hz), 4.61–4.63 (d, 1H, J=8Hz), 4.31–4.42 (m, 2H), 4.05–4.11 (m, 2H), 3.58–3.61 (m, 2H), 3.40–3.51 (m, 3H), 3.01–3.15 (m, 2H), 2.21–2.24 (m, 2H), 1.96–2.02 (m, 2H); |
| IR (Neat, Cm$^{-1}$) | 3411, 2249, 1675. |

EXAMPLE-83

3-[1-Oxo-2-(1-(1-(4-chlorophenyl sulphonylamino-4-cyclohexyl)hydrazino)]ethyl-4-cyanothiazolidine trifluoroacetate (Compound No. 82)

| | |
|---|---|
| Yield | 41%. |
| Mass | 458 (M$^+$ + 1), 480 (M$^+$ + Na); |
| $^1$HNMR (d$_4$-MeOH) δ | 7.85–7.87 (d, 2H, J=8Hz), 7.58–7.60 (d, 2H, J=8Hz), 5.31 (bs, 1H), 4.72–4.74 (d, 1H, J=8Hz), 4.60–4.62 (d, 1H, J=8Hz), 3.96–4.07 (m, 2H), 3.45–3.53 (m, 2H), 3.06–3.08 (m, 2H), 1.86–1.97 (m, 4H), 1.26–1.38 (m, 4H); |
| IR (KBr, Cm$^{-1}$) | 2943, 2240, 1673, 1435. |

EXAMPLE-84

3-[1-Oxo-2-(pyridazin-1-yl)]ethyl-4-cyanothiazolidine (Compound No. 83)

| | |
|---|---|
| Yield | 30%. |
| Mass | 241 (M$^+$ + 1); |
| $^1$HNMR (d$_4$-MeOH) δ | 5.25–5.27 (t, 1H, J=4Hz), 4.78–4.81 (d, 1H, J=10Hz), 4.72–4.74 (d, 1H, J=8Hz), 3.50–3.56 (m, 2H), 3.30–3.37 (m, 2H), 2.95–2.98 (t, 2H, J=5.5Hz), 2.72–2.83 (m, 2H), 1.25–1.34 (m, 4H); |
| IR (Neat, Cm$^{-1}$) | 2925, 2244, 1737, 1663. |

EXAMPLE-85

3-[1-Oxo-2-(1-(1-methanesulphonylamino-4-cyclohexyl)-2-isopropyl)hydrazino]ethyl-4-cyanothiazolidine trifluoroacetate (Compound No. 84)

| | |
|---|---|
| Yield | 75%. |
| Mass | 404 (M$^+$ + 1), 426 (M$^+$ + Na); |
| $^1$HNMR (d$_4$-MeOH) δ | 5.32–5.34 (t, 1H, J=4Hz), 4.79–4.81 (d, 1H, J=8Hz), 4.65–4.67 (d, 1H, J=8Hz), 4.03–4.13 (m, 2H), 3.57–3.59 (t, 1H, J=4Hz), 3.48–3.53 (q, 2H, J=8Hz), 3.38–3.39 (d, 2H, J=4Hz), 3.21–3.26 (m, 1H), 2.96–2.97 (d, 3H, J=6.5Hz), 2.11–2.14 (m, 2H), 1.98–2.04 (m, 2H), 1.71–1.80 (m, 2H), 1.44–1.50 (m, 2H), 1.35–1.37 (d, 6H, J=8Hz); |
| IR (KBr, Cm$^{-1}$) | 2945, 2245, 1676, 1435. |

EXAMPLE-86

3-[1-oxo-2-[1-(1(morpholinocarbonyl)-piperidin-4-yl)]hydrazino]ethyl-4-cyano-thiazolidine trifluoroacetate (Compound No. 85)

| | |
|---|---|
| Yield | 80% |
| Mass | 383 (M$^+$ + 1), 405 (M$^+$ + Na) |
| $^1$HNMR (d$_4$-MeOH) δ | 5.32–5.34 (t, 1H), 4.71–4.73 (d, 1H), 4.63–4.65 (d, 1H), 4.03–4.12 (m, 2H), 3.78–3.81 (m, 2H), 3.66–3.68 (t, 4H), 3.47–3.49 (m, 1H), 3.38–3.39 (d, 2H), 3.27–3.29 (t, 4H), 2.87–2.94 (t, 2H), 1.95–2.03 (m, 2H), 1.55–1.61 (m, 2H) |
| IR (KBr, cm$^{-1}$) | 2888, 2246, 1670, 1542 |

EXAMPLE-87

3-[1-oxo-2-[1-(1-(methylsulphonyl)-piperidin-4-yl)]hydrazino]ethyl-4-cyanothiazolidine trifluoroacetate (Compound No. 86)

| | |
|---|---|
| Yield | 70% |
| Mass | 348 (M$^+$ + 1) |
| $^1$HNMR (d$_4$-MeOH) δ | 5.32.–5.34 (t, 1H), 4.72–4.74 (d, 1H), 4.59–4.61 (d, 1H), 4.07–4.09 (m, 2H), 3.78–3.81 (m, 2H), 3.43–3.48 (m, 1H), 3.38–3.39 (d, 2H), 2.86 (S, 3H), 2.80–2.85 (m, 2H), 2.03–2.08 (m, 2H), 1.63–1.73 (m, 2H) |
| IR (KBr, cm$^{-1}$) | 3426, 2929, 2248, 2110, 1679 |

EXAMPLE-88

3-[1-oxo-2-[1-(1(methylsulphonyl)-piperidin-4-yl)-2-isopropyl]hydrazino]ethyl-4-cyanothiazolidine trifluoroacetate (Compound No. 87)

| | |
|---|---|
| Yield | 80% |
| Mass | 390 (M$^+$ + 1), 412 (M$^+$ + Na) |
| $^1$HNMR (d$_4$-MeOH) δ | 5.31–5.34 (t, 1H), 4.75–4.76 (d, 1H), 4.58–4.61 (d, 1H), 4.08–4.10 (d, 2H), 3.80–3.83 (m, 2H), 3.53–3.61 (m, 1H), 3.38–3.39 (d, 2H), 2.86 (S, 3H), 3.44–3.48 (m, 1H), 2.78–2.85 (m, 2H), 2.03–2.06 (m, 2H), 1.60–1.72 (m, 2H), 1.36–1.37 (d, 6H) |
| IR (KBr, cm$^{-1}$) | 3399, 2937, 2248, 1672 |

EXAMPLE-89

3[1-oxo-2-[1-(1-(methylsulphonyl)-piperidin-4-yl)-2-ethyl]hydrazino]ethyl-4-cyanothiazolidine trifluoroacetate (Compound No. 88)

| | |
|---|---|
| Yield | 80% |
| Mass | 376 (M$^+$ + 1), 398 (M$^+$ + Na) |
| $^1$HNMR (d$_4$-MeOH) δ | 5.31–5.34 (t, 1H), 4.74–4.76 (d, 1H), 4.65–4.67 (d, 1H), 4.03–4.25 (m, 2H), 3.80–3.82 (m, 2H), 3.44.3.48 (m, 1H), 3.25–3.29 (q, 2H), 3.38–3.39 (d, 2H), 2.86 (S, 3H), 2.80–2.85 (m, 2H), 2.03–2.05 (m, 2H), 1.64–1.70 (m, 2H), 1.30–1.34 (t, 3H) |
| IR (KBr, cm$^{-1}$) | 3501, 2933, 2246, 1672 |

EXAMPLE-90

3-[1-oxo-2-[1-(1-(morpholinocarbonyl)-piperidin-4-yl)-2-ethyl]hydrazino]ethyl-4-cyanothiazolidine trifluoroacetate (Compound No. 89)

| | |
|---|---|
| Yield | 80% |
| Mass | 411 (M$^+$ + 1), 433 (M$^+$ + Na) |
| $^1$HNMR (d$_4$-MeOH) δ | 5.32–5.33 (t, 1H), 4.73–4.78 (d, 1H), 4.64–4.66 (d, 1H), 4.03–4.11 (m, 2H), 3.77–3.81 (m, 2H), 3.66–3.69 (t, 4H), 3.48–3.51 (m, 1H), 3.38–3.39 (d, 2H), 3.26–3.29 (m, 6H), 2.88–2.90 (m, 2H), 1.92–1.96 (m, 2H), 1.53–1.56 (m, 2H), 1.31–1.36 (t, 3H) |
| IR (KBr, cm$^{-1}$) | 3361, 2929, 2247, 1675 |

EXAMPLE-91

3-[1-oxo-2-[1-(1-(N-ethylmethylaminocarbonyl)-piperidin-4-yl)]hydrazino]ethyl-4-cyanothiazolidine trifluoroacetate (Compound No. 90)

| | |
|---|---|
| Yield | 80% |
| Mass | 355 (M$^+$ + 1), 377 (M$^+$ + Na) |
| $^1$HNMR (d$_4$-MeOH) δ | 5.33–5.35 (t, 1H), 4.71–4.74 (d, 1H), 4.63–4.66 (d, 1H), 4.08–4.12 (m, 2H), 3.71–3.74 (m, 2H), 3.44–3.48 (m, 1H), 3.38–3.39 (d, 2H), 3.22–3.27 (q, 2H), 2.82–2.88 (m, 2H), 2.88 (S, 3H), 1.95–1.97 (m, 2H), 1.53–1.62 (m, 2H), 1.14–1.19 (t, 3H) |
| IR (KBr, cm$^{-1}$) | 3398, 2935, 2245, 1675 |

EXAMPLE-92

3-[1-oxo-2-[1-(1-(4-methoxyphenylsulphonyl)-piperidin-4-yl)]hydrazino]ethyl-4-cyanothiazolidine trifluoroacetate (Compound No. 91)

| | |
|---|---|
| Yield | 80% |
| Mass | 440 (M$^+$ + 1), 462 (M$^+$ + Na) |
| $^1$HNMR (d$_4$-MeOH) δ | 7.72–7.74 (d, 2H), 7.12–7.15 (d, 2H), 5.29–5.31 (t, 1H), 4.67–4.69 (d, 1H), 4.59–4.61 (d, 1H), 4.05–4.07 (m, 2H), 3.90 (S, 3H), 3.72–3.77 (m, 2H), 3.35–3.37 (d, 2H), 3.17–3.19 (m, 1H), 2.38–2.44 (m, 2H), 1.99–2.03 (m, 2H), 1.65–1.71 (m, 2H). |
| IR (KBr, cm$^{-1}$) | 3471, 2954, 2246, 1665 |

EXAMPLE-93

3-[1-oxo-2-[1-(1-(4-methoxyphenylsulphonyl)aminocyclohexan-4-yl)]hydrazino]ethyl-4-cyanothiazolidine trifluoroacetate (Compound No. 92)

| | |
|---|---|
| Yield | 90% |
| Mass | 453 (M$^+$ + 1) |
| $^1$HNMR (d$_4$-MeOH) δ | 7.79–7.82 (d, 2H), 7.07–7.09 (d, 2H), 5.30–5.32 (t, 1H), 4.67–4.69 (d, 1H), 4.59–4.61 (d, 1H), 4.01–4.03 (m, 2H), 3.36–3.37 (d, 2H), 3.08–3.11 (m, 1H), 2.97–3.01 (m, 1H), 1.96–2.03 (m, 2H), 1.85–1.88 (m, 2H), 1.25–1.38 (m, 4H) |
| IR (KBr, cm$^{-1}$) | 2942, 2247, 1673, 1596 |

EXAMPLE-94

3-[1-oxo-2-[1-(1-(4-fluorobenzyl)aminocyclohexan-4-yl)]hydrazino]ethyl-4-cyanothiazolidine bis-trifluoroacetate (Compound No. 93)

| | |
|---|---|
| Yield | 90% |
| Mass | 392 (M$^+$ + 1) |
| $^1$HNMR (d$_4$-MeOH) δ | 7.53–7.56 (t, 2H), 7.20–7.24 (t, 2H), 5.32–5.34 (t, 1H), 4.72–4.74 (d, 1H), 4.63–4.65 (d, 1H), 4.24–4.25 (S, 2H), 4.07–4.14 (m, 2H), 3.64–3.70 (m, 1H), 3.38–3.39 (d, 2H), 3.18–3.22 (m, 1H), 2.32–2.36 (m, 2H), 2.18–2.22 (m, 2H), 1.52–1.58 (m, 4H) |
| IR (KBr, cm$^{-1}$) | 2963, 2248, 1673, 1513 |

EXAMPLE-95

3-[1-oxo-2-[1-(1-(4-fluorobenzyl)-piperidin-4-yl)]hydrazino]ethyl-4-cyanothiazolidine bis-trifluoroacetate (Compound No. 94)

| | |
|---|---|
| Yield | 95% |
| Mass | 387 (M$^+$ + 1), 400 (M$^+$ + Na) |
| $^1$HNMR (d$_4$-MeOH) δ | 7.55–7.58 (t, 2H), 7.23–7.25 (t, 2H), 5.31–5.33 (t, 1H), 4.70–4.72 (d, 1H), 4.59–4.61 (d, 1H), 4.35 (S, 2H), 4.02–4.14 (m, 2H), 3.46.3.59 (m, 3H), 3.37–3.38 (d, 2H), 3.07–3.15 (m, 2H), 2.18–2.24 (m, 2H), 1.83–1.87 (m, 2H). |
| IR (KBr, cm$^{-1}$) | 3364, 2955, 2251, 1675 |

EXAMPLE-96

3-[1-oxo-2-[(1-(1-(2-oxo-2-(5-chloropyridin-2-yl)aminoethyl)piperidin-4-yl)]hydrazino]ethyl-4-cyanothiazolidine tris-trifluoroacetate (Compound No. 95)

| | |
|---|---|
| Yield | 87% |
| Mass | 438 (M$^+$+1), 460 (M$^+$+Na) |
| $^1$HNMR (d$_4$-MeOH) δ | 8.332–8.338 (d, 1H), 8.16–8.18 (d, 1H), 7.83–7.86 (dd, 1H), 5.32–5.34 (t, 1H), 4.72–4.74 (d, 1H), 4.64–4.66 (d, 1H), 4.01–4.14 (m, 4H), 3.66–3.68 (m, 2H), 3.47–3.49 (m, 1H), 3.37–3.38 (d, 2H), 3.21–3.23 (m, 2H), 2.23–2.26 (m, 2H), 2.01–2.05 (m, 2H) |
| IR (KBr, cm$^{-1}$) | 2954, 2249, 1674, 1539 |
| Rotation | −40.28° [C=0.50, MeOH] |

EXAMPLE-97

3-[1-oxo-2-[1-(1-(trimethyl acetamido)cyclohexan-4-yl)]hydrazino]ethyl-4-cyanothiazolidine trifluoroacetate (Compound No. 96)

| | |
|---|---|
| Yield | 90% |
| Mass | 368 (M$^+$ + 1), 390 (M$^+$ + Na) |
| $^1$HNMR (d$_4$-MeOH) δ | 5.53–5.35 (t, 1H), 4.74–4.76 (d, 1H), 4.63–4.65 (d, 1H), 4.04–4.16 (m, 2H), 3.64–3.70 (m, 1H), 3.38–3.41 (d, 2H), 3.18–3.22 (m, 1H), 2.05–2.08 (m, 2H), 1.96–1.99 (m, 2H), 1.36–1.52 (m, 4H), 1.2 (s, 9H) |
| IR (KBr, cm$^{-1}$) | 3342, 2949, 2242, 1693, 1534 |

EXAMPLE-98

3-[1-oxo-2-[1-(1-(methanesulphonyl)aminocyclohexan-4-yl )-2-ethyl]hydrazino]ethyl-4-cyanothiazolidine (Compound No. 97)

| | |
|---|---|
| Yield | 45% |
| Mass | 390 (M$^+$ + 1), 412 (M$^+$ + Na) |
| 1HNMR (d4-MeOH)δ | 5.27–5.28 (t, 1H), 4.71–4.83 (m, 2H), 3.42–3.82 (m, 2H), 3.27–3.34 (m, 3H), 2.80 (S, 3H), 2.76–2.80 (m, 2H), 2.12–2.15 (m, 2H), 1.90–1.93 (m, 2H), 1.25–1.44 (m, 4H), 1.02–1.07 (t, 3H). |
| IR (KBr, cm$^{-1}$) | 3587, 3218, 2243, 1739, 1677 |

EXAMPLE-99

3-[1-oxo-$^2$-[(1-(trimethyl acetamido)cyclohexan-4-yl)]hydrazino]ethyl-4-cyanothiazolidine trifluoroacetate (Compound No. 98)

| | |
|---|---|
| Yield | 60% |
| Mass | 367 (M$^+$ + 1) |
| $^1$HNMR (d$_4$-MeOH) δ | 5.33–5.35 (t, 1H), 4.72–4.74 (d, 1H), 4.68–4.70 (d, 1H), 4.02–4.15 (m, 2H), 3.76–3.80 (m, 1H), 3.38–3.48 (m, 1H), 3.32–3.33 (d, 2H), 1.75–1.78 (m, 8H), 1.2 (S, 9H). |
| IR (KBr, cm$^{-1}$) | 3408, 2933, 2159, 1672 |

EXAMPLE-100

3-[1-oxo-2-[1-(1-(2-oxo-2-(4-cyanophenyl)aminoethyl)piperidin-4-yl)]hydrazino]ethyl-4-cyanothiazolidine bis-trifluoroacetate (Compound No. 99)

| | |
|---|---|
| Yield | 90% |
| Mass | 428 (M$^+$ + 1), 450 (M$^+$+ Na) |
| $^1$HNMR (d$_4$-MeOH) δ | 7.80–7.83 (d, 2H), 7.73–7.75 (d, 2H), 5.53–5.35 (t, 1H), 4.72–4.74 (d, 1H), 4.63–4.65 (d, 1H), 4.20 (S, 2H), 4.10–4.18 (m, 2H), 3.48–3.75 (m, 3H), 3.38–3.39 (d, 2H), 3.25–3.27 (m, 2H), 2.26–2.29 (m, 2H), 2.03–2.05 (m, 2H). |
| IR (KBr, cm$^{-1}$) | 3411, 2934, 2248, 1675, 1647 |

EXAMPLE-101

3-[1-oxo-2-[1-(4-fluorobenzoyl)aminocyclohexan-4-yl)]hydrazino]ethyl-4-cyanothiazolidine trifluoroacetate (Compound No. 100)

| | |
|---|---|
| Yield | 75% |
| Mass | 428 (M$^+$+ Na) |
| $^1$HNMR (d$_4$-MeOH) δ | 7.86–7.89 (t, 2H), 7.18–7.22 (t, 2H), 5.32–5.34 (t, 1H), 4.72–4.74 (d, 1H), 4.60–4.62 (d, 1H), 4.09–4.20 (m, 2H), 3.46–3.50 (m, 2H), 3.39–3.40 (d, 2H), 1.77–1.89 (m, 8H). |
| IR (KBr, cm$^{-1}$) | 3273, 2949, 2248, 1675, 1644 |

EXAMPLE-102

3-[1-oxo-2-[1-(1-(2-oxo-2-(5-chloropyridin-2-yl)aminoethyl)piperidin-4-yl)]-2-ethylhydrazino]ethyl-4-cyanothiazolidine tris-hydrochloride (Compound No. 101)

| | |
|---|---|
| Yield | 87% |
| Mass | 466(M$^+$ + 1), 488 (M$^+$+ Na) |
| $^1$HNMR (d$_4$-MeOH) δ | 8.332–8.338 (d, 1H), 8.16–8.18 (d, 1H), 7.83–7.86 (dd, 1H), 5.35–5.37 (t, 1H), 4.64–4.82 (m, 4H), 4.05–4.24 (m, 4H), 3.78–3.82 (m, 2H), 3.47–3.49(m, 1H), 3.32–3.40 (m, 4H), 2.22–2.30 (m, 3H), 2.01–2.05 (m, 3H), 1.35–1.39(t, 3H). |
| IR (KBr, cm$^{-1}$) | 2946, 2247, 1696, 1667 |
| Rotation | –40.84° [C = 0.50, MeOH] |

EXAMPLE-103

3-[1-oxo-2-[-1-(1-(2-oxo-2(4-trifluorophenyl)aminoethyl)piperidin-4-yl)]hydrazino]ethyl-4-cyanothiazolidine bis-trifluoroacetate (Compound No. 102)

| | |
|---|---|
| Yield | 59% |
| Mass | 471 (M$^+$ + 1) |
| $^1$HNMR (d4-MeOH) δ | 7.81–7.83 (d, 2H), 7.66–7.68 (d, 2H), 5.32–5.34 (t, 1H), 4.73–4.75 (d, 1H), 4.65–.467 (d, 1H), 4.1 (S, 2H), 4.03–4.06 (m, 2H), 3.53–3.69 (m, 2H), 3.46–3.50 (m, 1H), 3.38–3.39 (d, 2H), 3.46–3.50 (m, 1H), 2.23–2.26 (m, 2H), 2.01–2.05 (m, 2H) |
| IR (KBr, cm$^{-1}$) | 2945, 2249, 1674, 1613 |

EXAMPLE-104

3-[1-oxo-2-[1-(1-(2-oxo-2(-adamant-1-yl)amino ethyl)piperidin-4-yl)]hydrazino]ethyl-4-cyanothiazolidine bis-trifluoroacetate (Compound No. 103)

| | |
|---|---|
| Yield | 53% |
| Mass | 461 (M$^+$+ 1) |
| $^1$HNMR (d4-MeOH) δ | 5.32–5.34 (t, 1H), 4.71–4.73 (d, 2H), 4.63–4.65 (d, 1H), 4.05–4.08 (m, 2H), 3.8 (S, 2H), 3.48–3.50 (m, 3H), 3.37–3.39 (d, 2H), 3.32–3.33 (m, 2H), 2.03–2.09 (m, 2H), 1.85–2.02 (m, 11H), 1.72-1.75 (m, 6H) |
| IR (KBr, cm$^{-1}$) | 2910, 1674, 1558 |

EXAMPLE-105

3-[1-oxo-2-[1-(1-(2-oxo-2(2,3-dihydrobenzo(14)dioxan-6-yl)aminoethyl)piperidin-4-yl)]hydrazino]ethyl-4-cyano-thiazolidine bis-trifluoroacetate (Compound No. 104)

| | |
|---|---|
| Yield | 80% |
| Mass | 461 (M$^+$ + 1):, 483 (M$^+$ + Na): |
| $^1$HNMR (d4-MeOH) δ | 7.22–7.23 (d, 1H), 6.94–6.97 (dd, 1H), 6.79–6.82 (d, 2H), 5.32–5.34 (t, 1H), 4.73–4.75 (d, 1H), 4.64–4.67 (d, 1H), 4.24 (S, 1H), 4.00–4.05 (m, 4H), 3.50–3.51 (m, 2H), 3.46–3.47 (m, 1H), 3.38–3.39 (d, 2H), 3.15–3.32 (m, 2H), 2.21–2.23 (m, 2H), 2.03–2.05 (m, 2H) |
| IR (KBr, cm$^{-1}$) | 2949, 1677, 1620 |

EXAMPLE-106

3-[1-oxo-2-[1-(1-(2-oxo-2(4-chlorophenyl)aminoethyl)piperidin-4-yl)]hydrazino]ethyl-4-cyanothiazolidine bis-trifluoroacetate (Compound No. 105)

| | |
|---|---|
| Yield | 60% |
| Mass | 437 (M$^+$ + 1), 459 (M$^+$ + Na) |
| $^1$HNMR (d4-MeOH) | 7.60–7.62 (d, 2H), 7.35–7.37 (d, 2H), 5.32–5.33 (t, 1H), 4.73–4.76 (d, 1H), 4.65–4.67 (d, 1H), 4.07- (S, 1H), 3.92–4.00 (m, 2H), 3.59–3.64 (m, 2H), 3.51–3.52 (m, 1H), 3.17–3.38 (d, 2H), 3.15–3.32 (m, 2H), 2.18–2.21 (m, 2H), 1.99–2.05 (m, 2H) |
| IR (KBr, cm$^{-1}$) | 2924, 1677, 1620 |

EXAMPLE-107

3[2-oxo-2-[1-(1-(2-oxo-2(pyrimidin-2-yl)aminoethyl)piperidin-4-yl)]hydrazino]ethyl-4-cyanothiazolidine tris-trifluoroacetate (Compound No. 106)

| | |
|---|---|
| Yield | 66% |
| Mass | 408 (M$^+$ + 1), 427 (M$^+$ + Na) |
| $^1$HNMR (d4-MeOH) δ | 8.66–8.67 (d, 2H), 7.20–7.23 (t, 1H), 5.32–5.34 (t, 1H), 4.68–4.72 (m, 1H), 4.63–4.67 (d, 1H), 4.60–4.62 (m, 2H), 4.09–4.19 (m, 2H), 3.72–3.74 (m, 2H), 3.47–3.53 (m, 3H), 3.38–3.39 (d, 2H), 2.25–2.28 (m, 2H), 2.03–2.05 (m, 2H) |
| IR (KBr, cm$^{-1}$) | 2978, 1678, 1517 |

EXAMPLE-108

3-[1-oxo-2-[1-(1-(-2-oxo-2(morpholin-4-yl)ethyl)piperidin-4-yl)]hydrazino]ethyl-cyanothiazolidine bis-trifluoroacetate (Compound No. 107)

| | |
|---|---|
| Yield | 86% |
| Mass | 397 (M$^+$ + 1), 419 (M$^+$ + Na) |
| $^1$HNMR (d4-MeOH) δ | 5.32–5.34 (t, 1H); 4.72–4.74 (d, 1H), 4.63–4.65 (d, 1H), 4.28 (S, 2H), 4.02–4.14 (m, 2H), 3.70–3.71 (t, 4H), 3.61–3.63 (m, 2H), 3.47–3.51 (m, 1H), 3.42–3.43 (m, 2H), 3.38–3.39 (d, 2H), 3.32 (t, 4H), 2.21–2.24 (m, 2H), 1.99–2.03 (m, 2H) |
| IR (KBr, cm$^{-1}$) | 2977, 1676, 1539 |

EXAMPLE-109

3[1-oxo-2-[1-(1-(2-oxo-2-(cyclopropyl)aminoethyl) piperidin-4-yl)]hydrazino]ethyl-4-cyanothiazolidine bis-trifluoroacetate (Compound No. 108)

| Yield | 40% |
|---|---|
| Mass | 367 ($M^+ + 1$), 389 ($M^+ + Na$) |
| $^1$HNMR (d4-MeOH) δ | 5.31–5.33 (t, 1H), 4.72–4.75 (d, 1H), 4.63–4.66 (d, 1H), 4.01–4.09 (m, 2H), 3.87 (S, 2H), 3.51–3.53 (m, 2H), 3.48–3.50 (m, 1H), 3.37–3.38 (d, 2H), 3.14–3.16 (m, 2H), 2.73–2.77 (m, 1H), 2.20–2.23 (m, 2H), 2.01–2.03 (m, 2H), 0.76–0.79 (m, 2H), 0.52–0.56 (m, 2H) |
| IR (KBr, cm$^{-1}$) | 2994, 1677, 1541 |

EXAMPLE-110

3-[1-oxo-2-[1-(1-(2-cyanobiphenyl-4-yl)methyl) piperidine-4-yl]hydrazino]ethyl-4-cyanothiazolidine bis-trifluoroacetate (Compound No. 109)

| Yield | 80% |
|---|---|
| Mass | 461 ($M^+ + 1$), 483 ($M^+ + Na$) |
| $^1$HNMR (d4-MeOH) δ | 7.59–7.90 (m, 8H), 5.31–5.33 (d, 1H), 4.71–4.73 (d, 2H), 4.61–4.64 (d, 1H), 4.45 (S, 2H), 4.01–4.12 (2H), 3.59–3.66 (m, 2H), 3.50–3.53 (m, 1H), 3.37–3.38 (d, 2H), 3.15–3.32 (m, 2H), 2.25–2.27 (m, 2H), 2.03–2.05 (m, 2H) |
| IR (KBr, cm$^{-1}$) | 2944, 2247, 1676 |

EXAMPLE-111

3-[1-oxo-2-[1-(1-(1-oxo-2-(morpholin-4-yl)ethyl) piperidin-4-yl)]hydrazino]ethyl-4-cyanothiazolidine bis-trifluoroacetate (Compound No. 110)

| Yield | 51% |
|---|---|
| Mass | 397 ($M^+ + 1$), 419 ($M^+ + Na$) |
| $^1$HNMR (d4-MeOH) δ | 5.32–5.33 (t, 1H), 4.72–4.74 (d, 1H), 4.64–4.66 (d, 1H), 4.51–4.54 (m, 1H), 4.24–4.34 (m, 2H), 4.03–4.05 (m, 2H), 3.96 (t, 4H), 3.78–3.82 (m, 1H), 3.48–3.51 (m, 1H), 3.38–3.39 (d, 2H), 3.32–3.34 (t, 4H), 3.07–3.19 (m, 1H), 2.84–2.90 (m, 1H), 2.03–2.05 (m, 2H), 1.51–1.64 (m, 2H) |
| IR (KBr, cm$^{-1}$) | 2949, 2247, 1673 |

EXAMPLE-112

3-[1-oxo-2-[1-(4-(2-oxo-2-(5-chloropyridin-2-yl) aminoethyl)amino cyclohex-1-yl)]hydrazino]ethyl-4-cyanothiazolidine tris-trifluoroacetate (Compound No. 111)

| Yield | 66% |
|---|---|
| Mass | 452 ($M^+ + 1$), 474 ($M^+ + Na$) |
| $^1$HNMR (d4-MeOH) δ | 8.32–8.33 (d, 1H), 8.14–8.16 (d, 1H), 7.83–7.85 (dd, 1H), 5.32–5.33 (t, 1H), |

-continued

| | 4.72–4.74 (d, 1H), 4.59–4.63 (d, 1H), 3.98–4.08 (m, 4H), 3.38–3.39 (t, 2H), 3.21–3.23 (m, 2H), 2.28–2.30 (m, 2H), 2.19–2.20 (m, 2H), 1.53–1.62 (m, 4H) |
|---|---|
| IR (KBr, cm$^{-1}$) | 2977, 1676, 1539 |

EXAMPLE-113

3-[1-oxo-2-[1-(4-(2-oxo-2-(4-cyanophenyl)aminoethyl)aminocyclohex-1-yl)]hydrazino]ethyl-4-cyanothiazolidine bis-trifluoroacetate (Compound No. 112)

| Yield | 75% |
|---|---|
| Mass | 442 ($M^+ + 1$) |
| $^1$HNMR (d4-MeOH) δ | 7.80–7.82 (d, 1H), 7.72–7.74 (d, 1H), 5.32–5.33 (d, 1H), 4.71–4.73 (d, 1H), 4.53–4.65 (d, 1H), 4.02–4.13 (m, 4H), 3.38–3.39 (d, 2H), 3.07–3.15 (m, 2H), 2.29–2.31 (m, 2H), 2.18–2.20 (m, 2H), 1.56–1.63 (m, 4H). |
| IR (KBr, cm$^{-1}$) | 2946, 2226, 1676 |

EXAMPLE-114

3-[1-oxo-2-[1-(4-(2-oxo-2-(4-chlorophenyl)aminoethyl)aminocyclohex-1-yl)]hydrazino]ethyl-4-cyanothiazolidine bis-trifluoroacetate (Compound No. 113)

| Yield | 85% |
|---|---|
| $^1$HNMR (d4-MeOH) δ | 7.60–.762 (d, 2H), 7.34–7.36 (d, 2H), 5.32–5.33 (t, 1H), 4.72–4.74 (d, 1H), 4.65–4.67 (d, 1H), 3.98–4.09 (m, 4H), 3.37–3.38 (d, 2H), 3.07–3.15 (m, 2H), 2.29–2.31 (m, 2H), 2.17–2.19 (m, 2H), 1.53–1.59 (m, 4H) |
| Mass | 451 ($M^+ + 1$) |
| IR (KBr, cm$^{-1}$) | 2948, 1677, 1544 |

EXAMPLE-115

3-[1-oxo-2-(1-(1-methanesulphonylamino-4-cyclohexyl)hydrazino)]ethyl-4-cyanothiazolidine hydrochloride (Compound No. 114)

| Yield | 70% |
|---|---|
| Mass | 362 ($M^+ + 1$), 384 ($M^+ + Na$) |
| $^1$HNMR (d4-MeOH) δ | 5.33–5.35 (t, 1H), 4.73–4.76 (d, 1H), 4.64–4.66 (d, 1H), 4.06–4.14 (m, 2H), 3.38–3.40 (d, 2H), 3.15–3.25 (m, 2H), 2.97 (S, 3H), 2.14–2.16 (m, 2H), 2.01–2.03 (m, 2H), 1.36–1.50 (m, 4H). |
| IR (KBr, cm$^{-1}$) | 2936, 1664 and 1444 |

EXAMPLE-116

3-[-1-oxo-2-[1-(1-(-2-oxo-2-(5-chloropyridin-2-yl)aminoethyl)piperidine-4-yl)]hydrazino]ethyl-4-cyanothiazolidine trihydrochloride (Compound No. 115)

| | |
|---|---|
| Yield | 70% |
| Mass | 438 ($M^+$ + 1), 460 ($M^+$ + Na) |
| $^1$HNMR (d4-MeOH) δ | 8.32–8.33 (d, 1H), 8.18 (S, 1H), 7.84–7.86 (d, 1H), 5.34–5.35 (t, 1H), 4.73–4.75 (d, 1H), 4.66–4.68 (d, 1H), 4.11–4.28 (m, 4H), 381–3.83 (m, 2H), 3.67–3.69 (m, 1H), 3.48–3.49 (m, 2H), 3.38–3.39 (d, 1H), 2.27–2.29 (m, 2H), 2.03–2.11 (m, 2H) |
| IR (KBr, cm$^{-1}$) | 2940, 2246 and 1695 |

Examples of Scheme 2:

EXAMPLE-117

[2-Cyano-1-(piperazine-2-yl)-carbonyl pyrrolidine bis-trifluoroacetate] (Compound No. 1).

| | |
|---|---|
| Yield | 97.32%; |
| m.p. | 126–128° C.; |
| Mass (m/z) | 209 ($M^+$ + 1), 231 ($M^+$ + Na); |
| $^1$HNMR (400 MHz, d$_4$-MeOH) δ | 4.79–4.82 (m, 1H), 4.27–4.30 (dd, 1H, J=4Hz, 4Hz), 3.91–3.94 (m, 1H), 3.59–3.62 (m, 1H), 3.22–3.39 (m, 6H), 2.19–2.31 (m, 4H); |
| IR (KBr, cm$^{-1}$) | 3000, 2364, 1673, 1430. |

EXAMPLE-118

[2-Cyano-1-(4-isopropyl-2-piperazinyl)-carbonyl-pyrrolidine bis trifluoroacetate] (Compound No. 2)

| | |
|---|---|
| Yield | 53.92%; |
| Mass (m/z) | 251 ($M^+$ + 1); |
| $^1$HNMR (400 MHz, d$_4$-MeOH) δ | 4.79–4.82 (m, 1H), 4.28–4.30 (m, 1H), 3.56–3.74 (m, 2H), 2.41–3.47 (m, 7H), 2.21–2.37 (m, 4H), 1.31–1.33 (d, 6H, J=8Hz); |
| IR (CCl$_4$, cm$^{-1}$) | 3480, 2962, 2302, 1677, 1453. |

Examples of Scheme 3:

EXAMPLE-119

[4-Cyano-3-(1-isopropylhydrazino)carbonyl thiazolidine hydrochloride] (Compound No. 31)

| | |
|---|---|
| Yield | 52.63%; |
| m.p. | 148–150° C. (dec.); |
| Mass (m/z) | 215 ($M^+$ + 1), 199; |
| $^1$HNMR (400 MHz, d$_4$-MeOH) δ | 5.13–5.15 (d, 1H, J = 8Hz), 4.59–4.62 (m, 1H,), 4.24–4.28 (m, 2H), |

-continued

| | |
|---|---|
| | 3.42–3.46 (dd, 1H, J = 6Hz, 4Hz), 2.96–3.00 (t, 1H, J = 8Hz), 1.22–1.26 (t, 6H, J=8Hz); |
| IR (KBr, cm.$^{-1}$) | 3646, 2940, 2355, 1649. |

EXAMPLE 120

[2-Cyano-1-(1-cyclohexyl hydrazino)carbonyl pyrrolidine hydrochloride] (Compound No. 32)

| | |
|---|---|
| Yield | 22.62%; |
| m.p. | 160–162° C. (dec.); |
| Mass (m/z) | 237($M^+$ + 1), 155; |
| $^1$HNMR (400 MHz, CDCl$_3$)δ | 8.75–8.77 (bs, 2H), 4.14–4.25 (bs, 2H,), 3.53–3.65 (bs, 1H), 3.50–3.52 (bs, 1H), 2.60–2.80 (bs, 1H), 2.06–2.27 (m, 3H), 1.79–1.90 (m, 6H), 1.65–1.68 (m, 1H), 1.23–1.29 (m, 3H); |
| IR (KBr, cm.$^{-1}$) | 3646, 3245, 2931, 2360, 1666. |

EXAMPLE-121

[4-Cyano-3-(1-cyclohexylhydrazino)carbonyl thiazolidine hydrochloride] (Compound No. 33)

| | |
|---|---|
| Yield | 32.46%; |
| m.p. | 166–168° C. (dec.); |
| Mass (m/z) | 255 ($M^+$ + 1), 173; |
| $^1$HNMR (400 MHz, d$_4$-MeOH)δ | 4.863–4.88(d, 1H, J=8Hz), 4.18–4.20 (d, 2H, J=8Hz), 3.29–3.32(m, 1H), 3.16–3.20 (t, 1H, J=8Hz), 2.92–2.96 (t, 1H, J=8Hz), 1.66–1.73 (m, 2H), 1.54–1.64 (m, 4H), 1.49–1.53 (m, 1H), 1.18–1.23 (m, 2H), 1.04–1.10 (m, 1H); |
| IR (KBr, cm.$^{-1}$) | 3748, 3226, 2934, 2345, 1656. |

Pharmaceutical Compositions

Pharmaceutical compositions may be prepared with a pharmaceutically effective quantity of compounds of general formula I, individually or in combination. It is common practice to administer the compounds in the form of pharmaceutical dosage forms comprising pharmaceutically acceptable excipient(s) and at least one active ingredient. These dosage forms may be administered by a variety of routes including oral, topical, transdermal, subcutaneous, intramuscular, intravenous, intranasal, pulmonary etc. Administration of the agents according to the instant invention may take place over an extended period of time at a dosage level of, for example, up to about 30 mg/kg. The pharmaceutical composition can be in the range of 0.5% to 90% by weight of the compound.

The following pharmaceutical formulations suggested are by way of example alone and in no way restrict the forms in which they can be used.

Oral Formulations

Oral formulations may be administered as solid dosage forms for example pellets, powders, sachets or discreet units such as tablets or capsules and like. Other orally administered pharmaceutical preparations include monophasic and biphasic liquid dosage forms either in ready to use form or forms suitable for reconstitution such as mixtures, syrups, suspensions or emulsions. The preparations in addition may contain diluents, dispersing agents, buffers, stabilizers, solubilizers, surfactants, preservatives, chelating agents and/or other pharmaceutical additives as are used. Aqueous or non-aqueous vehicle or their combination may be used and if desired may contain suitable sweetener, flavoring agent or similar substances. In case of suspension or emulsion a suitable thickening agent or suspending agent or emulsifying agent may be present in addition. Alternatively, the compounds may be administered as such in their pure form unassociated with other additives for example as capsules or sachets. It may also be administered with a vehicle. Pharmaceutical preparations can have a slow, delayed or controlled release of active ingredients as is provided by a matrix or diffusion controlled system.

When the present invention or its salts or suitable complexes is presented as a discrete unit dosage form like tablet, it may contain in addition medically inert excipients as are used in the art. Some example of suitable excipients include lactose, cellulose and its derivatives such as microcrystalline cellulose, methylcelulose, hydroxy propyl methyl cellulose, ethylcellulose, dicalcium phosphate, mannitol, starch, gelatin, polyvinyl pyrolidone, various gums like acacia, tragacanth, xanthan, alginates & its derivatives, sorbitol, dextrose, xylitol, magnesium stearate, talc, colloidal silicon dioxide, mineral oil, glyceryl mono stearate, glyceryl behenate, sodium starch glycolate, Cross Povidone, crosslinked carboxymethylcellulose, various emulsifiers such as polyethylene glycol, sorbitol, fatty acid esters, polyethylene glycol alkylethers, sugar esters, polyoxyethylene polyoxypropyl block copolymers, polyethoxylated fatty acid monoesters, diesters and mixtures thereof.

Preparation of Oral Dosage Form:

A typical tablet can have the following compositions:

Oral formulation

A tablet formulation may be prepared as per the following compositions.

EXAMPLE-122

| Ingredients | Qty. (mg/tablet) |
| --- | --- |
| Active ingredient of formula I | 20.0 mg |
| Microcrystalline Cellulose | 200.0 mg |
| Starch | 50.0 mg |
| Magnesium Stearate | 5.0 mg |
| Talc | 2.0 mg |

EXAMPLE-123

| Ingredients | Qty. (mg/tablet) |
| --- | --- |
| Active ingredient of formula I | 10 mg |
| Lactose | 75 mg |
| Starch | 50 mg. |
| Polyvinyl pyrolidone (10% solution in water) | 5 mg |
| Sodium starch glycolate | 5 mg |
| Magnesium Stearate | 2 mg |
| Colloidal Silicon-dioxide | 5 mg |

EXAMPLE 124

| Ingredients | Qty. (mg/tablet) |
| --- | --- |
| Active ingredient | 5.0 mg |
| Microcrystalline Cellulose | 80.5 mg |
| Starch | 8.0 mg. |
| Talc | 3.3 mg |
| Magnesium Stearate | 1.6 mg |
| Colloidal Silicon-dioxide | 1.6 mg |

Active ingredient, lactose and starch are screened through 40 # sieve and blended. The blend is then granulated with polyvinyl pyrolidone solution. Resultant mass is screened through number 16 sieve. The granules produced are then dried at 50–60° C. and passed through 16-mesh sieve. Sodium starch glycolate, magnesium Stearate and colloidal silicon dioxide are sifted through 60-mesh sieve and blended with the granules. The resultant blend is then compressed into tablets.

The above ingredients may be blended into tablets by any other conventional materials.

Parenteral Formulations

For parenteral administration, the compounds or their salts or suitable complexes thereof may be present in a sterile vehicle which may be an aqueous or non-aqueous vehicle or a combination thereof. The examples of vehicles are water, ethyl oleate, oils and derivatives of polyols, glycols and their derivatives. It may contain additives common in injectable preparations like stabilizers, solubilizers, pH modifiers, buffers, antioxidants, cosolvents, complexing agents, tonicity modifiers, etc.

Some suitable additives are for example tartrate, citrate or similar buffers, alcohol, sodium chloride, dextrose and high molecular weight polymers. Another alternative is sterile powder reconstitution. The compound may be administered in the form of injection for more than once daily administration, or intravenous infusion/drip or suitable depot preparation.

For injectable administration, the active ingredient or its salt is dissolved or dispersed in a sterile vehicle. The vehicle may be aqueous or non-aqueous and may contain suitable surfactants, solubilizers, buffers, stabilizers, surfactants, antioxidants, cosolvents, chelating agents, tonicity modifiers etc. Various excipients commonly used include propylene glycol; polythene glycol mannitol, sodium chloride, ethyloleate, polyethylene glycol fatty acid esters, polyethylene glycol castor oil, polyethylene glycol sarbitan fatty acid esters, sugar esters, various buffers such as phosphate, succinate, citrate, borate, antioxidants such as sodium metabisulphite etc.

An injectable formulation containing the following ingredient may be prepared:

EXAMPLE 125

| Ingredients | Qty. |
| --- | --- |
| Active ingredient of formula I | 1 mg |
| Polythylene glycol | 0.1 ml |
| Isotonic Saline/WFI | to 1 ml |
| Sodium metabisulphite | |

OTHER FORMULATIONS

For the dermatological application and for the buccal delivery, the recommended formulations are gel, ointment, creams, patches, liniment, lotions, oral rinse, gurgles and toothpaste containing appropriate compounds of the general formula I.

The above examples are presented by way of illustration alone and in no way limit the scope of the invention.

What is claimed is:

1. A compound represented by general formula (I), or a stereoisomer thereof

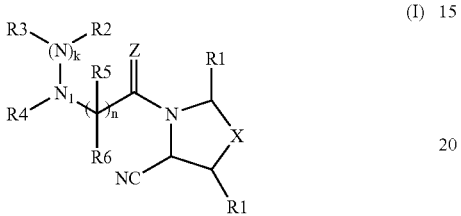

wherein

X is O, S, SO, $SO_2$, NR7 or CHR1;

n is 1;

k is 1;

Z is O, S, and NR7;

R1 at two positions are independently selected from hydrogen or a substituted or unsubstituted group selected from linear or branched $(C_1–C_{12})$alkyl, $(C_2–C_{12})$alkenyl, $(C_3–C_7)$cycloalkyl, $(C_5–C_7)$cycloalkenyl, bicycloalkyl, bicycloalkenyl, heterocycloalkyl, aryl, aryloxy, aralkyl, aralkoxy, heteroaryl, heteroaralkyl, heteroaryloxy, heteroaralkoxy, wherein one or more heteroatoms are independently selected from O, N or S;

R2, R3, R4 and R7 are independently selected from hydrogen, perhaloalkyl, (CO)NR8R9, —(CO)R8, —(CO)OR8, —$SO_2$R8, —SOR8, substituted or unsubstituted groups selected from linear or branched $(C_1–C_{12})$alkyl, $(C_2–C_{12})$alkenyl, $(C_3–C_7)$cycloalkyl, $(C_5–C_7)$cycloalkenyl, bicycloalkyl, amidino bicycloalkenyl, heterocycloalkyl, aryl, aralkyl, heteroaryl, heteroaralkyl, wherein one or more heteroatoms are independently selected from O, N or S;

R5 and R6 are independently selected from by hydrogen or a substituted or unsubstituted group selected from linear or branched $(C_1–C_{12})$alkyl, $(C_2–C_{12})$alkenyl, $(C_3–C_7)$cycloalkyl, $(C_5–C_7)$cycloalkenyl, bicycloalkyl, bicycloalkenyl, heterocycloalkyl, aryl, aralkyl, heteroaryl, heteroaralkyl, wherein one or more heteroatoms are independently selected from O, N or S;

R8 and R9 are independently selected from hydrogen or a substituted and unsubstituted group selected from linear or branched $(C_1–C_{12})$alkyl, alkoxyaryl, alkoxyalkyl, alkoxycycloalkyl, alkoxyaryl, perhaloalkyl, $(C_2–C_{12})$alkenyl, $(C_3–C_7)$cycloalkenyl, perhalocycloalkyl, haloheterocycloalkyl, cyanoheterocycloalkyl, perhaloheterocycloalkyl, $(C_5–C_7)$cycloalkenyl, bicycloalkyl, bicycloalkenyl, heterocycloalkyl, aryl, aralkyl, heteroaryl, heteroaralkyl, perhaloaryl, perhaloheteroaryl;

wherein in the groups represented by R1, R2, R3, R4, R5, R6, R7, R8 and R9 when substituted, the substitutents are optionally and independently bridged by —(CO)—, —(CO)O, —(CO)NH—, —NH—, —NR8-, —O—, —S—, —(SO)—, —($SO_2$)—, —($SO_2$)NH—, —NH($SO_2$)—, —O(CO)— or —NH(CO)—; and are selected from halogen, hydroxy, nitro, cyano, amino, oxo, oxime, unsubstituted or substituted by R10 for the groups selected from linear or branched $(C_1–C_8)$alkyl, $(C_3–C_7)$cycloalkyl, alkylcycloalkyl, perhaloalkyl, perhalocycloalkyl, aryl, aralkyl, alkylaryl, alkylheteroaryl, aralkoxylalkyl, perhaloaryl, alkylheterocycloalkyl, heterocycloalkyl, perhaloheterocyclyloalkyl, heteroaryl, heteroaralkyl, alkylaryl, perhaloheteroaryl, acyl, acyloxy, acylamino, alkylamino, arylamino, aralkoxy, alkoxyalkyl, alkylthio, thioalkyl, arylthio, thioaryl, carboxylic acid or its derivatives, or sulfonic acid or its derivatives wherein the groups/substituents present on same or adjacent atoms such as carbon or nitrogen, together optionally and independently may form a five or a six or a seven membered ring optionally containing one or more double bonds and optionally containing one or more heteroatoms selected from O, N or S;

and wherein

R10 is independently selected from halogen, hydroxy, nitro, cyano, amino, oxo or oxime; or a pharmaceutically acceptable hydrate or salt thereof.

2. The compound or pharmaceutically acceptable hydrate or salt as claimed in claim 1, wherein said compound is selected from the group consisting of:

c) 1-[1-Oxo-2-((1-phenyl)-hydrazino)]ethyl-2-cyano pyrrolidine trifluoroacetate, d) 1-[1-Oxo-2-(1-hydrazino)]ethyl-2-cyano pyrrolidine trifluoroacetate, e) 3-[1-Oxo-2-((2-(1,1-dimethyl ethyl oxy carbonyl))hydrazino)]ethyl-4-cyano thiazolidine, f) 1-[1-Oxo-2-((2-(1,1-dimethylethyloxy carbonyl))-1-phenyl hydrazino)]ethyl-2-cyano pyrrolidine, g) 1-[1-Oxo-2-((2-(1,1-dimethylethyl oxy carbonyl))hydrazino)]ethyl-2-cyano pyrrolidine, h) 1-[1-Oxo-2-((1-(4-nitrophenylmethyl))hydrazino)] ethyl-2-cyano pyrrolidine trifluoroacetate, i) 3-[1-Oxo-2-((1-phenyl)hydrazino)]ethyl-4-cyano thiazolidine trifluoroacetate, j) 1-[1-Oxo-2-(1-(2-methylpropyl)hydrazino)]ethyl-2-cyano pyrrolidine trifluoroacetate, k) 1-[1-Oxo-2-((1-phenylmethyl)hydrazino)]ethyl-2-cyano pyrrolidine trifluoroacetate, l) 1-[1-Oxo-2-((1-(1-methyl)ethyl)hydrazino)]ethyl-2-cyano pyrrolidine trifluoroacetate, m) 1-[1-Oxo-2-((2,2-diethyl)-hydrazino)]ethyl-2-cyano thiazolidine, n) 1-[1-Oxo-2-((1-ethyl)hydrazino)]ethyl-2-cyano pyrrolidine trifluoroacetate, o) 3-[1-Oxo-2-(1-hydrazino)]ethyl-4-cyano thiazolidine trifluoroacetate, p) 3-[1-Oxo-2-((1-phenylmethyl)hydrazino)]ethyl-4-cyano thiazolidine trifluoroacetate, q) 3-[1-Oxo-2-((1-(4-nitrophenylmethyl))hydrazino)] ethyl-4-cyano thiazolidine trifluoroacetate, r) 1-[1-Oxo-2-((1-Cyclopentyl)-hydrazino)]ethyl-2-cyano pyrrolidine trifluoroacetate, s) 3-[1-Oxo-2-((1-Cyclopentyl)-hydrazino)]ethyl-4-cyano thiazolidine trifluoroacetate, t) 1-[1-Oxo-2-((1-Cyclohexyl)-hydrazino)]ethyl-2-cyano pyrrolidine trifluoroacetate, u) 3-[1-Oxo-2-((1-Cyclohexyl)-hydrazino)]ethyl-4-cyano thiazolidine trifluoroacetate, v) 1-[1-Oxo-2-((1-methylpropyl)hydrazino)]ethyl-2-cyano pyrrolidine trifluoroacetate, w) 3-[1-Oxo-2-((1-methylpropyl)hydrazino)]ethyl-4-cyano thiazolidine trifluoroacetate,
x) 1-[1-Oxo-2-((1-Phenyl sulphonyl)hydrazino)]ethyl-2-cyano pyrrolidine trifluoroacetate,
y) 3-[1-Oxo-2-((1-(4-methyl)cyclohexyl)hydrazino)]ethyl-4-cyano thiazolidine trifluoroacetate,
z) 1-[1-Oxo-2-((4-Methyl)cyclohexyl)hydrazino)]ethyl-2-cyano pyrrolidine trifluoroacetate,
aa) 1-[1-Oxo-2-(1-(2-Pyridyl)-hydrazino)]ethyl-2-cyano pyrrolidine bis-trifluoroacetate,
bb) 3-[1-Oxo-2-((1-Cycloheptyl)-hydrazino)]ethyl-4-cyano thiazolidine trifluoroacetate,
cc) 3-[1-Oxo-2-((1-(4-methyl)cyclohexyl)-hydrazino)]ethyl-4-cyano thiazolidine trifluoroacetate,
dd) 1-[1-Oxo-2-((1-Cycloheptyl)hydrazino)]ethyl-2-cyano pyrrolidine trifluoroacetate,
ee) [4-Cyano-3-(1-isopropylhydrazino)carbonyl thiazolidine hydrochloride],
ff) [2-Cyano-1-(1-cyclohexyl hydrazino)carbonyl pyrrolidine hydrochloride],
gg) [4-Cyano-3-(1-cyclohexylhydrazino)carbonyl thiazolidine hydrochloride],
hh) 1-[1-Oxo-2-(2-cyclohexyl)hydrazino]ethyl-2-cyanopyrrolidine trifluoroacetate,
ii) [4-Cyano-3-(1-phenyl hycirazino)carbonyl thiazolidine trifluoroacetate],
jj) 3-[1-Oxo-2-(1-cyclohexyl-2-isopropyl)hydrazino]ethyl-4-cyanothiazolidine hydrochloride,
kk) 1-[1-Oxo-2-(4-methylcyclohexyl)hydrazino]ethyl-2-cyanopyrrolidine trifluoroacetate,
ll) 1-[1-Oxo-2-(1-cyclohexyl-2-isopropyl)hydrazino]ethyl-2-cyano pyrrolidine,
mm) 1-[1-Oxo-2-(1-(4-methylcyclohexylmethyl)hydrazino)]ethyl-2-cyanopyrrolidine trifluoroacetate,
nn) 1-[1-Oxo-2-(4-chlorophenyl)hydrazino]ethyl-2-cyanopyrrolidine trifluoroacetate,
oo) 1-[1-Oxo-2-isopropyl-2-hydrazino]ethyl-2-cyano pyrrolidine trifluoroacetate,
pp) 3-[1-Oxo-2-(1-(4-methylcyclohexyl)-2-ethyl)hydrazino]ethyl-4-cyanothiazolidine trifluoroacetate,
qq) 3-[1-Oxo-2-(1-(4-morpholinocarbonyl)hydrazino)ethyl]-4-cyanothiazolidine trifluoroacetate,
rr) 3-[1-Oxo-2-(1-(4-methylcyclohexyl)-2-isopropyl)hydrazino]ethyl-4-cyanothiazolidine trifluoroacetate,
tt) 3-[1-Oxo-2-(1,2-bis-(2-(2-pyridyl)ethylaminocarbonyl)hydrazino)]ethyl-4-cyano thiazolidine bis trifluoroacetate,
uu) 3-[1-Oxo-2-(1-(4-tert-butyl cyclohexyl)hydrazino)]ethyl-4-cyanothiazolidine trifluoro acetate,
ww) 3-[1-Oxo-2-(1-(4-tertbutylcyclohexyl)hydrazino)]ethyl-4-cyanothiazolidine trifluoroacetate,
yy) 3-[1-Oxo-2-(1-isopropyl-4-piperidinyl)hydrazino)]ethyl-4-cyano thiazolidine trifluoroacetate,
zz) 3-[1-Oxo-2-(1-(1-(4-cyanophenylmethyl)-piperidin-4-yl)hydrazino)]ethyl-4-cyanothiazolidine bis trifluoroacetate,
aaa) 3-[1-Oxo-2-[1-(4-methylcyclohexyl)-2-(1-(3-pyridinylmethyl)-4-piperidinyl)]hydrazino]ethyl-4-cyanothiazolidine,
bbb) 3-[1-Oxo-2-[1-(4-methylcyclohexyl)-2-(1-isopropyl-4-piperidinyl)]hydrazino]ethyl-4-cyanothiazolidine,
ccc) 3-[1-Oxo-2-(1-(1-(4-methylphenylsulphonyl)-4-piperidinyl)-hydrazino)]ethyl-4-cyanothiazolidine trifluoroacetate,
ddd) 3-[1-Oxo-2-[1-methyl-2-(1-(4-methylphenylsulphonyl)-piperidin-4-yl)]hydrazino]ethyl-4-cyanothiazolidine trifluoroacetate,
eee) 3-[1-Oxo-2-(1-(1-(3-pyridinemethyl)-4-piperidinyl)hydrazino)]ethyl-4-cyanothiazolidine tris trifluoroacetate,
fff) 3-[1-Oxo-2-[1-methyl-2-(1-(4-cyanophenylmethyl)piperidin-4-yl)]hydrazino]ethyl-4-cyanothiazolidine bis trifluoroacetate,
ggg) 3-[1-Oxo-2-[1-methyl-2-(1-(3-pyridinylmethyl)-piperidin-4-yl)]hydrazino]ethyl-4-cyanothiazolidine tris trifluoroacetate,
hhh) 3-[1-Oxo-2-(1-(4-n propylcyclohexyl)hydrazino)]ethyl-4-cyanothiazolidine trifluoro acetate,
iii) 3-[1-Oxo-2-(1-(1-(4-nitrophenylmethyl)-piperidin-4-yl)hydrazino]ethyl-4-cyanothiazolidine trifluoroacetate,
jjj) 3-[1-Oxo-2-[1-(1-(4-chlorophenylsulphonyl)-piperidin-4-yl)]hydrazino]ethyl-4-cyanothiazolidine trifluoroacetate,
kkk) 3-[1-Oxo-2-(1-(1-norcamphoranyl)hydrazino)]ethyl-4-cyanothiazolidine trifluoroacetate,
lll) 3-[1-Oxo-2-(1-(4-n propylcyclohexyl)hydrazino)]ethyl-4-cyanothiazolidine trifluoroacetate,
mmm) 3-[1-Oxo-2-[1-(1-(4-methylcyclohexyl carbonyl)-piperidin-4-yl)]hydrazino]ethyl-4-cyanothiazolidine trifluoroacetate,
nnn) 3-[1-Oxo-2-(1-(1-acetyl)-piperidin-4-yl)hydrazino]ethyl-4-cyanothiazolidine trifluoroacetate,
ooo) 1,1-Dioxo-3-[1-oxo-2-(1-(4-methylcyclohexyl)hydrazino)]ethyl-4-cyanothiazolidine trifluoroacetate,
ppp) 3-[1-Oxo-2-(1-methyl-2-(4-methylcyclohexyl)hydrazino)]ethyl-4-cyanothiazolidine,
qqq) 3-[1-Oxo-2-(1-methyl-2-(4-methylcyclohexyl)hydrazino)]ethyl-4-cyanothiazolidine,
rrr) 3-[1-Oxo-2-(1-(1-(2,3-dichiorophenyl carbonyl)-piperidin-4-yl)hydrazino)]ethyl-4-cyanothiazolidine trifluoroacetate,
sss) 3-[1-Oxo-2-[1-methyl-2-(1-(4-chlorophenylsulphonyl)-piperidin-4-y1)]-hydrazino]ethyl-4-cyanothiazolidine,
ttt) 3-[1-Oxo-2-(1-(4-piperidinyl)hydrazino)]ethyl-4-cyanothiazolidine bis trifluoroacetate,
uuu) [1-Oxo-2-(1-(1-(4-chlorophenylsulphonyl)-piperidin-4-yl)-hydrazino)]ethyl-2-cyanopyrrolidine trifluoroacetate,
vvv) 3-[1-Oxo-2-(1-(4-methylcyclohexyl)-2-acetyl)hydrazino]ethyl-4-cyanothiazolidine,
xxx) 3-[1-Oxo-2-(1-(1-(tert-butyl carbonyl)-piperidin-4-yl)hydrazino)]ethyl-4-cyanotbiazolidine trifluoroacetate,
zzz) 3-[1-Oxo-2-(1-(1-methanesulphonylamino-4-cyclohexyl)hydrazino)]ethyl-4-cyanothiazolidine trifluoroacetate,
aaaa) 3-[1-Oxo-2-(1-(3,3,5-trimethyl cyclohexyl)-hydrazino)]ethyl-4-cyanothiazolidine trifluoroacetate,
bbbb) 3-[1-Oxo-2-(1-isopropyl-2-ethyl)-hydrazino]ethyl-4-cyanothiazolidine trifluoroacetate,
cccc) 3-[1-Oxo-2-[1-(1-phenylmethyl-piperidin-4-yl)]hydrazino]-ethyl-4-cyanothiazolidine trifluoroacetate,
dddd) 3-[1-Oxo-2-(1-(1-(4-chlorophenyl sulphonylamino-4-cyclohexyl) hydrazino)]ethyl-4-cyanothiazolidine trifluoro acetate,
ffff) 3-[1-Oxo-2-(1-(1-methanesulphonylamino-4-cyclohexyl)-2-isopropyl) hydrazino]ethyl-4-cyanothiazolidine trifluoroacetate, gggg) 3-[1-oxo-2-[1-(1(morpholinocarbonyl)-piperidin-4-yl)]hydrazino]ethyl-4-cyano-thiazolidine trifluoroacetate, hhhh) 3-[1-oxo-2-[1-(1-(methylsulphonyl)-piperidin-4-yl)]hydrazino]ethyl-4-cyanothiazolidine trifluoroacetate, iiii) 3-[1-oxo-2-[1-(1(methylsulphonyl)-piperidin-4-yl)-2-isopropyl]hydrazino]ethyl-4-cyanothiazolidine trifluoroacetate, jjjj) 3-[1-oxo-2-[1-(1-(methylsulphonyl)-piperidin-4-yl)-2-ethyl]hydrazino]ethyl-4-cyanothiazolidine trifluoroacetate, kkkk) 3-[1-oxo-2-[1-(1-(morpholinocarbonyl)-piperidin-4-yl)-2-ethyl]hydrazino]ethyl-4-cyanothiazolidine trifluoroacetate, llll) 3-[1-oxo-2-[1-(1-(N-ethylmethylaminocarbonyl)-piperidin-4-yl)]hydrazino]ethyl-4-cyanothiazolidine trifluoroacetate, oooo) 3-[1-oxo-2-[1-(1-(4-fluorobenzyl)aminocyclohexan-4-yl)]hydrazino]ethyl-4-cyanothiazolidine bis-trifluoroacetate, pppp) 3-[1-oxo-2-[1-(1-(4-fluorobenzyl)-piperidin-4-yl)]hydrazino]ethyl-4-cyanothiazolidine bis-trifluoroacetate, rrrr) 3-[1-oxo-2-[1-(1-(trimethyl acetamido)cyclohexan-4-yl)]hydrazino]ethyl-4-cyanothiazolidine trifluoroacetate, ssss) 3-[1-oxo-2-[1-(1-(methanesulphonyl)aminocyclohexan-4-yl)-2-ethyl]hydrazino]ethyl-4-cyanothiazolidine, tttt) 3-[1-oxo-2-[(1-(trimethyl acetamido)cyclohexan-4-yl)]hydrazino]ethyl-4-cyanothiazolidine trifluoroacetate, vvvv) 3-[1-oxo-2- [1-(4-fluorobenzoyl)aminocyclohexan-4-yl)]hydrazino]ethyl-4-cyanothiazolidine trifluoroacetate, and jjjjj) 3-[1-oxo-2-(1-(1-methanesulphonylamino-4-cyclohexyl)hydrazino)]ethyl-4-cyanothiazolidine hydrochloride.

3. A pharmaceutical composition comprising a compound of claim 1, or a pharmaceutically acceptable salt or hydrate thereof, in association with a pharmaceutically acceptable carrier, diluent or excepient.

4. The pharmaceutical composition as claimed in claim 3, wherein the said compound is selected from the group consisting of:

c) 1-[1-Oxo-2-((1-phenyl)-hydrazino)]ethyl-2-cyano pyrrolidine trifluoroacetate, d) 1-[1-Oxo-2-(1-hydrazino)]ethyl-2-cyano pyrrolidine trifluoroacetate, e) 3-[1-Oxo-2-((2-(1,1-dimethyl ethyl oxy carbonyl))hydrazino)]ethyl-4-cyano thiazolidine, f) 1-[1-Oxo-2-((2-(1,1-dimethylethyloxy carbonyl))-1-phenyl hydrazino)]ethyl-2-cyano pyrrolidine, g) 1-[1-Oxo-2-((2-(1,1-dimethylethyl oxy carbonyl))hydrazino)]ethyl-2-cyano pyrrolidine, h) 1-[1-Oxo-2-((1-(4-nitrophenylmethyl))hydrazino)]ethyl-2-cyano pyrrolidine trifluoroacetate, i) 3-[1-Oxo-2-((1-phenyl)hydrazino)]ethyl-4-cyano thiazolidine trifluoroacetate, j) 1-[1-Oxo-2-(1-(2-methylpropyl)hydrazino)]ethyl-2-cyano pyrrolidine trifluoroacetate, k) 1-[1-Oxo-2-((1-phenylmethyl)hydrazino)]ethyl-2-cyano pyrrolidine trifluoroacetate, l) 1-[1-Oxo-2-((1-methyl)ethyl)hydrazino)]ethyl-2-cyano pyrrolidine trifluoroacetate, m) 1-[1-Oxo-2-((2,2-diethyl)-hydrazino)]ethyl-2-cyano thiazolidine, n) 1-[1-Oxo-2-((1-ethyl)hydrazino)]ethyl-2-cyano pyrrolidine trifluoroacetate, o) 3-[1-Oxo-2-(1-hydrazino)]ethyl-4-cyano thiazolidine trifluoroacetate, p) 3-[1-Oxo-2-((1-phenylmethyl)hydrazino)]ethyl-4-cyano thiazolidine trifluoroacetate, q) 3-[1-Oxo-2-((1-(4-nitrophenylmethyl))hydrazino)]ethyl-4-cyano thiazolidine trifluoroacetate, r) 1-[1-Oxo-2-((1-Cyclopentyl)-hydrazino)]ethyl-2-cyano pyrrolidine trifluoroacetate, s) 3-[1-Oxo-2-((1-Cyclopentyl)-hydrazino)]ethyl-4-cyano thiazolidine trifluoroacetate, t) 1-[1-Oxo-2-((1-Cyclohexyl)-hydrazino)]ethyl-2-cyano pyrrolidine trifluoroacetate, u) 3-[1-Oxo-2-((1-Cyclohexyl)-hydrazino)]ethyl-4-cyano thiazolidine trifluoroacetate, v) 1-[1-Oxo-2-((1-methylpropyl)hydrazino)]ethyl-2-cyano pyrrolidine trifluoroacetate, w) 3-[1-Oxo-2-((1-methylpropyl)hydrazino)]ethyl-4-cyano thiazolidine trifluoroacetate, x) 1-[1-Oxo-2-((1-Phenyl sulphonyl)hydrazino)]ethyl-2-cyano pyrrolidine trifluoroacetate, y) 3-[1-Oxo-2-((1-(4-methyl)cyclohexyl)hydrazino)]ethyl-4-cyano thiazolidine trifluoroacetate, z) 1-[1-Oxo-2-((4-Methyl)cyclohexyl)hydrazino)]ethyl-2-cyano pyrrolidine trifluoroacetate, aa) 1-[1-Oxo-2-(1-(2-Pyridyl)-hydrazino)]ethyl-2-cyano pyrrolidine bis-trifluoroacetate, bb) 3-[1-Oxo-2-((1-Cycloheptyl)-hydrazino)]ethyl-4-cyano thiazolidine trifluoroacetate, cc) 3-[1-Oxo-2-((1-(4-methyl)cyclohexyl)-hydrazino)]ethyl-4-cyano thiazolidine trifluoroacetate, dd) 1-[1-Oxo-2-((1-Cycloheptyl)-hydrazino)]ethyl-2-cyano pyrrolidine trifluoroacetate, ee) [4-Cyano-3-(1-isopropylhydrazino)carbonyl thiazolidine hydrochloride], ff) [2-Cyano-1-(1-cyclohexyl hydrazino)carbonyl pyrrolidine hydrochloride], gg) [4-Cyano-3-(1-cyclohexylhydrazino)carbonyl thiazolidine hydrochloride], hh) 1-[1-Oxo-2-(2-cyclohexyl)hydrazino]ethyl-2-cyanopyrrolidine trifluoroacetate, ii) [4-Cyano-3-(1-phenyl hydrazino)carbonyl thiazolidine trifluoroacetate], jj) 3-[1-Oxo-2-(1-cyclohexyl-2-isopropyl)hydrazino]ethyl-4-cyanothiazolidine hydrochloride, kk) 1-[1-Oxo-2-(4-methylcyclohexyl)hydrazino]ethyl-2-cyanopyrrolidine trifluoroacetate, ll) 1-[1-Oxo-2-(1-cyclohexyl-2-isopropyl)hydrazino] ethyl-2-cyano pyrrolidine, mm) 1-[1-Oxo-2-(1-(4-methylcyclohexylmethyl)hydrazino)]ethyl-2-cyanopyrrolidine trifluoroacetate, nn) 1-[1-Oxo-2-(4-chlorophenyl)hydrazino]ethyl-2-cyanopyrrolidine trifluoroacetate, oo) 1-[1-Oxo-2-isopropyl-2-hydrazino]ethyl-2-cyano pyrrolidine trifluoroacetate, pp) 3-[1-Oxo-2-(1-(4-methylcyclohexyl)-2-ethyl)hydrazino]ethyl-4-cyanothiazolidine trifluoroacetate, qq) 3-[1-Oxo-2-(1-(4-morpholinocarbonyl)hydrazino) ethyl]-4-cyanothiazolidine trifluoroacetate, rr) 3-[1-Oxo-2-(1-(4-methylcyclohexyl)-2-isopropyl)hydrazino]ethyl-4-cyanothiazolidine trifluoroacetate, tt) 3-[1-Oxo-2-(1,2-bis-(2-(2-pyridyl)ethylaminocarbonyl)hydrazino)]ethyl-4-cyano thiazolidine bis trifluoroacetate, uu) 3-[1-Oxo-2-(1-(4-tert-butyl cyclohexyl)hydrazino)] ethyl-4-cyanothiazolidine trifluoro acetate, ww) 3-[1-Oxo-2-(1-(4-tertbutylcyclohexyl)hydrazino)]ethyl-4-cyanothiazolidine trifluoroacetate,
yy) 3-[1-Oxo-2-(1-isopropyl-4-piperidinyl)hydrazino)]ethyl-4-cyano thiazolidine trifluoroacetate,
zz) 3-[1-Oxo-2-(1-(1-(4-cyanophenylmethyl)-piperidin-4-yl)hydrazino)]ethyl-4-cyanothiazolidine bis trifluoroacetate,
aaa) 3-[1-Oxo-2-[1-(4-methylcyclohexyl)-2-(1-(3-pyridinylmethyl)-4-piperidinyl)]hydrazino]ethyl-4-cyanothiazolidine,
bbb) 3-[1-Oxo-2-[1-(4-methylcyclohexyl)-2-(1-isopropyl-4-piperidinyl)]hydrazino]ethyl-4-cyanothiazolidine,
ccc) 3-[1-Oxo-2-(1-(1-(4-methylphenylsulphonyl)-4-piperidinyl)-hydrazino)]ethyl-4-cyanothiazolidine trifluoroacetate,
ddd) 3-[1-Oxo-2-[1-methyl-2-(1-(4-methylphenylsulphonyl)-piperidin-4-yl)]hydrazino]ethyl-4-cyanothiazolidine trifluoroacetate,
eee) 3-[1-Oxo-2-(1-(1-(3-pyridinemethyl)-4-piperidinyl)hydrazino)]ethyl-4-cyanothiazolidine bis trifluoroacetate,
fff) 3-[1-Oxo-2-[1-methyl-2-(1-(4-cyanophenylmethyl)piperidin-4-yl)]hydrazino]ethyl-4-cyanothiazolidine bis trifluoroacetate,
ggg) 3-[1-Oxo-2-[1-methyl-2-(1-(3-pyridinylmethyl)-piperidin-4-yl)]hydrazino]ethyl-4-cyanothiazolidine tris trifluoroacetate,
hhh) 3-[1-Oxo-2-(1-(4-n propylcyclohexyl)hydrazino)]ethyl-4-cyanothiazolidine trifluoro acetate,
iii) 3-[1-Oxo-2-(1-(1-(4-nitrophenylmethyl)-piperidin-4-yl)hydrazino]ethyl-4-cyanothiazolidine trifluoroacetate,
jjj) 3-[1-Oxo-2-[1-(1-(4-chlorophenylsulphonyl)-piperidin-4-yl)]hydrazino]ethyl-4-cyanothiazolidine trifluoroacetate,
kkk) 3-[1-Oxo-2-(1-(1-norcamphoranyl)hydrazino)]ethyl-4-cyanothiazolidine trifluoroacetate,
lll) 3-[1-Oxo-2-(1-(4-n propylcyclohexyl)hydrazino)]ethyl-4-cyanothiazolidine trifluoroacetate,
mmm) 3-[1-Oxo-2-[1-(1-(4-methylcyclohexyl carbonyl)-piperidin-4-yl)]hydrazino]ethyl-4-cyanothiazolidine trifluoroacetate,
nnn) 3-[1-Oxo-2-(1-(1-acetyl)-piperidin-4-yl)hydrazino]ethyl-4-cyanothiazolidine trifluoroacetate,
ooo) 1,1-Dioxo-3-[1-oxo-2-(1-(4-methylcyclohexyl)hydrazino)]ethyl-4-cyanothiazolidine trifluoroacetate,
ppp) 3-[1-Oxo-2-(1-methyl-2-(4-methylcyclohexyl)hydrazino)]ethyl-4-cyanothiazolidine,
qqq) 3-[1-Oxo-2-(1-methyl-2-(4-methylcyclohexyl)hydrazino)]ethyl-4-cyanothiazolidine,
rrr) 3-[1-Oxo-2-(1-(1-(2,3-dichlorophenyl carbonyl)-piperidin-4-yl)hydrazino)]ethyl-4-cyanothiazolidine trifluoroacetate,
sss) 3-[1-Oxo-2-[1-methyl-2-(1-(4-chlorophenylsulphonyl)-piperidin-4-yl)]-hydrazino]ethyl-4-cyanothiazolidine,
ttt) 3-[1-Oxo-2-(1-(4-piperidinyl)hydrazino)]ethyl-4-cyanothiazolidine bis trifluoroacetate,
uuu) [1-Oxo-2-(1-(1-(4-chlorophenylsulphonyl)-piperidin-4-yl)-hydrazino)]ethyl-2-cyanopyrrolidine trifluoroacetate,
vvv) 3-[1-Oxo-2-(1-(4-methylcyclohexyl)-2-acetyl)hydrazino]ethyl-4-cyanothiazolidine,
xxx) 3-[1-Oxo-2-(1-(1-(tert-butyl carbonyl)-piperidin-4-yl)hydrazino]ethyl-4-cyanothiazolidine trifluoroacetate,
zzz) 3-[1-Oxo-2-(1-(1-methanesulphonylamino-4-cyclohexyl)hydrazino)]ethyl-4-cyanothiazolidine trifluoroacetate,
aaaa) 3-[1-Oxo-2-(1-(3,3,5-trimethyl cyclohexyl)-hydrazino)]ethyl-4-cyanothiazolidine trifluoroacetate,
bbbb) 3-[1-Oxo-2-(1-isopropyl-2-ethyl)-hydrazino]ethyl-4-cyanothiazolidine trifluoroacetate,
cccc) 3-[1-Oxo-2-[1-(1-phenylmethyl-piperidin-4-yl)]-hydrazino]-ethyl-4-cyanothiazolidine trifluoroacetate,
dddd) 3-[1-Oxo-2-(1-(1-(4-chlorophenyl sulphonylamino-4-cyclohexyl) hydrazino)]ethyl-4-cyanothiazolidine trifluoroacetate,
ffff) 3-[1-Oxo-2-(1-(1-methanesulphonylamino-4-cyclohexyl)-2-isopropyl) hydrazino]ethyl-4-cyanothiazolidine trifluoroacetate,
gggg) 3-[1-oxo-2-[1-(1(morpholinocarbonyl)-piperidin-4-yl)]hydrazino]ethyl-4-cyano-thiazolidine trifluoroacetate,
hhhh) 3-[1-oxo-2-[1-(1-(methylsulphonyl)-piperidin-4-yl)]hydrazino]ethyl-4-cyanothiazolidine trifluoroacetate,
iiii) 3-[1-oxo-2-[1-(1(methylsulphonyl)-piperidin-4-yl)-2-isopropyl]hydrazino]ethyl-4-cyanothiazolidine trifluoroacetate,
jjjj) 3-[1-oxo-2-[1-(1-(methylsulphonyl)-piperidin-4-yl)-2-ethyl]hydrazino]ethyl-4-cyanothiazolidine trifluoroacetate,
kkkk) 3-[1-oxo-2-[1-(1-(morpholinocarbonyl)-piperidin-4-yl)-2-ethyl]hydrazino]ethyl-4-cyanothiazolidine trifluoroacetate,
llll) 3-[1-oxo-2-[1-(1-(N-ethylmethylaminocarbonyl)-piperidin-4-yl)]hydrazino]ethyl-4-cyanothiazolidine trifluoroacetate,
oooo) 3-[1-oxo-2-[1-(1-(4-fluorobenzyl)aminocyclohexan-4-yl)]hydrazino]ethyl-4-cyanothiazolidine bis-trifluoroacetate,
pppp) 3-[1-oxo-2-[1-(1-(4-fluorobenzyl)-piperidin-4-yl)]hydrazino]ethyl-4-cyanothiazolidine bis-trifluoroacetate,
rrrr) 3-[1-oxo-2-[1-(1-(trimethyl acetamido)cyclohexan-4-yl)]hydrazino]ethyl-4-cyanothiazolidine trifluoroacetate,
ssss) 3-[1-oxo-2-[1-(1-(methanesulphonyl)aminocyclohexan-4-yl)-2-ethyl]hydrazino]ethyl-4-cyanothiazolidine,
tttt) 3-[1-oxo-2-[(1-(trimethyl acetamido)cyclohexan-4-yl)]hydrazino]ethyl-4-cyanothiazolidine trifluoroacetate,
vvvv) 3-[1-oxo-2-[1-(4-fluorobenzoyl)aminocyclohexan-4-yl)]hydrazino]ethyl-4-cyanothiazolidine trifluoroacetate, and
jjjjj) 3-[1-oxo-2-(1-(1-methanesulphonylamino-4-cyclohexyl)hydrazino)]ethyl-4-cyanothiazolidine hydrochloride.

5. A method of treating diabetes and delaying the onset and progression of diabetes in a mammal which comprises administering an effective amount of a compound of claim 1, or a pharmaceutically acceptable salt or hydrate thereof, in association with a pharmaceutically acceptable carrier, diluent or excepient, to said mammal.

6. The method as claimed in claim 5 wherein the said compound is selected from the group consisting of:
c) 1-[1-Oxo-2-((1-phenyl)-hydrazino)]ethyl-2-cyano pyrrolidine trifluoroacetate,
d) 1-[1-Oxo-2-(1-hydrazino)]ethyl-2-cyano pyrrolidine trifluoroacetate, e) 3-[1-Oxo-2-((2-(1,1-dimethyl ethyl oxy carbonyl))hydrazino)]ethyl-4-cyano thiazolidine,
f) 1-[1-Oxo-2-((2-(1,1-dimethylethyloxy carbonyl))-1-phenyl hydrazino)]ethyl-2-cyano pyrrolidine,
g) 1-[1-Oxo-2-((2-(1,1-dimethylethyl oxy carbonyl))hydrazino)]ethyl-2-cyano pyrrolidine,
h) 1-[1-Oxo-2-((1-(4-nitrophenylmethyl))hydrazino)]ethyl-2-cyano pyrrolidine trifluoroacetate,
i) 3-[1-Oxo-2-((1-phenyl)hydrazino)]ethyl-4-cyano thiazolidine trifluoroacetate,
j) 1-[1-Oxo-2-(1-(2-methylpropyl)hydrazino)]ethyl-2-cyano pyrroiidine trifluoroacetate,
k) 1-[1-Oxo-2-((1-phenylmethyl)hydrazino)]ethyl-2-cyano pyrrolidine trifluoroacetate,
l) 1-[1-Oxo-2-((1-(1-methyl)ethyl)hydrazino)]ethyl-2-cyano pyrrolidine trifluoroacetate,
m) 1-[1-Oxo-2-((2,2-diethyl)-hydrazino)]ethyl-2-cyano thiazolidine,
n) 1-[1-Oxo-2-((1-ethyl)hydrazino)]ethyl-2-cyano pyrrolidine trifluoroacetate,
o) 3-[1-Oxo-2-(1-hydrazino)]ethyl-4-cyano thiazolidine trifluoroacetate,
p) 3-[1-Oxo-2-((1-phenylmethyl)hydrazino)]ethyl-4-cyano thiazolidine trifluoroacetate,
q) 3-[1-Oxo-2-((1-(4-nitrophenylmethyl))hydrazino)]ethyl-4-cyano thiazolidine trifluoroacetate,
r) 1-[1-Oxo-2-((1-Cyclopentyl)-hydrazino)]ethyl-2-cyano pyrrolidine trifluoroacetate,
s) 3-[1-Oxo-2-((1-Cyclopentyl)-hydrazino)]ethyl-4-cyano thiazolidine trifluoroacetate,
t) 1-[1-Oxo-2-((1-Cyclohexyl)-hydrazino)]ethyl-2-cyano pyrrolidine trifluoroacetate,
u) 3-[1-Oxo-2-((1-Cyclohexyl)-hydrazino)]ethyl-4-cyano thiazolidine trifluoroacetate,
v) 1-[1-Oxo-2-((1-methylpropyl)hydrazino)]ethyl-2-cyano pyrrolidine trifluoroacetate,
w) 3-[1-Oxo-2-((1-methylpropyl)hydrazino)]ethyl-4-cyano thiazolidine trifluoroacetate,
x) 1-[1-Oxo-2-((1-Phenyl sulphonyl)hydrazino)]ethyl-2-cyano pyrrolidine trifluoroacetate,
y) 3-[1-Oxo-2-((1-(4-methyl)cyclohexyl)hydrazino)]ethyl-4-cyano thiazolidine trifluoroacetate,
z) 1-[1-Oxo-2-((4-Methyl)cyclohexyl)hydrazino)]ethyl-2-cyano pyrrolidine trifluoroacetate,
aa) 1-[1-Oxo-2-(1-(2-Pyridyl)-hydrazino)]ethyl-2-cyano pyrrolidine bis-trifluoroacetate,
bb) 3-[1-Oxo-2-((1-Cycloheptyl)-hydrazino)]ethyl-4-cyano thiazolidine trifluoroacetate,
cc) 3-[1-Oxo-2-((1-(4-methyl)cyclohexyl)-hydrazino)]ethyl-4-cyano thiazolidine trifluoroacetate,
dd) 1-[1-Oxo-2-((1-Cycloheptyl)-hydrazino)]ethyl-2-cyano pyrrolidine trifluoroacetate,
ee) [4-Cyano-3-(1-isopropylhydrazino)carbonyl thiazolidine hydrochloride],
ff) [2-Cyano-1-(1-cyclohexyl hydrazino)carbonyl pyrrolidine hydrochloride],
gg) [4-Cyano-3-(1-cyclohexylhydrazino)carbonyl thiazolidine hydrochloride],
hh) 1-[1-Oxo-2-(2-cyclohexyl)hydrazino]ethyl-2-cyanopyrrolidine trifluoroacetate,
ii) [4-Cyano-3-(1-phenyl hydrazino)carbonyl thiazolidine trifluoroacetate],
jj) 3-[1-Oxo-2-(1-cyclohexyl-2-isopropyl)hydrazino] ethyl-4-cyanothiazolidine hydrochloride,
kk) 1-[1-Oxo-2-(4-methylcyclohexyl)hydrazino]ethyl-2-cyanopyrrolidine trifluoroacetate,
ll) 1-[1-Oxo-2-(1-cyclohexyl-2-isopropyl)hydrazino] ethyl-2-cyano pyrrolidine,
mm) 1-[1-Oxo-2-(1-(4-methylcyclohexylmethyl)hydrazino)]ethyl-2-cyanopyrrolidine trifluoroacetate,
nn) 1-[1-Oxo-2-(4-chlorophenyl)hydrazino]ethyl-2-cyanopyrrolidine trifluoroacetate,
oo) 1-[1-Oxo-2-isopropyl-2-hydrazino]ethyl-2-cyano pyrrolidine trifluoroacetate,
pp) 3-[1-Oxo-2-(1-(4-methylcyclohexyl)-2-ethyl)hydrazino]ethyl-4-cyanothiazolidine trifluoroacetate,
qq) 3-[1-Oxo-2-(1-(4-morpholinocarbonyl)hydrazino) ethyl]-4-cyanothiazolidine trifluoroacetate,
rr) 3-[1-Oxo-2-(1-(4-methylcyclohexyl)-2-isopropyl)hydrazino]ethyl-4-cyanothiazolidine trifluoroacetate,
tt) 3-[1-Oxo-2-(1,2-bis-(2-(2-pyridyl)ethylaminocarbonyl)hydrazino)]ethyl-4-cyano thiazolidine bis trifluoroacetate,
uu) 3-[1-Oxo-2-(1-(4-tert-butyl cyclohexyl)hydrazino)] ethyl-4-cyanothiazolidine trifluoro acetate,
ww) 3-[1-Oxo-2-(1-(4-tertbutylcyclohexyl)hydrazino)] ethyl-4-cyanothiazolidine trifluoroacetate,
yy) 3-[1-Oxo-2-(1-isopropyl-4-piperidinyl)hydrazino)] ethyl-4-cyano thiazolidine trifluoroacetate,
zz) 3-[1-Oxo-2-(1-(1-(4-cyanophenylmethyl)-piperidin-4-yl)hydrazino)]ethyl-4-cyanothiazolidine bis trifluoroacetate,
aaa) 3-[1-Oxo-2-[1-(4-methylcyclohexyl)-2-(1-(3-pyridinylmethyl)-4-piperidinyl)]hydrazino]ethyl-4-cyanothiazolidine,
bbb) 3-[1-Oxo-2-[1-(4-methylcyclohexyl)-2-(1-isopropyl-4-piperidinyl)]hydrazino]ethyl-4-cyanothiazolidine,
ccc) 3-[1-Oxo-2-(1-(1-(4-methylphenylsulphonyl)-4-piperidinyl)-hydrazino)]ethyl-4-cyanothiazolidine trifluoroacetate,
ddd) 3-[1-Oxo-2-[1-methyl-2-(1-(4-methylphenylsulphonyl)-piperidin-4-yl)]hydrazino]ethyl-4-cyanothiazolidine trifluoroacetate,
eee) 3-[1-Oxo-2-(1-(1-(3-pyridinemethyl)-4-piperidinyl) hydrazino)]ethyl-4-cyanothiazolidine tris trifluoroacetate,
fff) 3-[1-Oxo-2-[1-methyl-2-(1-(4-cyanophenylmethyl) piperidin-4-yl)]hydrazino]ethyl-4-cyanothiazolidine bis trifluoroacetate,
ggg) 3-[1-Oxo-2-[1-methyl-2-(1-(3-pyridinylmethyl)-piperidin-4-yl)]hydrazino]ethyl-4-cyanothiazolidine tris trifluoroacetate,
hhh) 3-[1-Oxo-2-(1-(4-n propylcyclohexyl)hydrazino)] ethyl-4-cyanothiazolidine trifluoro acetate,
iii) 3-[1-Oxo-2-(1-(1-(4-nitrophenylmethyl)-piperidin-4-yl)hydrazino]ethyl-4-cyanothiazolidine trifluoroacetate,
jjj) 3-[1-Oxo-2-[1-(1-(4-chlorophenylsulphonyl)-piperidin-4-yl)]hydrazino]ethyl-4-cyanothiazolidine trifluoroacetate,
kkk) 3-[1-Oxo-2-(1-(1-norcamphoranyl)hydrazino)] ethyl-4-cyanothiazolidine trifluoroacetate,
lll) 3-[1-Oxo-2-(1-(4-n propylcyclohexyl)hydrazino)] ethyl-4-cyanothiazolidine trifluoroacetate,
mmm) 3-[1-Oxo-2-[1-(1-(4-methylcyclohexyl carbonyl)-piperidin-4-yl)]hydrazino]ethyl-4-cyanothiazolidine trifluoroacetate,
nnn) 3-[1-Oxo-2-(1-(1-acetyl)-piperidin-4-yl)hydrazino] ethyl-4-cyanothiazolidine trifluoroacetate,
ooo) 1,1-Dioxo-3-[1-oxo-2-(1-(4-methylcyclohexyl)hydrazino)]ethyl-4-cyanothiazolidine trifluoroacetate, ppp) 3-[1-Oxo-2-(1-methyl-2-(4-methylcyclohexyl)hydrazino)]ethyl-4-cyanothiazolidine,
qqq) 3-[1-Oxo-2-(1-methyl-2-(4-methylcyclohexyl)hydrazino)]ethyl-4-cyanothiazolidine,
rrr) 3-[1-Oxo-2-(1-(1-(2,3-dichlorophenyl carbonyl)-piperidin-4-yl)hydrazino)]ethyl-4-cyanothiazolidine trifluoroacetate,
sss) 341-Oxo-2-[1-methyl-2-(1-(4-chlorophenylsulphonyl)-piperidin-4-yl)]-hydrazino]ethyl-4-cyanothiazolidine,
ttt) 3-[1-Oxo-2-(1-(4-piperidinyl)hydrazino)]ethyl-4-cyanothiazolidine bis trifluoroacetate,
uuu) [1-Oxo-2-(1-(1-(4-chlorophenylsulphonyl)-piperidin-4-yl)-hydrazino)]ethyl-2-cyanopyrrolidine trifluoroacetate,
vvv) 3-[1-Oxo-2-(1-(4-methylcyclohexyl)-2-acetyl)hydrazino]ethyl-4-cyanothiazolidine,
xxx) 3-[1-Oxo-2-(1-(1-(tert-butyl carbonyl)-piperidin-4-yl)hydrazino)]ethyl-4-cyanothiazolidine trifluoroacetate,
zzz) 3-[1-Oxo-2-(1-(1-methanesulphonylamino-4-cyclohexyl)hydrazino)]ethyl-4-cyanothiazolidine trifluoroacetate,
aaaa) 3-[1-Oxo-2-(1-(3,3,5-trimethyl cyclohexyl)-hydrazino)]ethyl-4-cyanothiazolidine trifluoroacetate,
bbbb) 3-[1-Oxo-2-(1-isopropyl-2-ethyl)-hydrazino]-ethyl-4-cyanothiazolidine trifluoroacetate,
cccc) 3-[1-Oxo-2-[1-(1-phenylmethyl-piperidin-4-yl)]-hydrazino]-ethyl-4-cyanothiazolidine trifluoroacetate,
dddd) 3-[1-Oxo-2-(1-(1-(4-chlorophenyl sulphonylamino-4-cyclohexyl) hydrazino)]ethyl-4-cyanothiazolidine trifluoroacetate,
ffff) 3-[1-Oxo-2-(1-(1-methanesulphonylamino-4-cyclohexyl)-2-isopropyl) hydrazino]ethyl-4-cyanothiazolidine trifluoroacetate,
gggg) 3-[1-oxo-2-[1-(1(morpholinocarbonyl)-piperidin-4-yl)]hydrazino]ethyl-4-cyano-thiazolidine trifluoroacetate,
hhhh) 3-[1-oxo-2-[1-(1-(methylsulphonyl)-piperidin-4-yl)]hydrazino]ethyl-4-cyanothiazolidine trifluoroacetate,
iiii) 3-[1-oxo-2-[1-(1(methylsulphonyl)-piperidin-4-yl)-2-isopropyl]hydrazino]ethyl-4-cyanothiazolidine trifluoroacetate,
jjjj) 3-[1-oxo-2-[1-(1-(methylsulphonyl)-piperidin-4-yl)-2-ethyl]hydrazino]ethyl-4-cyanothiazolidine trifluoroacetate,
kkkk) 3-[1-oxo-2-[1-(1-(morpholinocarbonyl)-piperidin-4-yl)-2-ethyl]hydrazino]ethyl-4-cyanothiazolidine trifluoroacetate,
llll) 3-[1-oxo-2-[1-(1-(N-ethylmethylaminocarbonyl)-piperidin-4-yl)]hydrazino]ethyl-4-cyanothiazolidine trifluoroacetate,
oooo) 3-[1-oxo-2-[1-(1-(4-fluorobenzyl)aminocyclohexan-4-yl)]hydrazino]ethyl-4-cyanothiazolidine bis-trifluoroacetate,
pppp) 3-[1-oxo-2-[1-(1-(4-fluorobenzyl)-piperidin-4-yl)]hydrazino]ethyl-4-cyanothiazolidine bis-trifluoroacetate,
rrrr) 3-[1-oxo-2-[1-(1-(trimethyl acetamido)cyclohexan-4-yl)]hydrazino]ethyl-4-cyanothiazolidine trifluoroacetate,
ssss) 3-[1-oxo-2-[1-(1-(methanesulphonyl)aminocyclohexan-4-yl)-2-ethyl]hydrazino]ethyl-4-cyanothiazolidine,
tttt) 3-[1-oxo-2-[(1-(trimethyl acetamido)cyclohexan-4-yl)]hydrazino]ethyl-4-cyanothiazolidine trifluoroacetate,
vvvv) 3-[1-oxo-2-[1-(4-fluorobenzoyl)aminocyclohexan-4-yl)]hydrazino]ethyl-4-cyanothiazolidine trifluoroacetate, and
jjjjj) 3-[1-oxo-2-(1-(1-methanesulphonylamino-4-cyclohexyl)hydrazino)]ethyl-4-cyanothiazolidine hydrochloride.

7. The method of claim 5, wherein said mammal is a human.

8. A process for preparing compounds of formulas 13 and

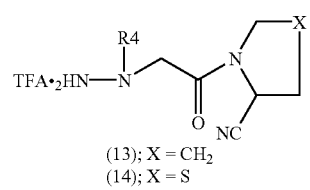

(13); X = CH$_2$
(14); X = S wherein R4 is selected from hydrogen, perhaloalkyl, —(CO)NR8R9, —(CO)R8, —(CO)OR8, —SO$_2$R8, —SOR8, substituted or unsubstituted groups selected from linear or branched (C$_1$–C$_{12}$)alkyl, (C$_2$–C$_{12}$)alkenyl, (C$_3$–C$_7$)cycloalkyl, (C$_5$–C$_7$)cycloalkenyl, bicloalkyl, amidino bicycloalkenyl, heterocycloalkyl, aryl, aralkyl, heteroaryl, heteroaralkyl, wherein one or more heteroatoms are independently selected from O, N or S;

R8 and R9 are independently selected from hydrogen or a substituted and unsubstituted group selected from linear or branched (C$_1$–C$_{12}$)alkyl, alkoxyaryl, alkoxyalkyl, alkoxycycloalkyl, alkoxyaryl, perhaloalkyl, (C$_2$–C$_{12}$)alkenyl, (C$_3$–C$_7$)cycloalkyl, perhalocycloalkyl, haloheterocycloalkyl, cyanoheterocycloalkyl, perhaloheterocycloalkyl, (C$_5$–C$_7$)cycloalkenyl, bicloalkyl, bicycloalkenyl, heterocycloalkyl, aryl, aralkyl, heteroaryl, heteroaralkyl, perhaloaryl, perhaloheteroaryl, wherein the groups represented by R8 and R9 when substituted, the substituents are optionally and independently bridged by —(CO)—, —(CO)O, —(CO)NH—, —NH—, —NR8-, —O—, —S—, —(SO)—, —(SO$_2$)—, —(SO$_2$)NH—, —NH(SO$_2$)—, —O(CO)— or —NH(CO)—; and are selected from halogen, hydroxy, nitro cyano, amino, oxo, oxime, unsubstittued or substituted by R10 for the groups selected from linear or branched (C$_1$–C$_8$)alkyl, (C$_3$–C$_7$) cycloalkyl, alkylcycloalkyl, perhaloalkyl, perhalocycloalkyl, aryl, aralkyl, alkylaryl, alkylheteroaryl, aralkoxylalkyl, perhaloaryl, alkylheterocycloalkyl, heterocycloalkyl, perhaloheterocyclyloalkyl, heteroaryl, heteroaralkyl, alkylaryl, perhaloheteroaryl, acyl, acyloxy, acylamino, alkamino, arylamino, aralkoxy, alkoxyalkyl, alkylthio, thioalkyl, arylthio, thioaryl, carboxylic acid or its derivatives, or sulfonic acid or its derivatives wherein the groups/substituents present on same or adjacent atoms such as carbon or nitrogen, together optionally and independently may form a five or a six or a seven membered ring optionally containing one or more double bonds and optionally contaings one or more heteroatoms selected from O, N or S;

and wherein

R10 is independently selected from halogen, hydroxy, nitro, cyano, amino, oxo or oxime; and "Boc" in process step (a) below stands for "tertiary Butyloxy Carbonyl", comprising the steps of:

a) reacting chloroacyl-2-cyanopyrrolidine or chloroacyl-4-cyanothiazolidine with N-substituted Boc-carbazate using aprotic solvent in the presence of a base at 40–110° C. for 8–50 hrs, wherein said N-substituted Boc-carbazate is obtained from aldehyde and ketone; and b) deprotecting the resulting coupled product using trifluoroacetic acid at 5–30° C. for 0.25–2 hrs to obtain the desired product.

9. The process as claimed in claim 8, wherein in step (a) of the process said aprotic solvent is acetonitrile, tetrahydrofuran, dimethylformamide or dioxane, and said base is tertiary amine or alkali carbonate.

10. The process as claimed in claim 9 wherein in step (a) of the process said aprotic solvent is tetrahydrofuran, and said base is potassium carbonate in the presence of a catalytic amount of potassium iodide.

11. A process for preparing compounds of formulas 9c and 10c

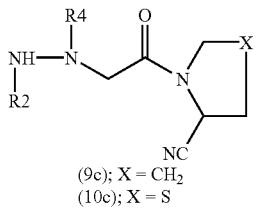

(9c); X = CH$_2$
(10c); X = S wherein

R4 and R2 are independently selected from hydrogen, perhaloalkyl, —(CO)NR8R9, —(CO)R8, —(CO)OR8, —SO$_2$R8, —SOR8, substituted or unsubstituted groups selected from linear or branched (C$_1$–C$_{12}$)alkyl, (C$_2$–C$_{12}$)alkenyl, (C$_3$–C$_7$)cycloalkyl, (C$_5$–C$_7$)cycloalkenyl, bicycloalkyl, amidino bicycloalkenyl, heterocycloalkyl, aryl, aralkyl, heteroaryl, heteroaralkyl, wherein one or more heteroatoms are independently selected from O, N or S;

R8 and R9 are independently selected from hydrogen or a substituted and unsubstituted group selected from linear or branched (C$_1$–C$_{12}$)alkyl, alkoxyaryl, alkoxyalkyl, alkoxycycloalkyl, alkoxyaryl, perhaloalkyl, (C$_2$–C$_{12}$)alkenyl, (C$_3$–C$_7$)cycloalkyl, perhalocycloalkyl, haloheterocycloalkyl, cyanoheterocycloalkyl, perhaloheterocycloalkyl, (C$_5$–C$_7$)cycloalkenyl, bicycloalkyl, bicycloalkenyl, heterocycloalkyl, aryl, aralkyl, heteroaryl, heteroaralkyl, perhaloaryl, perhaloheteroaryl, wherein the groups represented by R8 and R9 when substituted, the substituents are optionally and independently bridged by —(CO)—, —(CO)O, —(CO)NH—, —NH—, —NR8-, —O—, —S—, —(SO)—, —(SO$_2$)—, —(SO$_2$)NH—, —NH(SO$_2$)—, —O(CO)— or —NH(CO)—; and are selected from halogen, hydroxy, nitro cyano, amino, oxo, oxime, unsubstittued or substituted by R10 for the groups selected from linear or branched (C$_1$–C$_8$)alkyl, (C$_3$–C$_7$)cycloalkyl, alkylcycloalkyl, perhaloalkyl, perhalocycloalkyl, aryl, aralkyl, alkylaryl, atkylheteroaryl, aralkoxyalkyl, perhaloaryl, alkylheterocycloalkyl, heterocycloalkyl, perhaloheterocyclyloalkyl, heteroaryl, heteroarailcyl, alkylaryl, perhaloheteroaryl, acyl, acyloxy, acylamino, alkiamino, arylamino, aralkoxy, alkoxyalkyl, alkylthio, thioalkyl, arylthio, thioaryl, carboxylic acid or its derivatives, or sulfonic acid or its derivatives wherein the groups/substituents present on same or adjacent atoms such as carbon or nitrogen, together optionally and independently may form a five or a six or a seven membered ring optionally containing one or more double bonds and optionally containg one or more heteroatoms selected from O, N or S;

and wherein

R10 is independently selected from halogen, hydroxy, nitro, cyano, amino, oxo or oxime;

comprising the steps of:

a) reacting N-1-substituted hydrazinoacyl derivative of cyanopyrrolidine (formula-9a) or N-1-substituted hydrazinoacyl derivative of cyanothiazolidine(formula-10a).

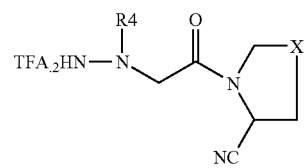

(9a); X = CH$_2$
(10a); X = S with acid chiorides/sulfonyl chloride in the presence of a base in an aprotic solvent at 0–30° C. for 1–8 hrs and b) isolating compounds of fonnula 9c or 10c by column chromatography.

12. The process as claimed in claim 11, wherein in step (a) of the process said base is tertiaryamine or pyridine and said aprotic solvent is acetonitrile tetrahydrofuran, dimethylformamide, dioxane, dichloromethane or chloroform.

13. The process as claimed in claim 12 wherein in step (a) of the process said base is triethylamine and said aprotic solvent is tetrahydrofuran.

14. A process for preparing compounds of formula 9b and 10b

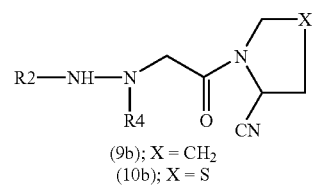

(9b); X = CH$_2$
(10b); X = S wherein

R4 and R2 are independently selected from hydrogen, perhaloalkyl, —(CO)NR8R9, —(CO)R8, —(CO)OR8, —SO$_2$R8, —SOR8, substituted or unsubstituted groups selected from linear or branched (C$_1$–C$_{12}$)alkyl, (C$_2$–C$_{12}$)alkenyl, (C$_3$–C$_7$)cycloalkyl, (C$_5$–C$_7$)cycloalkenyl, bicycloalkyl, amidino bicycloalkenyl, heterocycloalkyl, aryl, aralkyl, heteroaryl, heteroaralkyl, wherein one or more heteroatoms are independently selected from O, N or S;

R8 and R9 are independently selected from hydrogen or a substituted and unsubstituted group selected from linear or branched (C$_1$–C$_{12}$)alkyl, alkoxyaryl, alkoxyalkyl, alkoxycycloalkyl, alkoxyaryl, perhaloalkyl, $(C_2-C_{12})$alkenyl, $(C_3-C_7)$cycloalkyl, perhalocycloalkyl, haloheterocycloalkyl, cyanoheterocycloalkyl, perhaloheterocycloalkyl, $(C_5-C_7)$cycloalkenyl, bicycloalkyl, bicycloalkenyl, heterocycloalkyl, aryl, aralkyl, heteroaryl, heteroaralkyl, perhaloaryl, perhaloheteroaryl, wherein the groups represented by R8 and R9 when substituted, the substituents are optionally and independently bridged by —(CO)—, —(CO)O, —(CO)NH—, —NH—, —NR8-, —O—, —S—, —(SO)—, —(SO$_2$)—, —(SO$_2$)NH—, —NH(SO$_2$)—, —O(CO)— or —NH(CO)—; and are selected from halogen, hydroxy, nitro cyano, amino, oxo, oxime, unsubstittued or substituted by R10 for the groups selected from linear or branched $(C_1-C_8)$alkyl, $(C_3-C_7)$cycloalkyl, alkylcycloalkyl, perhaloalkyl, perhalocycloalkyl, aryl, aralkyl, alkylaryl, alkylheteroaryl, aralkoxylalkyl, perhaloaryl, alkylheterocycloalkyl, heterocycloalkyl, perhaloheterocyclyloalkyl, heteroaryl, heteroaralkyl, alkylaryl, perhaloheteroaryl, acyl, acyloxy, acylamino, alkiamino, arylamino, aralkoxy, alkoxyalkyl, alkylthio, thioalkyl, arylthio, thioaryl, carboxylic acid or its derivatives, or sulfonic acid or its derivatives wherein the groups/substituents present on same or adjacent atoms such as carbon or nitrogen, together optionally and independently may form a five or a six or a seven membered ring optionally containing one or more double bonds and optionally containg one or more heteroatoms selected from O, N or S, and wherein R10 is independently selected from halogen, hydroxy, nitro, cyano, amino, oxo or oxime;

comprising the steps of:

a) reacting a substituted aldehyde or ketone required to form R2 with a compound of formula 9a or 10a

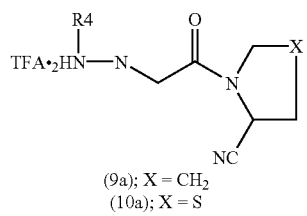

(9a); X = CH$_2$
(10a); X = S at 20–70° C. for 0.5–6 hrs in alcoholic solvent to give rise to the corresponding Schiff base and b) reduction of the Schiff base using a metal hydride in the presence of a catalytic amount of titanium tetrachloride in alcoholic solvent to give the corresponding target compound.

15. The process as claimed in claim 14, wherein in step (a) of the process said alcoholic solvent is methanol, ethanol or isopropanol, and in step (b) of the process said metal hydride is sodium cyanoborohydride or sodium borohydride.

16. The process as claimed in claim 14 wherein in step (a) of the process said alcoholic solvent is methanol and said Schiff base is sodium cyanoborohydride.

17. A process for preparing compounds of formulas 5a and 6a

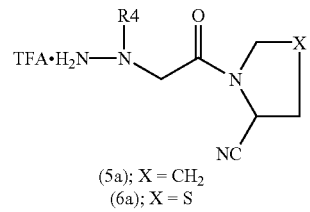

(5a); X = CH$_2$
(6a); X = S wherein

R4 is selected from hydrogen, perhaloalkyl, —(CO)NR8R9, —(CO)R8, —(CO)OR8, —SO$_2$R8, —SOR8, substituted or unsubstituted groups selected from linear or branched $(C_1-C_{12})$alkyl, $(C_2-C_{12})$alkenyl, $(C_3-C_7)$cycloalkyl, $(C_5-C_7)$cycloalkenyl, bicycloalkyl, amidino bicycloalkenyl, heterocycloalkyl, aryl, aralkyl, heteroaryl, heteroaralkyl, wherein one or more heteroatoms are independently selected from O, N or S;

R8 and R9 are independently selected from hydrogen or a substituted and unsubstituted group selected from linear or branched $(C_1-C_{12})$alkyl, alkoxyaryl, alkoxyalkyl, alkoxycycloalkyl, alkoxyaryl, perhaloalkyl, $(C_2-C_{12})$alkenyl, $(C_3-C_7)$cycloalkyl, perhalocycloalkyl, haloheterocycloalkyl, cyanoheterocycloalkyl, perhaloheterocycloalkyl, $(C_5-C_7)$cycloalkenyl, bicycloalkyl, bicycloalkenyl, heterocycloalkyl, aryl, aralkyl, heteroaryl, heteroaralkyl, perhaloaryl, perhaloheteroaryl, wherein the groups represented by R8 and R9 when substituted, the substituents are optionally and independently bridged by —(CO)—, —(CO)O, —(CO)NH—, —NH—, —NR8—, —O—, —S—, —(SO)—, —(SO$_2$)—, —(SO$_2$)NH—, —NH(SO$_2$)—, —O(CO)— or —NH(CO)—; and are selected from halogen, hydroxy, nitro cyano, amino, oxo, oxime, unsubstittued or substituted by R10 for the groups selected from linear or branched $(C_1-C_8)$alkyl, $(C_3-C_7)$cycloalkyl, alkylcycloalkyl, perhaloalkyl, perhalocycloalkyl, aryl, aralkyl, alkylaryl, alkylheteroaryl, aralkoxylalkyl, perhaloaryl, alkylheterocycloalkyl, heterocycloalkyl, perhaloheterocyclyloalkyl, heteroaryl, heteroaralkyl, alkylaryl, perhaloheteroaryl, acyl, acyloxy, acylamino, alkiamino, arylamino, aralkoxy, alkoxyalkyl, alkylthio, thioalkyl, arylthio, thioaryl, carboxylic acid or its derivatives, or sulfonic acid or its derivatives wherein the groups/substituents present on same or adjacent atoms such as carbon or nitrogen, together optionally and independently may form a five or a six or a seven membered ring optionally containing one or more double bonds and optionally containg one or more heteroatoms selected from O, N or S, and wherein R10 is independently selected from halogen, hydroxy, nitro, cyano, amino, oxo or oxime; and "Boc" in process step (a) below stands for "tertiary Butyloxy Carbonyl", comprising the steps of:

a) reacting chloroacyl-2-cyanopyrrolidine or chloroacyl-4-cyanothiazolidine with Boc-carbazate using aprotic solvent in the presence of a base with a catalytic amount of potassium iodide at 40–110° C. for 6–50 hrs, to give a compound of formula 5 or 6 respectively,

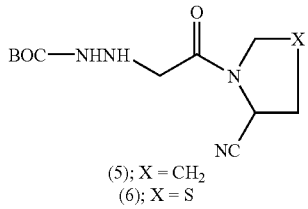

(5); X = CH₂
(6); X = S b) reacting the compound of formula 5 or 6 from step (a) above, with carbonyl chloride or acid chloride or sulphonyl chloride in the presence of a base in an aprotic solvent at 0–30° C. for 0.5–6 hrs and c) deprotecting compounds obtained in step (b) using trifluoroacetic acid at 0–30° C. for 0.25–2 hrs to give the corresponding target compound of formula 5a or 6a respectively.

18. The process as claimed in claim 17, wherein in step (a) of the process said aprotic solvent is acetonitrile, tetrahydrofuran, dimethylformamide or dioxane, and said base is alkali or alkali earth metal carbonates or tertiaryamine; and in step (b) of the process said base is tertiaryamine or pyridine, and said aprotic solvent is acetonitrile, tetrahydrofuran, dimethylformamide or dioxane.

19. The process as claimed in claim 18 wherein in step (a) of the process said aprotic solvent is tetrahydrofuron and said base is potassium carbonate in the presence of a catalytic amount of potassium iodide; and in step (b) of the process said base is triethylamine and said aprotic solvent is tetrahydrofuran.

* * * * *